(12) United States Patent
Donohue et al.

(10) Patent No.: US 12,305,215 B2
(45) Date of Patent: *May 20, 2025

(54) MICROBIOMES AND METHODS FOR PRODUCING MEDIUM-CHAIN FATTY ACIDS FROM ORGANIC SUBSTRATES

(71) Applicant: WISCONSIN ALUMNI RESEARCH FOUNDATION, Madison, WI (US)

(72) Inventors: Timothy James Donohue, Middleton, WI (US); Matthew Scarborough, Madison, WI (US); Daniel Noguera, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 574 days.

This patent is subject to a terminal disclaimer.

(21) Appl. No.: 17/571,209

(22) Filed: Jan. 7, 2022

(65) Prior Publication Data

US 2022/0127651 A1 Apr. 28, 2022

Related U.S. Application Data

(63) Continuation of application No. 16/433,639, filed on Jun. 6, 2019, now Pat. No. 11,242,544.

(60) Provisional application No. 62/846,378, filed on May 10, 2019, provisional application No. 62/697,249, filed on Jul. 12, 2018, provisional application No. 62/696,677, filed on Jul. 11, 2018.

(51) Int. Cl.
| | | |
|---|---|---|
| C12P 7/6409 | (2022.01) | |
| C12N 1/20 | (2006.01) | |
| C12R 1/225 | (2006.01) | |

(52) U.S. Cl.
CPC .......... C12P 7/6409 (2013.01); C12N 1/205 (2021.05); *C12P 2203/00* (2013.01); *C12R 2001/225* (2021.05)

(58) Field of Classification Search
CPC . C12P 7/42; C12P 7/52–56; A61K 35/74–748
See application file for complete search history.

(56) References Cited

U.S. PATENT DOCUMENTS

| | | | |
|---|---|---|---|
| 8,835,665 B2 | 9/2014 | Reaney et al. | |
| 9,708,630 B1 | 7/2017 | Pfleger | |
| 2014/0199281 A1* | 7/2014 | Henn | A61K 38/13 424/93.46 |
| 2014/0342438 A1* | 11/2014 | Allen-Vercoe | A61K 35/745 435/252.4 |
| 2015/0050246 A1 | 2/2015 | Jones et al. | |
| 2015/0374761 A1 | 12/2015 | Sadowsky et al. | |

FOREIGN PATENT DOCUMENTS

| | | |
|---|---|---|
| CN | 104328144 A | 2/2015 |
| WO | 2008070561 A1 | 6/2008 |
| WO | 2013022998 A2 | 2/2013 |
| WO | 2013037068 A1 | 3/2013 |
| WO | 2014152484 A1 | 9/2014 |
| WO | WO-2017120495 A1 * | 7/2017 ............. A23K 10/18 |

OTHER PUBLICATIONS

Andersen et al. "A Clostridium Group IV Species Dominates and Suppresses a Mixed Culture Fermentation by Tolerance to Medium Chain Fatty Acids Products" Front. Bioeng. Biotechnol., Feb. 19, 2017, Article 8, 10 pages (Year: 2017).*
Stamatopoulou et al. "Fermentation of Organic Residues to Beneficial Chemicals: a Review of Medium-Chain Fatty Acid Production" Processes 2020, 8, 1571, 25 pages (Year: 2020).*
Abdullah, M. and French, D., Substrate Specificity of Pullulanase. *Archives of Biochemical and Biophysical Research Communications*. 1970. 137, 483-493.
Aboulnaga, E.H., Pinkenburg, O., Schiffels, J., El-Refai, A. Buckel, W. and Selmer, T., Effect of an Oxygen-Tolerant Bifurcating. Butyryl Coenzyme A Dehydrogenase/Electron-Transferring Flavoprotein Complex from *Clostridium difficile* on Butyrate Production in *Escherichia coli. Journal of Bacteriology*. 2013. 195, 3704-3713.
Agler, M.T., Wrenn, B.A., Zinder, S.H. and Angenent, L.T., Waste to bioproduct conversion with undefined mixed cultures: the carboxylate platform. *Trends in Biotechnology*. 2011. 29 (2), 70-78.
Agler, M.T., Spirito, C. M., Usack, J. G., Werner, J. J., Angenent, L. T. Chain elongation with reactor microbiomes: upgrading dilute ethanol to medium-chain carboxylates. *Energy Environ. Sci.*, 2012, 5, 8189.
Anders, S., Pyl, P.T. and Huber, W., HTSeq—a Python framework to work with high-throughput sequencing data. *Bioinformatics*. 2015. 31 (2), 166-169.
Andersen, S.J., Candry, P., Basadre, T., Khor, W.C., Roume, H., Hernandez-Sanabria, E., Coma, M. and Rabaey, K., Electrolytic extraction drives volatile fatty acid chain elongation through lactic acid and replaces chemical pH control in thin stillage fermentation. *Biotechnology for Biofuels*. 2015. 8:221.
Andersen, S.J., De Groof, V., Khor, W.C., Roume, H., Props, R., Coma, M. and Rabaey, K., *A Clostridium* Group IV Species Dominates and Suppresses a Mixed Culture Fermentation by Tolerance to Medium Chain Fatty Acids Products. *Frontiers in Bioengineering and Biotechnology*. 2017. 5, 8.

(Continued)

*Primary Examiner* — Thane Underdahl
(74) *Attorney, Agent, or Firm* — Daniel A. Blasiole; DeWitt LLP

(57) ABSTRACT

Microbiome compositions and uses thereof. The microbiome compositions include a set of microbes. The sets of microbes contain members of *Lactobacillaceae, Eubacteriaceae, Lachnospiraceae*, and *Coriobacteriaceae*. The number of individual physical microbes in the set constitutes a certain percentage of the total number of individual physical microbes in the microbiome composition. The microbiome compositions can be used for producing medium-chain fatty acids from organic substrates through anaerobic fermentation in a medium. The medium can include lignocellulosic stillage.

20 Claims, 16 Drawing Sheets
(15 of 16 Drawing Sheet(s) Filed in Color)
Specification includes a Sequence Listing.

(56) References Cited

OTHER PUBLICATIONS

Angenent, L.T., Richter, H., Buckel, W., Spirito, C.M., Steinbusch, K.J.J,, Plugge, C.M., Strik, D., Grootscholten, T.I.M., Buisman, C.J.N. and Hamelers, H.V.M., Chain Elongation with Reactor Microbiomes: Open-Culture Biotechnology to Produce Biochemicals. *Environmental Science& Technology*. 2016. 50, 2796-2810.

Austin, S., Kontur, W.S., Ulbrich, A., Oshlag, J.Z., Zhang, W., Higbee, A., Zhang, Y., Coon, J.J., Hodge, D.B., Donohue, T.J. and Noguera, D.R., Metabolism of Multiple Aromatic Compounds in Corn Stover Hydrolysate by *Rhodopseudomonas palustris*. *Environmental Science& Technology*. 2015. 49, 8914-8922.

Balan, V., Bals, B., Chundawat, S.P.S., Marshall, D. and Dalem D.E., Lignocellulosic Biomass Pretreatment Using AFEX. *Biofuels: Methods and Protocols, Methods in Molecular Biology*. 2009. 581, 61-77.

Barter, R.L. and Yu, B., Superheat: An R package for Creating Beautiful and Extendable Heatmaps for Visualizing Complex Data. *Journal of Computational and Graphical Statistics*. 2018. 27(4):910-922.

Bleckwedel, J., Teran, L.C., Bonacina, J., Saavedra, L., Mozzi, F. and Raya, R., Draft Genome Sequence of the Mannitol-Producing Strain *Lactobacillus mucosae* CRL573. *Genome Announcements*. 2014. 2(6).

Buckel, W. and Thauer, R.K., Energy conservation via electron bifurcating ferredoxin reduction and proton/Na+ translocating ferredoxin oxidation. *Biochimica et Biophysica Acta(BBA)—Bioenergetics*. 2013. 1827, 94-113.

Caporaso, J.G., Bittinger, K., Bushman, F.D., Desantis, T.Z., Andersen, G.L. and Knight, R., PyNAST: a flexible tool for aligning sequences to a template alignment. *Bioinformatics*. 2010. 26(2), 266-267.

Caporaso, J.G., Kuczynski, J., Stombaugh, J., Bittinger, K., Bushman, F.D., Costello, E.K., Fierer, N., Pena, A.G., Goodrich, J.K., Gordon, J.I., Huttley, G.A., Kelley, S.T., Knights, D., Koenig, J.E., Ley, R.E., Lozupone, C.A., Mcdonald, D., Muegge, B.D., Pirrung, M., Reeder, J., Sevinsky, J.R., Turnbaugh, P.J., Walters, W.A., Widmann, J., Yatsunenko, T., Zaneveld, J. and Knight, R., Qiime allows analysis of high-throughput community sequencing data. *Nature Methods*. 2010. 7(5), 335-336.

Chao, S.H., Sasamoto, M., Kudo, Y., Fujimoto, J, Tsai, Y.C. and Watanabe, K., *Lactobacillus odoratitofui* sp. Nov., isolated from stinky tofu brine. *International Journal of Systematic and Evolutionary Microbiology*. 2010. 60, 2903-2907.

Collins, M.D. and Wallbanks, S., Comparative sequence analyses of the 16S rRNA genes of *Lactobacillus rimae* and *Streptococcus parvulus*: Proposal for the creation of a new genus *Atopobium*. *FEMS Microbiology Letters*. 1992. 95, 235-240.

Darling, A.E., Jospin, G., Lowe, E., Matsen Iv, F.A., Bik, H.M. and Eisen, J.A., PyhloSift: phylogenetic analysis of genomes and metagenomes. *Peer J*. 2014. 2: e243.

De Kok, S., Meijer, J., Van Loosdrecht, M.C.M. and Kleerebezem, R., Impact of dissolved hydrogen partial pressure on mixed culture fermentations. *Applied Microbiology and Biotechnology*. 2013. 97: 2617-2625.

Dellaglio, F., Vancanneyt, M., Endo, A., Vandamme, P., Felis, G.E., Castioni, A., Fujimoto, J., Watanabe, K. and Okada, S., *Lactobacillus durianis* Leisner et al. 2002 is a later heterotypic synonym of *Lactobacillus vaccinostercus* Kozaki and Okada 1983. *International Journal of Systematic and Evolutionary Microbiology*. 2006. 56, 1721-1724.

Demmer, J.K., Pal Chowdhury, N., Selmer, T., Ermler, U. and Buckel, W., The semiquinone swing in the bifurcating electron transferring flavoprotein/butyryl-CoA dehydrogenase complex from *Clostridium difficile*. *Nature Communications*. 2017. 8: 1577.

Devarapalli, P., Deshpande, N. and Hirwani, R.R., Xylose utilization in ethanol production: a patent landscape. *Biofuels, Bioproducts and Biorefining*. 2016. 10, 534-541.

Dewhirst, F.E., Paster, B.J., Tzellas, N., Coleman, B., Downes, J., Spratt, D.A. and Wade, W.G., Characterization of novel human oral isolates and cloned 16S rDNA sequences that fall in the family *Coriobacteriaceae*: description of *Olsenella* gen. nov., reclassification of *Lactobacillus uli* as *Olsenella uli* comb. nov. and description of *Olsenella profusa* sp. nov. *International Journal of Systematic and Evolutionary Microbiology*. 2001. 51, 1797-1804.

Dodd, D., Kocherginskaya, S.A., Spies, M.A., Beery, K.E., Abbas, C.A., Mackie, R.I. and Cann, I.K.O., Biochemical Analysis of a $\beta\text{-}^D$-Xylosidase and a Bifunctional Xylanase-Ferulic Acid Esterase from a Xylanolytic Gene Cluster in *Prevotella ruminicola* 23. *Journal of Bacteriology*. 2009. 191(10), 3328-3338.

Duncan, S.H., Aminov, R.I., Scott, K.P., Louis, P., Stanton, T.B. and Flint, H.J., Proposal of *Roseburia faecis* sp. nov., *Roseburia hominis* sp. nov. and *Roseburia inulinivorans* sp. nov., based on isolates from human faeces. *International Journal of Systematic and Evolutionary Microbiology*. 2006. 56, 2437-2441.

Duncan, S.H., Hold, G.L., Barcenilla, A., Stewart, C.S. and Flint, H.J., *Roseburia intestinalis* sp. nov., a novel saccharolytic, butyrate-producing bacterium from human faeces. *International Journal of Systematic and Evolutionary Microbiology*. 2002. 52, 1615-1620.

Edgar, R.C., Search and clustering orders of magnitude faster than BLAST. *Bioinformatics*. 2010. 26(19), 2460-2461.

Edgar, R.C., Muscle: a multiple sequence alignment method with reduced time and space complexity. *BMC Bioinformatics*. 2004. 5: 113.

Edgar, R.C., Muscle: multiple sequence alignment with high accuracy and high throughput. *Nucleic Acids Research*. 2004. 32(5), 1792-1797.

English, A. C., Richards, S., Han, Y., Wang, M., Vee, V., Qu, J., Qin, X., Muzny, D.M., Reid, J.G., Worley, K.C. and Gibbs, R.A., Mind the Gap: Upgrading Genomes with Pacific Biosciences RS Long-Read Sequencing Technology. *PLoS One*. 2012. 7(11), e47768.

Eren, A.M., Esen, O.C., Quince, C., Vineis, J.H., Morrison, H.G., Sogin, M.L. and Delmont, T.O., Anvi'o: an advanced analysis and visualization platform for 'omics data. *PeerJ*. 2015. 3, e1319.

Garde, A., Jonsson, G., Schmidt, A.S. and Ahring, B.K., *Bioresource Technology*. 2002. 81, 217-223.

Ge, S., Usack, J.G., Spirito, C.M. and Angenent, L.T., Long-Term n-Caproic Acid Production from Yeast-Fermentation Beer in an Anaerobic Bioreactor with Continuous Product Extraction. *Environmental Science& Technology*. 2015. 49, 8012-8021.

Gelfand, I., Sahajpal, R., Zhang, X., Izaurralde, R.C., Gross, K.L. and Robertson, G.P., Sustainable Bioenergy Production from Marginal Lands in the US Midwest. *Nature*. 2013. 493, 514-517.

Gerbrandt, K., Chu, P.L., Simmonds, A., Mullins, K.A., Maclean, H.L., Griffins, W.M. and Saville, B.A., *Current Opinion in Biotechnology*. 2016. 38, 63-70.

Ghosh, S., Conrad, J.R. and Klass, D.L., Anaerobic Acidogenesis of Wastewater Sludge. *Research Journal of the Water Pollution Control Federation*. 1975. 47, 30-45.

Grootscholten, T.I.M., Dal Borgo, F.K., Hamelers, H.V.M. and Buisman, C.J.N., Promoting Chain Elongation in Mixed Culture Acidification Reactors by Addition of Ethanol. *Biomass& Bioenergy*. 2013. 48, 10-16.

Grootscholten, T.I.M., Strik,. P. B. T. B. K., Steinbusch, J.J., Buisman, C.J.N. and H. V. M. Hamelers. Two-stage Medium Chain Fatty Acid (MCFA) Production from Municipal Solid Waste and Ethanol. *Applied Energy*. 2014. 116, 223-229.

Haas, B.J., Gevers, D., Earl, A.M., Feldgarden, M., Ward, D.V., Giannoukos, G., Ciulla, D., Tabbaa, D., Highlander, S.K., Sodergren, E., Methe, B., Desantis, T.Z., Petrosino, J.F., Knight, R., Birren, B.W. and Consortium, H.M., Chimeric 16S rRNA Sequence Formation and Detection in Sanger and 454-Pyrosequenced PCR Amplicons. *Genome Research*. 2011. 21, 494-504.

Han, W., He, P., Shao, L. and Lu, F., Metabolic Interactions of a Chain Elongation Microbiome. *Applied and Environmental Microbiology*. 2018. DOI: 10.1128/AEM.01614-18.

Hegner, R., Koch, C., Riechert, V. and Harnisch, F., Microbiome-based Carboxylic Acids Production: from Serum Bottles to Bioreactors. *RSC Advances*. 2017. 7, 15362-15371.

Holdeman, L.V., Elizabeth, C.P. and Moore, W.E.C., Amended Description of Ramibacterium Alactolyticum Prevot and Taffanel with Proposal of a Neotype Strain. *International Journal of Systematic Bacteriology*. 1967. 17, 323-341.

(56) References Cited

OTHER PUBLICATIONS

Holtzapple, M.T. and Granda, C.B., Carboxylate Platform: The MixAlco Process Part 1: Comparison of Three Biomass Conversion Platforms. *Biotechnology and Applied Biochemistry*. 2009. 156, 95-106.

Humbird, D., Davis, R., Tao, L., Kinchin, C., Hsu, D., Aden, A., Schoen, P., Lukas, J., Olthof, B., Worley, M., Sexton, D. and Dudgeon, D. Process Design and Economics for Biochemical Conversion of Lignocellolosic Biomass to Ethanol. *National Renewable Energy Laboratory*. 2011.

Hyatt, D., Chen, G.L., Locascio, P.F., Land, M.L., Larimer, F.W. and Hauser, L.J., Prodigal: Prokaryotic Gene Recognition and Translation Initiation Site Identification. *BMC Bioinformatics*. 2010. 11, 119.

Jeon, B.S., Choi, O., Um, Y. and Sang, B.I., Production of Medium-Chain Carboxylic Acids by Megasphaera sp. MH with Supplemental Electron Acceptors. *Biotechnology for Biofuels*. 2016. 9.

Jovita, M.R., Collins, M.D., Sjoden, B. and Falsen, E., Characterization of a Novel Atopobium Isolate from the Human Vagina: Description of Atopobium Vaginae sp. Nov. *International Journal of Systematic Bacteriology*. 1999. 49, 1573-1576.

Kenealy, W.R., Cao, Y. and Weimer, P.J., Production of Caproic Acid by Cocultures of Ruminal Cellulolytic Bacteria and Clostridium Kluyveri Grown on Cellulose and Ethanol. *Applied Microbiology and Biotechnology*. 1995. 44, 507-513.

Kielbasa, S.M., Wan, R., Sato, K., Horton, P. and Frith, M.C., Adaptive Seeds Tame Genomic Sequence Comparison. *Genome Research*. 2011. 21, 487-493.

Kim, M., Oh, H.S., Park, S.C. and Chun, J., Towards a Taxonomix Coherence Between Average Nucleotide Identity and 16S rRNA gene Sequence Similarity for Species Demarcation of Prokaryotes. *International Journal of Systematic and Evolutionary Microbiology*. 2014. 64, 1825-1825.

Kleerebezem, M., Boekhorst, J., Van Kranenburg, R., Molenaar, D., Kuipers, O.P., Leer, R., Tarchini, R., Peters, S.A., Sandbrink, H.M., Fiers, M.W., Stiekema, W., Lankhorst, R.M., Bron, P.A., Hoffer, S.M, Groot, M.N., Kerkhoven, R., De Vries, M., Ursing, D., De Vos, W.M. and Siezen, R.J., Complete Genome Sequence of Lactobacillus. *Proceedings of the National Academy of Sciences of the United States of America*. 2003. 100, 1990-1995.

Klindworth, A., Pruesse, E., Schweer, T., Peplies, J., Quast, C., Horn, M. and Glockner, F.O., Evaluation of General 16S Ribosomal RNA gene PCR Primers for Classical and Next-Generation Sequencing-Based Diversity Studies. *Nucleic Acids Research*. 2013. 41.

Konwar, K.M., Hanson, N.W., Bhatia, M.P., Kim, D., Wu, S.J., Hahn, A.S., Morgan-Lang, C., Cheung, H.K. and HALLAM,S.J., MetaPathways v2.5: Quantitative Functional, Taxonomic and Usability Improvements. *Bioinformatics*. 2015. 31, 3345-3347.

Kopylova, E., Noe, L. and Touzet, H., SortMeRNA: Fast and Accurate Filtering of Ribosomal RNAs in Metatranscriptomic Data. *Bioinformatics*. 2012. 28, 3211-3217.

Kraatz, M., Wallace, R.J. and Svensson, L., Olsenella Umbonata sp. Nov., a Microaerotolerant Anaerobic Lactic Acid Bacterium from the Sheep Rumen and Pig Jejunum, and Emended Descriptions of Olsenella, Olsenella uli, and Olsenella Profusa. *International Journal of Systematic and Evolutionary Microbiology*. 2011. 61, 795-803.

Krooneman, J., Faber, F., Alderkamp, A.C., Elferink, S.J.H.W.O., Driehuis, F., Cleenwerck, I., Swings, J., Gottschal, J.C. and Vancanneyt, M., Lactobacillus Diolivorans sp. nov., a 1, 2-Propanediol-Degrading Bacterium Isolated from Aerobically Stable Maize Silage. *International Journal of Systematic and Evolutionary Microbiology*. 2002. 52, 639-646.

Kucek, L.A., Nguyen, M. and Angenent, L.T., Conversion Of L-Lactate Into N-Caproate By A Continuously Fed Reactor Microbiome. *Water Research*. 2016. 93, 163-171.

Kucek, L.A., Spirito, C.M. and Angenent, L.T., High N-Caprylate Productivities and Specificities from Dilute Ethanol and Acetate: Chain Elongation with Microbiomes to Upgrade Products from Syngas Fermentation. *Energy& Environmental Science*. 2016. 9, 3482-3494.

Kucek, L.A., Xu, J.J., Nguyen, M. and Angenent, L.T., Waste Conversion into n-Caprylate and n-Caproate: Resource Recovery from Wine Lees Using Anaerobic Reacto Microbiomes and In-line Extraction. *Frontiers in Microbiology*. 2016, 7.

Kumar, A. and Sokhansanj, S., Switchgrass (Panicum Vigratum, L.) Delivery to a Biorewnery Using Integrated Biomass Supply Analysis and Logistics (IBSAL) Model. *Bioresource Technology*. 2007. 98, 1033-1044.

Larkin M. A., et al. CLUSTALW2, ClustalW and ClustalX version 2. *Bioinformatics*. 2007. 23(21): 2947-2948.

Lawlis, V.B., Dennis, M.S., Chen, E.Y., Smith, D.H. and Henner, D.J., Cloning and Sequencing of the Xylose Isomerase and Xylulose Kinase Genes of *Escherichia coli*. *Applied and Environmental Microbiology*. 1984. 47, 15-21.

Lawson, C.E., Wu, S., Bhattacharjee, A.S., Hamilton, J.J., Mcmahon, K.D., Goel, R. and Noguera, D.R., Metabolic Network Analysis Reveals Microbial Community Interactions in Anammox Granules. *Nature Communications*. 2017. 8, 15416.

Li, X., Jensen, R.L., Hojberg, O., Canibe, N. and Jensen, B.B., Olsenella Scatoligenes Sp. Nov., A 3-Methylindole-(Skatole) and 4-Methylphenol-(P-Cresol) Producing Bacterium Isolated from Pig Faeces. *International Journal of Systematic and Evolutionary Microbiology*. 2015. 65, 1227-1233.

Li, F., Hinderberger, J., Seedorf, H., Zhang, J., Buckel, W. and Thauer, R.K., Coupled Ferredoxin And Crotonyl Coenzyme A (Coa) Reduction With NADH Catalyzed By The Butyryl-Coa Dehydrogenase/ Etf Complex From Clostridium Kluyveri. *Journal of Bacteriology*. 2008. 190, 843-850.

Liang, S. and Wan, C., Carboxylic Acid Production from Brewer's Spent Grain Via Mixed Culture Fermentation. *Bioresource Technology*. 2015. 182, 179-183.

Lombard, V., Golaconda Ramulu, H., Drula, E., Coutinho, P.M. and Henrissat, B., The Carbohydrate-Active Enzymes Database (CAZy) in 2013. *Nucleic Acids Research*. 2014. 42, D490-495.

Magoc, T. and Salzberg, S.L., Flash: Fast Length Adjustment of Short Reads to Improve Genome Assemblies. *Bioinformatics*. 2011. 27, 2957-2963.

Mcmurdie, P.J. and Holmes, S., Phyloseq: An R Package for Reproducible Interactive Analysis and Graphics of Microbiome Census Data. *PLoS One*. 2013. 8.

Nasr, N., Elbeshbishy, E., Hafez, H., Nakhla, G. and El Naggar, M.H., Comparative Assessment of Single-Stage and Two-Stage Anaerobic Digestion for the Treatment of Thin Stillage. *Bioresource Technology*. 2012. 111, 122-126.

Nelson, R., Peterson, D., Karp, E., Beckham, G. and Salvachúa., D., Mixed Carboxylic Acid Production by Megasphaera elsdenii from Glucose and Lignocellulosic Hydrolysate. *Fermentation*. 2017. 3, 10.

Notredame et al. T-Coffee: A novel method for multiple sequence alignments. *Journal of Molecular Biology*. 2000. 302: 205-217.

Nurk, S., Meleshko, D., Korobeynikov, A. and Pevzner, P.A., MetaSPAdes: A New Versatile Metagenomic Assembler. *Genome Research*. 2017. 27, 824-834.

Ong, R.G., Higbee, A., Bottoms, S., Dickinson, Q., Xie, D., Smith, S.A., Serate, J., Pohlmann, E., Jones, A.D., Coon, J.J., Sato, T.K.,Sanford, G.R., Eilert, D., Oates, L.G., Piotrowski, U.S., Bates, D.M., Cavalier, D. and Zhang, Y. Inhibition Of Microbial Biofuel Production In Drought-Stressed Switchgrass Hydrolysate. *Biotechnology for Biofuels*. 2016. 9, 237.

Parks, D.H., Imelfort, M., Skennerton, C.T., Hugenholtz, P. and Yson, G.W., CheckM: Assessing The Quality Of Microbial Genomes Recovered From Isolates, Single Cells, And Metagenomes. *Genome Research*. 2015. 25, 1043-1055.

Parreiras, L.S., Breuer, R.J., Avanasi Narasimhan, R., Higbee, A.J., La Reau, A., Tremaine, M., Qin, L., Willis, L.B., Bice, B.D., Bonfert, B.L., Pinhancos, R.C., Balloon, A.J., Uppugundla, N., Liu, T., Li, C., Tanjore, D., Ong, I.M., Li, H., Pohlmann, E.L., Serate, J., Withers, S.T., Simmons, B.A., Hodge, D.B., Westphall, M.S., Coon, J.J., Dale, B.E., Balan, V., Keating, D.H., Zhang, Y., Landick, R., Gasch, A.P. and Sato, T.K., Engineering and Two-Stage Evolution

(56) References Cited

OTHER PUBLICATIONS of a Lignocellulosic Hydrolysate-Tolerant Saccharomyces Cerevisiae Strain for Anaerobic Fermentation of Xylose from AFEX Pretreated Corn Stover. *PLoS One*. 2014. 9, e107499.

Pinheiro, J. 2017. Package 'nlme'. Retrieved from cran.r-project.org/web/packages/nlme/nlme.pdf.

Quast, C., Pruesse, E., Yilmaz, P., Gerken, J., Schweer, T., Yarza, P., Peplies, J. and Glockner, F.O., The SILVA Ribosomal RNA Gene Database Project: Improved Data Processing and Web-Based Tools. *Nucleic Acids Research*. 2013. 41, D590-D596.

Richter, M., Rossello-Mora, R., Oliver Glockner, F. and Peplies, J. JSpeciesWS: A Web Server for Prokaryotic Species Circumscription Based on Pairwise Genome Comparison. *Bioinformatics*. 2016. 32, 929-931.

Rodriguez, J., Kleerebezem, R., Lema, J.M. and Van Loosdrecht, M.C.M, Modeling Product Formation in Anaerobic Mixed Culture Fermentations. *Biotechnology and Bioengineering*. 2006. 93, 592-606.

Ronimus, R.S. and Morgan, H.W., The Biochemical Properties and Phylogenies of Phosphofructokinases from Extremophiles. *Extremophiles*. 2001. 5, 357-373.

Roos, S., Karner, F., Axelsson, L. and Jonsson, H., Lactobacillus Mucosae Sp. Nov., A New Species With In Vitro Mucus-Binding Activity Isolated From Pig Intestine. *International Journal of Systematic and Evolutionary Microbiology*. 2000. 50 Pt 1, 251-258.

Sakamoto, T. and Thibault, J.F., Exo-Arabinanase of Penicillium Chrysogenum Able to Release Arabinobiose from a-1,5-L-Arabinan. *Applied and Environmental Microbiology*. 2001. 67, 3319-3321.

Sarria, S., Kruyer, N.S. and Peralta-Yahy, P., Microbial Synthesis of Medium-Chain Chemicals from Renewables. *Nature Biotechnology*. 2017. 35, 1158-1166.

Scarborough MJ, Lawson CE, Hamilton JJ, Donohue TJ, Noguera Dr. Metatranscriptomic and Thermodynamic Insights into Medium-Chain Fatty Acid Production Using an Anaerobic Microbiome. *mSystems*. 2018. DOI: 0.1128/msystems.00221-18.

Scarborough MJ, Lynch G, Dickson M, Mcgee M, Donohue TJ, Noguera Dr., Increasing the Economic Value of Lignocellulosic Stillage Through Medium-Chain Fatty Acid Production. *Biotechnology for Biofuels*. Jul. 2018. 19;11:200. doi: 10.1186/s13068-018-1193-x. eCollection 2018.

Seider, W.D., Seader, J.D., Lewin, D.R. and Widagdo, S., "Product and process design principles: synthesis, analysis, and evaluation." John Wiley and Sons, Inc., Hoboken, New Jersey, 3rd ed., 2009. (Book).

Senate and House of Representatives of the United States of America. Energy Policy Act of 2005, US Government Publishing Office, Washington, D.C., 2005.

Senate and House of Representatives of the United States of America. Energy Independence and Security Act of 2007, US Government Publishing Office, Washington, D.C., 2007.

Smith, P.K., Krohn, R.I., Hermanson, G.T, Mallia, A.K., Gartner, F.H., Provenzano, M.D., Fujimoto, E.K., Goeke, N.M., Olson, B.J. and Klenk, D.C., Measurement of Protein Using Bicinchoninic Acid. *Analytical Biochemistry*. 1985. 150, 76-85.

Sokhansanj, S., Mani, S., Turhollow, A., Kumar, A., Bransby, D., Lynd, L. and Laser, M., Large-Scale Production, Harvest and Logistics of Switchgrass (Panicum Virgatum L.)—Current Technology And Envisioning A Mature Technology. *Biofuels, Bioproducts and Biorefining*. 2009. 3, 124-141.

Spirito, C.M., Richter, H., Rabaey, K., Stams, A.J., and Angenent, L.T., Chain Elongation in Anaerobic Reactor Microbiomes to Recover Resources from Waste. *Current Opinion in Biotechnology*. 2014. 27, 115-122.

Stamatakis, A. RAxML Version 8: A Tool for Phylogenetic Analysis and Post-Analysis of Large Phylogenies. *Bioinformatics*. 2014. 30, 1312-1313.

Stams, A.J. and Plugge, C.M., Electron Transfer In Syntrophic Communities Of Anaerobic Bacteria And Archaea. *Nature Reviews Microbiology*. 2009. 7, 568-577.

Stanton, T.B. and Savage, D.C., Roseburia Cecicola Gen. Nov., Sp. Nov., A Motile, Obligately Anaerobic Bacterium From A Mouse Cecum. *International Journal of Systematic Bacteriology*. 1983. 33, 618-627.

Strauber, H., Lucas, R. and Kleinsteuber, S., Metabolic and Microbial Community Dynamics During the Anaerobic Digestion of Maize Silage in a Two-Phase Process. *Applied Microbiology and Biotechnology*. 2016. 100, 479-491.

Thompson, J.D., Higgins, D. G., Gibson, T. J., Clustal, W: improving the sensitivity of progressive multiple sequence alignment through sequence weighting, position-specific gap penalties and weight matrix choice. *Nucleic Acids Research*. 1994. 22: 4673-4680.

Tian, Z.L., Mohan, G.R., Ingram, L. and Pullammanappallil, P., Anaerobic Digestion for Treatment of Stillage From Cellulosic Bioethanol Production. *Bioresource Technology*. 2013. 144, 387-395.

Urban, C., Xu, J., Strauber, H., Dos Santos Dantas,T.R., Mühlenberg, J., Härtig, C., Angenent, L.T. and Harnisch, F., *Energy& Environmental Science*. 2017. DOI: 10.1039/c7ee01303e.

Vasudevan, D., Richter, H. and Angenent, L.T., *Bioresource Technology*. 2014. 151, 378-382.

W. E. F. American Public Health Association, and American Water Works Association Standard Methods for the Examination of Water and Wastewater: 21st Edition, American Public Health Association, 2005 (Book).

Wang, Z.X., Zhuge, J., Fang, H.Y. and Prior, B.A., Anaerobic Digestion for Treatment of Stillage from Cellulosic Bioethanol Production. *Biotechnology Advances*. 2001. 19, 201-223.

Weimer, P.J., Nerdahl, M. and Brandl, D.J., Production Of Medium-Chain Volatile Fatty Acids by Mixed Ruminal Microorganisms is Enhanced by Ethanol in Co-Culture with Clostridium Kluyveri. *Bioresource Technology*. 2015. 175, 97-101.

Wu, Y.W., Simmons, B.A. and Singer, S.W., MaxBin 2.0: An Automated Binning Algorithm to Recover Genomes from Multiple Metagenomic Datasets. *Bioinformatics*. 2016. 32, 605-607.

Xiong, B.Y., Richard, T.L. and Kumar, M., Integrated acidogenic digestion and carboxylic acid separation by nanofiltration membranes for the lignocellulosic carboxylate platform. *Journal of Membrane Science*. 2015. 489, 275-283.

Yemm. E.W. and Willis, A.J., The Estimation of Carbohydrates in Plant Extracts by Anthrone. *Biochemical Journal*. 1954. 57, 508-514.

Yu, C.S., Chen, Y.C.,Lu, C.H. and Hwang, J.K., Prediction of Protein Subcellular Localization. *Proteins*. 2006. 64, 643-651.

Zhang, F., Zhang, Y., Chen, M., Van Loosdrecht, M.C.M. and Zeng, R.J., A Modified Metabolic Model for Mixed Culture Fermentation With Energy Conserving Electron Bifurcation Reaction and Metabolite Transport Energy. *Biotechnology and Bioengineering*. 2013. 110, 1884-1894.

Zhang, Y. and Vadlani, P.V., Lactic Acid Production from Biomass-Derived Sugars via Co-fermentation of Lactobacillus Brevis and Lactobacillus Plantarum. *Journal of Bioscience and Bioengineering*. 2015. 119, 694-699.

Zhu, X., Tao, Y., Liang, C., Li, X., Wei, N., Zhang, W., Zhou, Y., Yang, Y. and Bo, T., The Synthesis of N-Caproate from Lactate: A New Efficient Process for Medium-Chain Carboxylates Production. *Scientific Reports*. 2015. 5, 14360.

Zhu, X., Zhou, Y., Wang, Y., Wu, T., Li, X., Li, D. and Tao, Y, Production of High-Concentration N-Caproic Acid from Lactate Through Fermentation Using a Newly Isolated Ruminococcaceae Bacterium CPB6. *Biotechnology for Biofuels*. 2017. 10, 102.

Zurawski, J.V., Khatibi, P.A., Akinosho, H.O., Straub, C.T., Compton, S.H., Conway, J.M., Lee, L.L., Ragauskas, A.J., Davison, B.H.M., Adams, M.W.M. and Kelly, R.M., Bioavailability of Carbohydrate Content in Natural and Transgenic Switchgrasses for the Extreme Thermophile Caldicellulosiruptor bescii. *Applied and Environmental Microbiology*. 2017. 83.

U.S. Appl. No. 16/433,639, Timothy James Donohue, Jun. 6, 2019.

\* cited by examiner

MICROBIOMES AND METHODS FOR PRODUCING MEDIUM-CHAIN FATTY ACIDS FROM ORGANIC SUBSTRATES

CROSS-REFERENCE TO RELATED APPLICATIONS

This application is a continuation of U.S. application Ser. No. 16/433,639, filed Jun. 6, 2019, which issued as U.S. Pat. No. 11,242,544 on Feb. 8, 2022, and which claims priority to U.S. Application 62/846,378, filed May 10, 2019, U.S. Application 62/697,249, filed Jul. 12, 2018, and U.S. Application 62/696,677, filed Jul. 11, 2018, each which is incorporated herein by reference in its entirety.

STATEMENT REGARDING FEDERALLY SPONSORED RESEARCH

This invention was made with government support under DE-FC02-07ER64494 and DE-SC0018409 awarded by the US Department of Energy. The government has certain rights in the invention.

SEQUENCE LISTING

The instant application contains a Sequence Listing which has been submitted in ASCII format via EFS-Web and is hereby incorporated by reference in its entirety. The ASCII copy, created on May 16, 2019, is named "USPTO—190606—Pat_App—P170271US05—SEQUENCE_LISTING_ST25.txt" and is 44,306 kilobytes in size.

FIELD OF THE INVENTION

The invention is directed to microbiomes and uses thereof, particularly for producing medium-chain fatty acids from organic substrates.

BACKGROUND

In lignocellulosic biorefining, the non-sugary parts of plants (e.g., corn stover) and dedicated energy crops (e.g., switchgrass, *Miscanthus*, poplar trees) are converted to biofuels by fermentation. To improve the revenue from lignocellulosic biorefining, other valuable chemicals (e.g., specialty chemicals) need to be produced from the cellulosic biomass.

After distilling ethanol and/or other compounds from the fermented hydrolysate, the remaining residue (also known as stillage) contains a high amount of chemical energy, approximately 100,000 mg/L as soluble chemical oxygen demand (sCOD). This amount of chemical energy, comparable in magnitude with the amount of chemical energy recovered as ethanol or other fuel compounds, is in the form of unreacted polysaccharides and sugars, proteins, and other complex plant materials that are not used by the alcohol-producing microorganisms.

In existing processes, lignocellulosic stillage is digested to produce biogas, which is a mixture of methane, carbon-dioxide, and other trace gases. Biogas is combusted in a combined heat and power generation process. A portion of the generated heat and power is used for operating facilities, and excess electricity can be sold. Alternatively, biogas can be converted to natural gas and injected into a natural gas pipeline. Given the high sCOD content of stillage, however, alternative uses for the stillage are possible and are needed to improve the economic and carbon sustainability of new biorefineries.

SUMMARY OF THE INVENTION

The present invention is directed to technology useful for converting the residues from lignocellulosic fuel (e.g., ethanol, isobutanol, etc.) production to valuable medium-chain fatty acids (such as hexanoic and octanoic acids) using an anaerobic microbiome.

The present invention provides microbiomes and methods for converting unreacted chemical components in stillage to valuable medium-chain fatty acids (such as hexanoic and octanoic acids) using a mixture of microbes (e.g., anaerobic microbiome). Operationally, a portion of the stillage stream can be separated and fed to a bioreactor containing the mixture of microbes, which transforms a fraction of the stillage to medium-chain fatty acids. The other fraction of the stillage can be sent on to the anaerobic digester to generate electricity (similar to existing biorefineries).

Exemplary conditions that lead to hexanoic and octanoic acid accumulation include a pH of about 5.5, a reactor temperature of about 35° C., a solids retention time (SRT) of about 6 days, and allowing the desired products to accumulate inside of the bioreactor. Drastic deviations from these parameters can lead to production of lactic acid and acetic acid instead of medium-chain fatty acids.

Hexanoic and octanoic acid are toxic to many microorganisms. In existing processes, these products are removed to prevent inhibition of the producing microorganisms. In preferred versions of the present invention, the acids are allowed to accumulate to saturation levels. This controls the microbiome and prevents the growth of undesired organisms that otherwise would decrease the yield of the acids.

Other processes that recover mixtures of short- and medium-chain fatty acids require the use of chemicals to inhibit the growth of methanogenic organisms. In preferred versions of the present invention, methanogens are eliminated from the microbial community by: (1) originating the community from an inoculum that does not contain methanogens, (2) operating the reactor at a pH that discourages the growth of methanogens, and (3) accumulating the medium-chain fatty acids to near saturation level or to levels that prevent the accumulation of such unwanted microbes.

The present invention provides an alternative use for a portion of the stillage that allows for the production of value-added chemicals while simultaneously allowing for biogas production to fulfill a biorefinery's energy requirements. Technoeconomic analysis shows that converting 16% of the sCOD in the conversion residue (to hexanoic acid (14.5%) and octanoic acid (1.5%), prior to anaerobic digestion) allows for the generation of a product stream (the sum of medium-chain fatty acids and biogas) having approximately 10 times more value than anaerobic digestion alone.

Accordingly, one aspect of the invention is directed to a microbiome composition. The microbiome composition preferably comprises a set of microbes. The microbes in the set preferably consist of members of *Lachnospiraceae, Eubacteriaceae, Coriobacteriaceae,* and *Lactobacillaceae.* The number of individual physical microbes in the set preferably constitute at least 60% of the total number of individual physical microbes in the microbiome composition.

The *Lachnospiraceae* in the set preferably include members of a genus selected from the group consisting of *Roseburia* and *Shuttleworthia*. In some versions, the *Lach-* nospiraceae in the set comprise one or more microbes with a genome comprising a sequence at least 90% identical to at least 1 contiguous kilobase of any one or more of SEQ ID NOS:1-10. The members of *Lachnospiraceae* in the set preferably constitute at least 40% of the total number of individual microbes in the microbiome composition.

The *Eubacteriaceae* in the set preferably include members of *Pseudoramibacter*. In some versions, the *Eubacteriaceae* in the set comprise one or more microbes with a genome comprising a sequence at least 90% identical to at least 1 contiguous kilobase of any one or more of SEQ ID NOS:11-39. The members of *Eubacteriaceae* in the set preferably constitute at least 2% of the total number of individual microbes in the microbiome composition.

The *Coriobacteriaceae* in the set preferably include members of a genus selected from the group consisting of *Olsenella* and *Atopobium*. In some versions, the *Coriobacteriaceae* in the set comprise one or more microbes with a genome comprising a sequence at least 90% identical to at least 1 contiguous kilobase of any one or more of SEQ ID NOS:40-420. The members of *Coriobacteriaceae* in the set preferably constitute at least 3% of the total number of individual microbes in the microbiome composition.

The *Lactobacillaceae* in the set preferably include members of *Lactobacillus*. In some versions, the *Lactobacillaceae* comprise one or more microbes with a genome comprising a sequence at least 90% identical to at least 1 contiguous kilobase of any one or more of SEQ ID NOS: 421-745. The members of *Lactobacillaceae* preferably constitute at least 7% of the total number of individual microbes in the microbiome composition.

In some versions, the number of individual microbes in the set constitutes at least 85% of the total number of individual microbes in the microbiome composition.

In some versions, less than 1% of the number of individual microbes in the microbiome composition are members of *Ethanoligenens, Desulfitobacterium, Clostridium, Propionibacterium, Bifidobacterium, Ruminococcaceae,* and *Bifidobacteriaceae*.

Another aspect of the invention is directed to a method of producing medium-chain fatty acids from an organic substrate. The method preferably comprises anaerobically fermenting the organic substrate for a time sufficient to produce medium-chain fatty acids from the organic substrate with a microbiome composition of the invention. The organic substrate preferably comprises a component selected from the group consisting of xylose, complex carbohydrates, and glycerol. The medium in some versions comprises a lignocellulosic ethanol fermentation residue (lignocellulosic stillage). The fermenting in some versions is performed at a pH of about 5 to about 6.5. In some versions, the fermenting is performed without the addition of ethanol. In some versions, the fermenting does not produce methane.

The objects and advantages of the invention will appear more fully from the following detailed description of the preferred embodiment of the invention made in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 2A) Compounds removed from stillage; (FIG. 2B) production of odd-chain propionic (C3), pentanoic (C5) and heptanoic (C7) acids; (FIG. 2C) production of even-chain acetic (C2), butyric (C4), hexanoic (C6), and octanoic (C8) acids; (FIG. 2D) removal of COD, percent conversion of carbohydrates, and percent conversions of COD to SCFA (C2 to C5) and MCFA (C6 to C8).

DETAILED DESCRIPTION OF THE INVENTION

Figure 1:
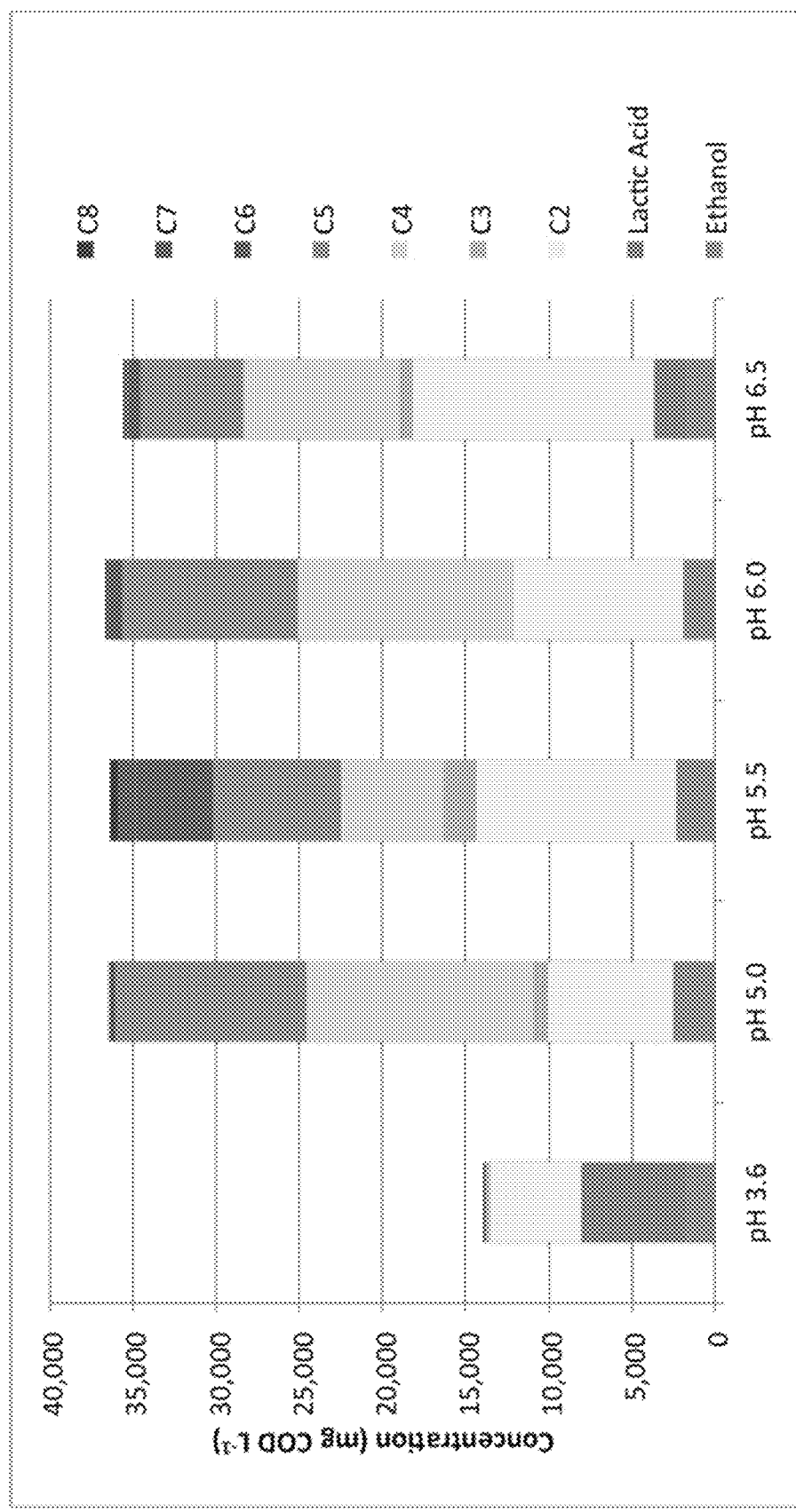
FIG. 1. Chemical analysis for mixed culture fermentations after 6 days under different pH conditions.

The invention is directed to microbiome compositions and methods of using same for producing medium-chain fatty acids from organic substrates.

The microbiome compositions of the invention comprise a set of microbes. The microbes in the set comprise several different types of microbes, and the number of individual physical microbes in the set comprises a certain proportion of the total number of individual physical microbes in the microbiome composition.

In some versions of the invention, the microbes in the set consist of members of *Lachnospiraceae, Eubacteriaceae, Coriobacteriaceae*, and *Lactobacillaceae*.

In some versions, the *Lachnospiraceae* in the set comprise, consist essentially of, or consist of members of a genus selected from the group consisting of *Roseburia* and *Shuttleworthia*.

In some versions, the *Lachnospiraceae* in the set comprise, consist essentially of, or consist of one or more microbes with a genome comprising a sequence at least 10%, at least 15%, at least 20%, at least 25%, at least 30%, at least 35%, at least 40%, at least 45%, at least 50%, least 55%, at least 60%, at least 65%, at least 70%, at least 75%, at least 80%, at least 85%, at least 90%, at least 95% or more identical to at least 0.5 contiguous kilobases, at least 1 contiguous kilobase, at least 2 contiguous kilobases, at least 3 contiguous kilobases, at least 4 contiguous kilobases, at least 5 contiguous kilobases, at least 6 contiguous kilobases, at least 7 contiguous kilobases, at least 8 contiguous kilobases, at least 9 contiguous kilobases, at least 10 contiguous kilobases, at least 11 contiguous kilobases, at least 12 contiguous kilobases, at least 13 contiguous kilobases, at least 14 contiguous kilobases, at least 15 contiguous kilobases, at least 20 contiguous kilobases, at least 25 contiguous kilobases, at least 30 contiguous kilobases, at least 40 contiguous kilobases, at least 50 contiguous kilobases, at least 60 contiguous kilobases, at least 70 contiguous kilobases, at least 80 contiguous kilobases, at least 90 contiguous kilobases, at least 100 contiguous kilobases, at least 110 contiguous kilobases, at least 120 contiguous kilobases, at least 130 contiguous kilobases, at least 140 contiguous kilobases, at least 150 contiguous kilobases, at least 200 contiguous kilobases, at least 300 contiguous kilobases, at least 400 contiguous kilobases, at least 500 contiguous kilobases, at least 600 contiguous kilobases, at least 700 contiguous kilobases, at least 800 contiguous kilobases, at least 900 contiguous kilobases, at least 1,000 contiguous kilobases of, or the entirety of, any one or more of SEQ ID NOS:1-10.

Each microbe corresponding to the LCO1 and LCO1.1 metagenome-assembled genomes provided in the examples is considered herein to be a member of the *Roseburia* and/or *Shuttleworthia* genera of *Lachnospiraceae*.

In some versions, the *Eubacteriaceae* in the set comprise, consist essentially of, or consist of members of *Pseudoramibacter*.

In some versions, the *Eubacteriaceae* in the set comprise, consist essentially of, or consist of one or more microbes with a genome comprising a sequence at least 10%, at least 15%, at least 20%, at least 25%, at least 30%, at least 35%, at least 40%, at least 45%, at least 50%, least 55%, at least 60%, at least 65%, at least 70%, at least 75%, at least 80%, at least 85%, at least 90%, at least 95% or more identical to at least 0.5 contiguous kilobases, at least 1 contiguous kilobase, at least 2 contiguous kilobases, at least 3 contiguous kilobases, at least 4 contiguous kilobases, at least 5 contiguous kilobases, at least 6 contiguous kilobases, at least 7 contiguous kilobases, at least 8 contiguous kilobases, at least 9 contiguous kilobases, at least 10 contiguous kilobases, at least 11 contiguous kilobases, at least 12 contiguous kilobases, at least 13 contiguous kilobases, at least 14 contiguous kilobases, at least 15 contiguous kilobases, at least 20 contiguous kilobases, at least 25 contiguous kilobases, at least 30 contiguous kilobases, at least 40 contiguous kilobases, at least 50 contiguous kilobases, at least 60 contiguous kilobases, at least 70 contiguous kilobases, at least 80 contiguous kilobases, at least 90 contiguous kilobases, at least 100 contiguous kilobases, at least 110 contiguous kilobases, at least 120 contiguous kilobases, at least 130 contiguous kilobases, at least 140 contiguous kilobases, at least 150 contiguous kilobases, at least 200 contiguous kilobases, at least 300 contiguous kilobases, at least 400 contiguous kilobases, at least 500 contiguous kilobases, at least 600 contiguous kilobases, at least 700 contiguous kilobases, at least 800 contiguous kilobases, at least 900 contiguous kilobases, at least 1,000 contiguous kilobases of, or the entirety of, any one or more of SEQ ID NOS:11-39.

Each microbe corresponding to the EUB1 and EUB1.1 metagenome-assembled genomes provided in the examples is considered herein to be a member of the *Pseudoramibacter* genus of *Eubacteriaceae*.

In some versions, the *Coriobacteriaceae* in the set comprise, consist essentially of, or consist of members of a genus selected from the group consisting of *Olsenella* and *Atopobium*.

In some versions, the *Coriobacteriaceae* in the set comprise, consist essentially of, or consist of one or more microbes with a genome comprising a sequence at least 10%, at least 15%, at least 20%, at least 25%, at least 30%, at least 35%, at least 40%, at least 45%, at least 50%, least 55%, at least 60%, at least 65%, at least 70%, at least 75%, at least 80%, at least 85%, at least 90%, at least 95% or more identical to at least 0.5 contiguous kilobases, at least 1 contiguous kilobase, at least 2 contiguous kilobases, at least 3 contiguous kilobases, at least 4 contiguous kilobases, at least 5 contiguous kilobases, at least 6 contiguous kilobases, at least 7 contiguous kilobases, at least 8 contiguous kilobases, at least 9 contiguous kilobases, at least 10 contiguous kilobases, at least 11 contiguous kilobases, at least 12 contiguous kilobases, at least 13 contiguous kilobases, at least 14 contiguous kilobases, at least 15 contiguous kilobases, at least 20 contiguous kilobases, at least 25 contiguous kilobases, at least 30 contiguous kilobases, at least 40 contiguous kilobases, at least 50 contiguous kilobases, at least 60 contiguous kilobases, at least 70 contiguous kilobases, at least 80 contiguous kilobases, at least 90 contiguous kilobases, at least 100 contiguous kilobases, at least 110 contiguous kilobases, at least 120 contiguous kilobases, at least 130 contiguous kilobases, at least 140 contiguous kilobases, at least 150 contiguous kilobases, at least 200 contiguous kilobases, at least 300 contiguous kilobases, at least 400 contiguous kilobases, at least 500 contiguous kilobases, at least 600 contiguous kilobases, at least 700 contiguous kilobases, at least 800 contiguous kilobases, at least 900 contiguous kilobases, at least 1,000 contiguous kilobases of, or the entirety of, any one or more of SEQ ID NOS:40-420.

Each microbe corresponding to the COR1, COR2, COR3, COR1.1, COR3.1, and COR4.1 metagenome-assembled genomes provided in the examples is considered herein to be a member of the *Olsenella* and/or *Atopobium* genera of *Coriobacteriaceae*.

In some versions, the *Lactobacillaceae* in the set comprise, consist essentially of, or consist of members of *Lactobacillus*.

In some versions, *Lactobacillaceae* in the set comprise, consist essentially of, or consist of one or more microbes with a genome comprising a sequence at least 10%, at least 15%, at least 20%, at least 25%, at least 30%, at least 35%, at least 40%, at least 45%, at least 50%, least 55%, at least 60%, at least 65%, at least 70%, at least 75%, at least 80%, at least 85%, at least 90%, at least 95% or more identical to at least 0.5 contiguous kilobases, at least 1 contiguous kilobase, at least 2 contiguous kilobases, at least 3 contiguous kilobases, at least 4 contiguous kilobases, at least 5 contiguous kilobases, at least 6 contiguous kilobases, at least 7 contiguous kilobases, at least 8 contiguous kilobases, at least 9 contiguous kilobases, at least 10 contiguous kilobases, at least 11 contiguous kilobases, at least 12 contiguous kilobases, at least 13 contiguous kilobases, at least 14 contiguous kilobases, at least 15 contiguous kilobases, at least 20 contiguous kilobases, at least 25 contiguous kilobases, at least 30 contiguous kilobases, at least 40 contiguous kilobases, at least 50 contiguous kilobases, at least 60 contiguous kilobases, at least 70 contiguous kilobases, at least 80 contiguous kilobases, at least 90 contiguous kilobases, at least 100 contiguous kilobases, at least 110 contiguous kilobases, at least 120 contiguous kilobases, at least 130 contiguous kilobases, at least 140 contiguous kilobases, at least 150 contiguous kilobases, at least 200 contiguous kilobases, at least 300 contiguous kilobases, at least 400 contiguous kilobases, at least 500 contiguous kilobases, at least 600 contiguous kilobases, at least 700 contiguous kilobases, at least 800 contiguous kilobases, at least 900 contiguous kilobases, at least 1,000 contiguous kilobases of, or the entirety of, any one or more of SEQ ID NOS:421-745.

Each microbe corresponding to the LAC1, LAC2, LAC3, LAC4, LAC5, LAC1.1, LAC2.1, LAC4.1, LAC5.1, LAC6.1, and LAC7.1 metagenome-assembled genomes provided in the examples is considered herein to be a member of the *Lactobacillus* genus of *Lactobacillaceae*.

The sequences corresponding to the SEQ ID NOs provided herein are the sequences of the metagenome-assembled genomes of exemplary microorganisms of the invention. A correspondence between the SEQ ID NOs and the metagenome-assembled genomes is shown in Table 1.

TABLE 1

Sequences of metagenome-assembled genomes (MAGs).

| MAG | NO. OF SEQUENCES | SEQ ID NOS |
| --- | --- | --- |
| LCO1.1 | 10 | 1-10 |
| EUB1.1 | 29 | 11-39 |
| COR1.1 | 82 | 40-121 |
| COR2 | 157 | 122-278 |
| COR3.1 | 134 | 279-412 |
| COR4.1 | 8 | 413-420 |
| LAC1.1 | 9 | 421-429 |
| LAC2.1 | 37 | 430-466 |
| LAC3 | 175 | 467-641 |
| LAC4.1 | 53 | 642-694 |
| LAC5.1 | 6 | 695-700 |
| LAC6.1 | 12 | 701-712 |
| LAC7.1 | 33 | 713-745 |

The metagenome-assembled genome sequences for LCO1.1, EUB1.1, COR1.1, COR3.1, LAC1.1, LAC2.1, LAC4.1, and LAC5.1 encompass the metagenome-assembled genome sequences for LCO1, EUB1, COR1, COR3, LAC1, LAC2, LAC4, and LAC5 of the examples, respectively.

The terms "percent sequence identity" or "percent identical" are used interchangeably with respect to two polynucleotide sequences and refer to the percentage of bases that are identical in the two sequences when the sequences are optimally aligned. Thus, 80% amino acid sequence identity means that 80% of the amino acids in two optimally aligned polypeptide sequences are identical.

The term "identical," in the context of two polynucleotide sequences, means that the bases in the two sequences are the same when aligned for maximum correspondence, as measured using a sequence comparison or analysis algorithm such as those described herein. For example, if when properly aligned, the corresponding segments of two sequences have identical residues at 5 positions out of 10, it is said that the two sequences have a 50% identity or are 50% identical. Most bioinformatic programs report percent identity over aligned sequence regions, which are typically not the entire molecules. If an alignment is long enough and contains enough identical residues, an expectation value can be calculated, which indicates that the level of identity in the alignment is unlikely to occur by random chance.

The term "alignment" refers to a method of comparing two or more sequences for the purpose of determining their relationship to each other. Alignments are typically performed by computer programs that apply various algorithms, however it is also possible to perform an alignment by hand. Alignment programs typically iterate through potential alignments of sequences and score the alignments using substitution tables, employing a variety of strategies to reach a potential optimal alignment score. Commonly-used alignment algorithms include, but are not limited to, CLUSTALW, (see, Thompson J. D., Higgins D. G., Gibson T. J., CLUSTAL W: improving the sensitivity of progressive multiple sequence alignment through sequence weighting, position-specific gap penalties and weight matrix choice, Nucleic Acids Research 22: 4673-4680, 1994); CLUSTALV, (see, Larkin M. A., et al., CLUSTALW2, ClustalW and ClustalX version 2, Bioinformatics 23(21): 2947-2948, 2007); Jotun-Hein, Muscle et al., MUSCLE: a multiple sequence alignment method with reduced time and space complexity, BMC Bioinformatics 5: 113, 2004); Mafft, Kalign, ProbCons, and T-Coffee (see Notredame et al., T-Coffee: A novel method for multiple sequence alignments, Journal of Molecular Biology 302: 205-217, 2000). Exemplary programs that implement one or more of the above algorithms include, but are not limited to MegAlign from DNAStar (DNAStar, Inc. 3801 Regent St. Madison, Wis. 53705), MUSCLE, T-Coffee, CLUSTALX, CLUSTALV, JalView, Phylip, and Discovery Studio from Accelrys (Accelrys, Inc., 10188 Telesis Ct, Suite 100, San Diego, Calif. 92121). In a non-limiting example, MegAlign is used to implement the CLUSTALW alignment algorithm with the following parameters: Gap Penalty 10, Gap Length Penalty 0.20, Delay Divergent Seqs (30%) DNA Transition Weight 0.50, Protein Weight matrix Gonnet Series, DNA Weight Matrix IUB.

Sequence alignment and the determination of sequence identity in some versions can be performed as described in U.S. Pat. No. 9,708,630, which is incorporated herein by reference.

In some versions of the invention, the number of individual physical microbes in the set constitutes at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more of the total number of individual physical microbes in the microbiome composition.

In some versions, the members of *Lachnospiraceae* in the set constitute at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more of the total number of individual physical microbes in the microbiome composition. In some versions, the members of *Lachnospiraceae* in the set constitute up to 5%, up to 6%, up to 7%, up to 8%, up to 9%, up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95% or more of the total number of individual physical microbes in the microbiome composition.

In some versions, the members of *Eubacteriaceae* in the set constitute at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50% at least 55%, at least 60%, at least 65%, at least 70%, at least 75%, at least 80%, at least 85%, at least 90%, at least 95% or more of the total number of individual physical microbes in the microbiome composition. In some versions, the members of *Eubacteriaceae* in the set constitute up to 1%, up to 2%, up to 3%, up to 4%, up to 5%, up to 6%, up to 7%, up to 8%, up to 9%, up to 10%, up to 15%, up to 20%, up to 25%, up to 30%, up to 35%, up to 40%, up to 45%, up to 55%, up to 60%, up to 65%, up to 70%, up to 75%, up to 80%, up to 85%, up to 90%, up to 95% or more of the total number of individual physical microbes in the microbiome composition.

In some versions, the members of *Coriobacteriaceae* in the set constitute at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50% at least 55%, at least 60%, at least 65%, at least 70%, at least 75%, at least 80%, at least 85%, at least 90%, at least 95% or more of the total number of individual physical microbes in the microbiome composition. In some versions, the members of *Coriobacteriaceae* in the set constitute up to 1%, up to 2%, up to 3%, up to 4%, up to 5%, up to 6%, up to 7%, up to 8%, up to 9%, up to 10%, up to 15%, up to 20%, up to 25%, up to 30%, up to 35%, up to 40%, up to 45%, up to 55%, up to 60%, up to 65%, up to 70%, up to 75%, up to 80%, up to 85%, up to 90%, up to 95% or more of the total number of individual physical microbes in the microbiome composition.

In some versions, the members of *Lactobacillaceae* in the set constitute at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more of the total number of individual physical microbes in the microbiome composition. In some versions, the members of *Lactobacillaceae* in the set constitute up to 5%, up to 6%, up to 7%, up to 8%, up to 9%, up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95% or more of the total number of individual physical microbes in the microbiome composition.

In some versions, 0% or less than 0.1%, less than 0.2%, less than 0.3%, less than 0.4%, less than 0.5%, less than 0.6%, less than 0.7%, less than 0.8%, less than 0.9%, less than 1%, less than 2%, less than 3%, less than 4%, or less than 5%, of the number of individual physical microbes in the microbiome composition are methanogens.

In some versions, 0% or less than 0.1%, less than 0.2%, less than 0.3%, less than 0.4%, less than 0.5%, less than 0.6%, less than 0.7%, less than 0.8%, less than 0.9%, less than 1%, less than 2%, less than 3%, less than 4%, or less than 5%, of the number of individual physical microbes in the microbiome composition are members of *Ethanoligenens, Desulfitobacterium, Clostridium, Propionibacterium, Bifidobacterium, Ruminococcaceae,* and/or *Bifidobacteriaceae.*

The relative abundance of the number of individual physical microbes in the set with respect to the total number of individual physical microbes in the microbiome composition can be determined by quantitating operational taxonomic units (OTUs) or metagenome-assembled genomes (MAGs), as described in the following examples.

The methods of the invention comprise methods of producing medium-chain fatty acids from an organic substrate. Steps in the methods include anaerobically fermenting a microbiome composition as described herein in a medium comprising the organic substrate for a time sufficient to produce medium-chain fatty acids from the organic substrate. "Medium-chain fatty acids" refers to C6 to C12 fatty acids. "Organic substrate" refers to organic matter contributing to a positive chemical oxygen demand (COD) value.

In some versions, the organic feedstock comprises a component selected from the group consisting of xylose, complex carbohydrates, and glycerol. Other organic matter may also be present, including xylose, pyruvate, xylitol, succinate, lactate, formate, acetate, butyrate, hexanoate, octanoate, propionate (propanoate), valerate, heptanoate, 2-methyl propanoic acid, 3-methyl butanoic acid, 4-methyl pentanoic acid, ethanol, proteins, and aromatic compounds such as vanillamide, 4-hydroxybenzyl alcohol, syringamide, coumaryl amide, 4-hydroxybenzoic acid, feruloyl amide, vanillic acid, p-coumaric acid, ferulic acid, and benzoic acid.

The xylose may be present in the medium in an amount (measured as chemical oxygen demand (COD)) of at least 1%, at least 5%, at least 10%, at least 15%, at least 20%, at least 25%, at least 30%, at least 35%, at least 40%, at least 45%, at least 50% at least 55%, at least 60%, at least 65%, at least 70%, at least 75% or more and up to 5%, up to 10%, up to 15%, up to 20%, up to 25%, up to 30%, up to 35%, up to 40%, up to 45%, up to 55%, up to 60%, up to 65%, up to 70%, up to 75%, up to 80%, up to 85%, up to 90% or more of the COD in the medium.

The complex carbohydrates may be present in the medium in an amount (measured as chemical oxygen demand (COD)) of at least 1%, at least 5%, at least 10%, at least 15%, at least 20%, at least 25%, at least 30%, at least 35%, at least 40%, at least 45%, at least 50% at least 55%, at least 60%, at least 65%, at least 70%, at least 75% or more and up to 5%, up to 10%, up to 15%, up to 20%, up to 25%, up to 30%, up to 35%, up to 40%, up to 45%, up to 55%, up to 60%, up to 65%, up to 70%, up to 75%, up to 80%, up to 85%, up to 90% or more of the COD in the medium.

The glycerol may be present in the medium in an amount (measured as chemical oxygen demand (COD)) of at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50% at least 55%, at least 60%, at least 65%, at least 70%, at least 75% or more and up to 5%, up to 10%, up to 15%, up to 20%, up to 25%, up to 30%, up to 35%, up to 40%, up to 45%, up to 55%, up to 60%, up to 65%, up to 70%, up to 75%, up to 80%, up to 85%, up to 90% or more of the COD in the medium.

In some versions, total soluble carbohydrates are present in the medium in an amount of from about 2,000 mg COD/L to about 50,000 mg COD/L. Amounts above and below these values are acceptable.

In some versions, total soluble proteins are present in the medium in an amount of from about 500 mg COD/L to about 5,000 mg COD/L. Amounts above and below these values are acceptable.

In some versions, vanillamide is present in the medium in an amount of from about 40 µg COD/L to about 4000 µg COD/L, such as about 300 µg COD/L to about 500 µg COD/L. Amounts above and below these values are acceptable.

In some versions, 4-hydroxybenzyl alcohol is present in the medium in an amount of from about 20 µg COD/L to about 2000 µg COD/L, such as about 90 µg COD/L to about 400 µg COD/L. Amounts above and below these values are acceptable.

In some versions, syringamide is present in the medium in an amount of from about 20 µg COD/L to about 2000 µg COD/L, such as about 90 µg COD/L to about 400 µg COD/L. Amounts above and below these values are acceptable.

In some versions, coumaryl amide is present in the medium in an amount of from about 500 µg COD/L to about 100,000 µg COD/L, such as about 1000 µg COD/L to about 20,000 µg COD/L. Amounts above and below these values are acceptable.

In some versions, 4-hydroxybenzoic acid is present in the medium in an amount of from about 30 µg COD/L to about 3000 µg COD/L, such as about 200 µg COD/L to about 400 µg COD/L. Amounts above and below these values are acceptable.

In some versions, feryloyl amide is present in the medium in an amount of from about 300 µg COD/L to about 100,000 µg COD/L, such as about 1000 µg COD/L to about 15,000 µg COD/L. Amounts above and below these values are acceptable.

In some versions, vanillic acid is present in the medium in an amount of from about 30 µg COD/L to about 3,000 µg COD/L, such as about 100 µg COD/L to about 600 µg COD/L. Amounts above and below these values are acceptable.

In some versions, p-coumaric acid is present in the medium in an amount of from about 10 µg COD/L to about 30,000 µg COD/L, such as about 500 µg COD/L to about 5,000 µg COD/L. Amounts above and below these values are acceptable.

In some versions, ferulic acid is present in the medium in an amount of from about 10 µg COD/L to about 2,500 µg COD/L, such as about 50 µg COD/L to about 500 µg COD/L. Amounts above and below these values are acceptable.

In some versions, benzoic acid is present in the medium in an amount of from about 100 µg COD/L to about 20,000 µg COD/L, such as about 500 µg COD/L to about 3,000 µg COD/L. Amounts above and below these values are acceptable.

In some versions, glucose is absent from the medium or is present in the medium in an amount (measured as chemical oxygen demand (COD)) less than 30%, less than 25%, less than 20%, less than 15%, less than 10%, less than 5%, less than 2.5%, less than 1%, less than 0.5%, less than 0.1%, or less than 0.01% of the COD in the medium.

In some versions, the medium comprises or is a lignocellulosic stillage. The lignocellulosic stillage may comprise stillage resulting from distillation of ethanol or other components from fermented lignocellulosic biomass hydrolysate.

In some versions, the fermenting is performed at a pH of about 5 to about 6, such as a pH of about 5.5.

In some versions, the fermenting is performed at a temperature from about 10° C. to about 60° C., such as from about 15° C. to about 55° C., from about 20° C. to about 50° C., from about 25° C. to about 45° C., from about 30° C. to about 40° C., or about 35° C.

In some versions, the fermenting is performed at a solids retention time (SRT) of from about 1 day to about 12 days, such as from about 2 days to about 11 days, from about 3 days to about 10 days, from about 3 days to about 9 days, from about 4 days to about 8 days, from about 5 days to about 7 days, or about 6 days.

In some versions, the fermenting is performed without the addition of ethanol. In some versions, the fermenting does not produce methane. In some versions, the medium-chain fatty acids are not removed during the fermenting and are accumulated in the medium to near saturating levels.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

U.S. Application 62/846,378, filed May 10, 2019; U.S. Application 62/697,249, filed Jul. 12, 2018; U.S. Application 62/696,677, filed Jul. 11, 2018; Scarborough and Lynch et al. 2018 (Carborough M J, Lynch G, Dickson M, McGee M, Donohue T J, Noguera D R. Increasing the economic value of lignocellulosic stillage through medium-chain fatty acid production. *Biotechnol Biofuels.* 2018 Jul. 19; 11:200. doi: 10.1186/s13068-018-1193-x. eCollection 2018.); and Scarborough and Lawson et al. 2018 (Scarborough M J, Lawson C E, Hamilton J J, Donohue T J, Noguera D R. Metatranscriptomic and Thermodynamic Insights into Medium-Chain Fatty Acid Production Using an Anaerobic Microbiome. *mSystems.* 2018 Nov. 20; 3(6). pii: e00221-18. doi: 10.1128/mSystems.00221-18. eCollection 2018 November-December) are specifically incorporated by reference in their entireties.

It is understood that the invention is not confined to the particular construction and arrangement of parts herein illustrated and described, but embraces such modified forms thereof as come within the scope of the claims.

EXAMPLES

Increasing the Economic Value of Lignocellulosic Stillage Through Medium-Chain Fatty Acid Production Summary Lignocellulosic biomass is seen as an abundant renewable source of liquid fuels and chemicals that are currently derived from petroleum. When lignocellulosic biomass is used for ethanol production, the resulting liquid residue (stillage) contains large amounts of organic material that could be further transformed into recoverable bioproducts, thus enhancing the economics of the biorefinery.

Here we test the hypothesis that a bacterial community could transform the organics in stillage into valuable bioproducts. We demonstrate the ability of this microbiome to convert stillage organics into medium-chain fatty acids (MCFAs), identify the predominant community members, and perform a technoeconomic analysis of recovering MCFAs as a co-product of ethanol production. Steady-state operation of a stillage-fed bioreactor showed that 18% of the organic matter in stillage was converted to MCFAs. Xylose and complex carbohydrates were the primary substrates transformed. During the MCFA production period, the five major genera represented more than 95% of the community, including *Lactobacillus, Roseburia, Atopobium, Olsenella,* and *Pseudoramibacter.* To assess the potential benefits of producing MCFA from stillage, we modeled the economics of ethanol and MCFA co-production, at MCFA productivities observed during reactor operation.

The analysis predicts that production of MCFA, ethanol, and electricity could reduce the minimum ethanol selling price from $2.15 gal$^{-1}$ to $1.76 gal$^{-1}$ ($2.68 gal$^{-1}$ gasoline equivalents) when compared to a lignocellulosic biorefinery that produces only ethanol and electricity.

Background

The production of food, fuels, pharmaceuticals and many chemicals depends on microbial fermentations. When one considers the sum of microbial biomass, excreted metabolic end-products, and non-metabolized nutrients, there is considerable residual organic matter in the liquid residue (stillage) remaining after distillation. One common co-product of ethanol production is biogas, which is generated by anaerobic digestion of stillage. Combusting lignin and biogas creates heat and power used to operate the biorefinery, and any excess electricity can be sold as a co-product.[1] In a techno-economic analysis (TEA) conducted by the National Renewable Energy Laboratory (NREL), a 61 million gallon per year lignocellulosic ethanol biorefinery produced fuel at a price of $2.15 gal$^{-1}$ ($3.27 gal$^{-1}$ gasoline-equivalents) and electricity worth $6.57 million yr$^{-1}$.[2]

The Renewable Fuel Standards (RFS), created by the Energy Policy Act of 2005 and expanded by the Energy Independence and Security Act of 2007, set production goals for many renewable energy sources, including lignocellulosic-derived ethanol.[3,4] While several lignocellulosic biorefineries have opened, total lignocellulosic ethanol production in the United States remains short of original targets. The high costs of obtaining biomass and producing enzymes to hydrolyze biomass are cited as barriers to achieving an acceptable level of profitability for lignocellulosic biorefineries.[2]

One way to potentially improve the economics of lignocellulosic fuel production is to produce valuable co-products, such as medium-chain fatty acids (MCFAs), from stillage. MCFAs are monocarboxylic acids containing six to twelve carbon atoms and are utilized for the production of rubbers, dyes, pharmaceuticals, and antimicrobials.[5] They can also be used as precursors for chemicals currently derived from fossil fuels.[6] In addition to being valuable, MCFAs also have decreased solubility compared to short-chain fatty acids (SCFAs), which should allow for easier extraction from an aqueous medium.

In this example, we investigated the valorization of switchgrass-derived stillage to MCFAs. Switchgrass has been identified as a promising feedstock for biofuel production that can be cultivated on marginal lands.[7] In this example, we tested the ability of using mixed culture anaerobic fermentation, as in the so-called carboxylate platform,[8,9] to valorize stillage to MCFAs. Here total MCFA is the sum of hexanoate and octanoate since it is still largely unknown how to direct metabolism to production of only one MCFA.

In several past studies, ethanol has been used as an electron donor to drive MCFA production from either added acetate or acetate produced by the community as a fermentation intermediate.[10-13] Conversion of lactic acid to MCFAs has also been investigated.[14,15] Recently, a pure culture of *Megasphaera elsdenii* was used to convert glucose in lignocellulosic hydrolysate to MCFAs.[16] Stillage from corn-derived ethanol has also been used to produce MCFAs.[17] Andersen et. al used a mixture of lignocellulosic stillage and dilute ethanol to produce MCFAs at titers greater than their solubility concentrations.[18] However, MCFA production from industrial streams having minimal amounts of glucose or ethanol remains largely unexplored. In addition, there is no published TEA investigating production of MCFAs from stillage.

While past studies have investigated MCFA production from lignocellulosic materials, none have evaluated production of ethanol followed by MCFA production from the resulting stillage in a biorefinery. Thus, the objectives of this example are to (1) test the hypothesis that a stillage-fed microbial community can sustain production of MCFAs; (2) investigate the stability of the microbiome and potential roles of abundant community members in the MCFA-producing reactor; and (3) evaluate the technoeconomics of producing MCFAs from ethanol stillage. To achieve the third objective, we modeled a modified lignocellulosic biorefinery producing MCFA as a co-product to ethanol and electricity (see Scarborough and Lynch et al. 2018, which is incorporated herein by reference, at FIG. 2.1). After accounting for the amount of organic matter in stillage that is directed to MCFA production, the reduction in overall biogas and electricity production, and the increased capital and operational costs associated with MCFA production, our data predict that the potential revenue from producing MCFAs at levels observed in this example would have a positive impact on the economics of lignocellulosic biorefining.

Methods

Switchgrass stillage production. Shawnee switchgrass, grown in 2010 at the Arlington Agricultural Research Center in Wisconsin, USA, was used as the biomass source for this example. Switchgrass was treated using ammonia-fiber expansion (AFEX), enzymatically hydrolyzed, and fermented, as described previously.[19] During processing, hydrolysate is filtered to remove insoluble components, including insoluble lignin. Past work has demonstrated that switchgrass hydrolysates generated with this process contain sufficient nutrients and trace elements to sustain microbial growth[19]. Ethanol fermentations of switchgrass hydrolysate were performed with *Saccharomyces cerevisiae* Y128, an engineered yeast strain with improved xylose utilization and lignotoxin tolerance.[20] Ethanol was removed post-fermentation using a glass distillation apparatus consisting of a 1 L boiling flask, heating mantle, distillation column, and condenser. During distillation, the fermented hydrolysate was heated to approximately 100° C. to maintain a distillation neck temperature of 78° C. Therefore, the distillation process not only removed ethanol but also sterilized the stillage. The stillage remaining after distillation was stored at 4° C. until fed to the bioreactor.

Mixed culture fermentation bioreactor. A mixed culture fermentation bioreactor was inoculated with sludge from an acid-phase digester at the Nine Springs Wastewater Treatment Plant in Madison, Wisconsin. The bench-scale reactor consisted of a vessel with a 150 mL working volume that was continuously stirred at 150 rpm with a magnetic stir bar and maintained at 35° C. using a water bath. The reactor was sealed with a rubber stopper and vented so that any gas produced was released to the atmosphere. For all experiments, the solids retention time (SRT) is equal to the hydraulic retention time.

Initially, we conducted short-term (6 day) experiments to assess if microbial growth could be sustained in stillage and to determine the primary fermentation end products under different pH conditions. For these initial experiments, the pH was either uncontrolled or controlled at set-points of 5.0, 5.5, 6.0, or 6.5 with 5M KOH. A hydraulic retention time of two days was utilized for these initial experiments by pumping 75 mL day$^{-1}$ (3.13 mL hr$^{-1}$) both into and out of the reactor. A shorter SRT was utilized to allow for fast turn-over and stabilization of the microbial community. While this short SRT resulted in production of MCFA, we elected to increase the SRT for a long-term experiment in an attempt to improve overall MCFA titers. For the long-term (252 day) sustained experiment, the pH was controlled at a set-point of 5.50 with 5M KOH and the SRT was controlled at 6 days by pumping 25 mL day$^{-1}$ (1.04 mL hr$^{-1}$) into and out of the reactor.

Chemical analyses. We collected samples from the reactor and stillage for chemical analyses. All samples were filtered using 0.22 μm syringe filters (ThermoFisher Scientific SLGP033RS, Waltham, MA, USA). Soluble chemical oxygen demand (COD) analysis was performed using High Range COD Digestion Vials (Hach 2125915, Loveland, CO, USA) per standard methods.[21] Soluble carbohydrates were measured with the anthrone method.[22] Total soluble proteins were measured with the bicinchoninic acid assay using the Pierce™ BCA Assay Kit (ThermoFisher Scientific 23225, Waltham, MA, USA) and the Compat-Able™ Protein Assay Preparation Reagent Set (ThermoFisher Scientific 23215, Waltham, MA, USA).[23]

Glucose, xylose, acetic acid, formic acid, lactic acid, succinic acid, pyruvic acid, glycerol and xylitol were analyzed with high performance liquid chromatography (HPLC) and quantified with an Agilent 1260 Infinity refractive index detector (Agilent Technologies, Inc. Palo Alto, CA) using a 300×7.8 mm Bio-Rad Aminex HPX-87H column with Cation-H guard (BioRad, Inc., Hercules, CA). A column temperature of 50° C. was used, and 0.02 N $H_2SO_4$ was used for the mobile phase with a flow rate of 0.50 mL min$^{-1}$.

Acetamide, ethanol, n-propionic acid, n-butyric acid, iso-butyric acid, n-pentanoic acid, iso-pentanoic acid, n-hexanoic acid, iso-hexanoic acid, n-heptanoic acid, and n-octanoic acid were analyzed with tandem gas chromatography-mass spectrometry (GC-MS). An Agilent 7890A GC system (Agilent Technologies, Inc. Palo Alto, CA) with a 0.25 mm Restek Stabilwax DA 30 column (Restek 11008, Belefonte, PA) was used. The GC-MS system was equipped with a Gerstel MPS2 (Gerstel, Inc. Baltimore, MD) auto sampler and a solid-phase micro-extraction gray hub fiber assembly (Supelco, Bellefonte, PA). The MS detector was a Pegasus 4D TOF-MS (Leco Corp., Saint Joseph, MI). Stable isotope labeled internal standards were used for each of the analytes measured with GC-MS.

Aromatic compounds were analyzed with liquid chromatography-tandem mass spectrophotometry (LC-MS/MS). For LC-MS/MS analyses. An Ultimate HPG-3400RS pump and WPS-3000RS auto sampler (Thermo Fisher) were mated to an ACQUITY UPLC HSS T3 reversed phase column (2.1×150 mm, 1.8 μm particle diameter, Waters Corporation) with a guard cartridge. Gradient elution was performed at 0.400 mL/min. The LC system was coupled to a TSQ Quantiva Triple Quadrupole mass spectrometer (Thermo Scientific). The Ion Transfer Tub Temp was kept at 350° C. as was the vaporizer temperature. Analytes measured with LC-MS/MS included vanillamide, 4-hydroxybenzyl alcohol, syringamide, coumaryl amide, 4-hydroxybenzoic acid, feruloyl amide, vanillic acid, p-coumaric acid, ferulic acid, and benzoic acid. Detailed chemical analysis data is provided in Scarborough and Lynch et al. 2018, which is incorporated herein by reference, at Additional File 1.

Microbial community analysis. Amplification and sequencing of the V3-V4 region of the 16S rRNA gene was performed to classify and determine the relative abundance of bacteria in the reactor. For the initial short term (six day) experiments, biomass samples were collected from the inoculum acid digester sludge and from the reactor every two days for six days. For the long-term (252 day) experiment, biomass samples were collected from the inoculum acid digester sludge, and from the reactor at Days 2, 4, and 6, and then every six days for the duration of the experiment. Biomass was harvested by centrifuging samples at a relative centrifugal force of 10,000 g for 10 minutes and decanting supernatant. Biomass was then stored at −80° C. until DNA extraction was performed.

DNA was extracted using a Power Soil® DNA Isolation Kit (MoBIO Laboratories 12888, Carlsbad, CA). The purity of extracted DNA was analyzed using a NanoDrop spectrophotometer (Thermo Fisher Scientific ND-2000, Waltham, MA), and DNA was quantified using a Qubit 3.0 (Thermo Fisher Scientific Q33126, Waltham, MA). The V3 and V4 regions of the 16S rRNA gene were amplified using the primer set S-D-Bact-0341-b-S-17/S-D-Bact-1061-a-A-17 as described by Klindworth et al.[24] Amplicons were sequenced on an Illumina MiSeq sequencer (Illumina, San Diego, CA) using pair-end 250 base pair kits at the University of Wisconsin-Madison Biotechnology Center.

Paired-end reads were merged with Fast Length Adjustment of Short Reads (FLASH) using default parameters.[25] The merged reads were analyzed with the Qiime pipeline, utilizing the split libraries command to remove low quality sequences.[26] Sequences were clustered into operational taxonomic units (OTUs) using uclust.[27] Sequences were aligned with PyNast, and chimera detection was performed with ChimeraSlayer.[28,29] Singleton OTUs were removed, and the samples were rarefied to an equal depth, with 130,000 sequences retained for the long-term (252 day) reactor experiment and 45,000 sequences retained for the short-term (6 day) reactor experiments. A representative sequence for each OTU was taxonomically classified using the SILVA database.[30] Tables of OTUs with taxonomic assignments are provided in Scarborough and Lynch et al. 2018, which is incorporated herein by reference, at Additional File 2. The Phyloseq package version 1.14.0 was used for data visualization, and heat maps were generated with the superheat package.[31,32] To construct phylogenetic trees, multiple sequence alignments were performed using MUSCLE, and maximum likelihood phylogenetic trees were constructed with RAxML using the GTRGAMMA method with 1,000 bootstraps.[33, 34]

Statistical analysis of microbial community data was performed using multivariate repeated measures ANOVA with the nlme package in R to generate generalized least squares models in which time was correlated to all predictor variables using the corAR1 structure.[35] Redundancy analysis was also performed using the rda command in the vegan package.[36] Environmental factors were iteratively selected until all were statistically significant (p<0.1) based on 999 model permutations.

Technoeconomic analysis. To estimate the economic impact of producing MCFA from ethanol stillage, a TEA was performed based on information provided in the National Renewable Energy Laboratory (NREL) TEA for a 61 million gallon per year lignocellulosic ethanol facility.[2] We assumed that switchgrass has a similar feedstock cost to corn stover ($58.50 U.S. dry ton$^{-1}$), which is within the range of costs assumed for switchgrass feedstock in other studies.[37,38] Instead of assuming all stillage undergoes anaerobic digestion, we assumed that a portion of the organic matter was converted to organic acids using data obtained in this example, then simulated the extraction of hexanoic and octanoic acids with ASPEN (AspenTech, Bedford, MA) to select an organic solvent and determine process separation efficiencies, heating demands, and sizes for reactors and equipment. We selected 2-octanol as the solvent for liquid-liquid extraction due to the high extraction efficiencies predicted with ASPEN. We assumed that the organic matter in the aqueous phase that remains after extracting the MCFA was fed to the anaerobic digester to produce biogas. The specific methane yield (g methane produced per g COD consumed) and biosolids yield (g biomass produced per g COD consumed) were assumed to be the same as in the NREL TEA.[2] The efficiency of combined heat and power generation by combusting biogas, lignin, and biosolids was also assumed to have the same efficiency as the NREL TEA, with a total of 21% of the energy in the combusted material converted to usable heat and power.[2]

The costs for additional reactors and distillation columns were estimated by scaling related costs presented in the NREL TEA.[2] Costs for the liquid-liquid extraction were determined based on the volumetric flow rate and equations available in Seider et al.[39] The KOH usage was calculated based on experimental reactor data. The 2-octanol demand (2-octanol lost to the aqueous phase) was based on modeling the liquid-liquid extraction with ASPEN. Prices for hexanoic acid, octanoic acid and 2-octanol were obtained from Zauba for imported quantities greater than 1,000 kg in 2016 (see Scarborough and Lynch et al. 2018, which is incorporated herein by reference, at Additional File 3).[40] For consistency with past reporting, all costs and profits are reported in 2007 United States Dollars (USD). To convert from 2016 to 2007 USD, cost indices from the St. Louis Federal Reserve were used.[41] Electricity prices from the NREL TEA were used.[2] A 30-year cash flow was calculated using the cash-flow calculation tool available with the NREL TEA,[42] and the minimum ethanol selling price (MESP) was determined by setting the net present value to zero based on a target 10% internal rate of return, consistent with the NREL TEA.[2] Detailed information related to the TEA is provided in Scarborough and Lynch et al. 2018, which is incorporated herein by reference, at Additional File 3.

COD Calculations. Unless otherwise noted, we report concentrations as mass of COD per unit volume. This allows for the direct comparison of relative reducing equivalents contained within each of the compounds consumed and created. The theoretical COD of each compound, or the theoretical amount of oxygen needed to fully oxidize the compound, was used to convert the measured mass units to COD. Protein was assumed to have 1.5 g COD per g of protein, which is consistent with the COD of albumin. A COD of 1.06 g COD per g carbohydrate was used to convert total carbohydrates measured with the anthrone method to COD. This value is consistent with the COD of glucose and xylose. The "Unknown COD" represents the measured COD minus the COD of known components. Where provided, error bars represent standard deviation of technical replicates. The "COD Removed" is calculated as the percentage of COD removed at each time point. "Conversion of Carbohydrates" is calculated based on the difference between total carbohydrates in the switchgrass stillage and the reactor sample for each time point. "Conversion to SCFA" is based on the amount of COD converted to carboxylic acids containing two to five carbons (short-chain fatty acids; SCFA), and "Conversion to MCFA" is based on the COD converted to monocarboxylic acids containing six to eight carbons.

Results

Chemical Analyses of Switchgrass Stillage.

In a lignocellulosic biorefinery, an ethanologenic microorganism ferments biomass sugars to ethanol and the ethanol is removed via distillation, producing an organic-rich stillage fraction. The concentrations of compounds remaining in stillage are therefore dependent on the efficiency of the upstream fermentation. For this example, two batches of stillage (Table 2) were produced from switchgrass hydrolysate fermented with *S. cerevisiae* Y128, a strain with improved utilization of xylose.[20] The starting glucose and xylose concentrations in the hydrolysate prior to fermentation were 56,000±300 mg COD $L^{-1}$ and 36,000±200 mg COD $L^{-1}$, respectively. After the fermentation, the ethanol concentration was 51,000±2,900 mg COD $L^{-1}$ with nearly 100% of the glucose and 47% of the xylose consumed. Glycerol, a common byproduct of yeast fermentation,[43] reached a final concentration of 2,500±100 mg COD $L^{-1}$. Acetic and formic acids decreased slightly during the ethanologenic fermentation, and only a small amount of lactic acid (30±1 mg COD $L^{-1}$) was detected (see Scarborough and Lynch et al. 2018, which is incorporated herein by reference, at Additional File 1). The total COD of the two batches of fermented hydrolysate was 160,000±1,500 mg COD $L^{-1}$ (Scarborough and Lynch et al. 2018, which is incorporated herein by reference, Additional File 1).

TABLE 2

Major chemical components contained within hydrolysate and fermented hydrolysate after fermentation with *Saccharomyces cerevisiae* Y128.

| | Hydrolysate (mg COD $L^{-1}$) | Fermented Hydrolysate (mg COD $L^{-1}$) |
|---|---|---|
| Glucose | 56,000 ± 300 | 44 ± 1.7 |
| Xylose | 36,000 ± 230 | 19,000 ± 4,500 |
| Glycerol | 310 ± 0.86 | 2,500 ± 130 |
| Acetic acid | 2,065 ± 30 | 1,600 ± 68 |
| Ethanol | <100 | 51,000 ± 2,900 |

The COD remaining in stillage, after distilling ethanol from the fermented hydrolysate, was approximately 60% of the COD in the fermented hydrolysate. The major chemical energy components in the stillage included xylose, acetamide (derived from acetate during ammonia-based pretreatment of switchgrass), glycerol, and acetic acid (Table 3). Residual glucose was minimal (Table 2), and the ethanol that was not removed in distillation (Table 3) represented less than 3% of the ethanol present in the original fermentation broth (Table 2). Carbohydrates, excluding xylose, accounted for 18% of the COD, while proteins accounted for only 2.2% of the COD in the stillage. In addition, a large portion of the COD is comprised of components with undetermined chemical identity. This "Unknown COD" likely contains a variety of compounds that are either produced during biomass deconstruction, originate from the switchgrass, or are produced during the yeast ethanol fermentation.

TABLE 3

Composition of major organic matter components and aromatic compounds in the two batches of stillage fed to the mixed culture fermentation bioreactor. Major stillage components are reported in mg COD $L^{-1}$ whereas aromatic compounds are reported in µg COD $L^{-1}$.

| | Stillage Batch 1 | Stillage Batch 2 |
|---|---|---|
| Major Stillage Components | mg COD $L^{-1}$ | |
| Soluble COD | 95,400 ± 432 | 95,800 ± 982 |
| Unknown COD | 38,300 ± 3,250 | 42,100 ± 3,190 |
| Xylose | 20,800 ± 148 | 20,900 ± 168 |
| Other Carbohydrates | 19,300 ± 2,310 | 15,500 ± 2,230 |
| Acetamide | 4,030 ± 270 | 4,200 ± 340 |
| Glycerol | 3,900 ± 32.1 | 3,920 ± 36.3 |
| Acetic acid | 2,550 ± 21.1 | 2,580 ± 20.5 |
| Proteins | 2,200 ± 145 | 1,910 ± 162 |
| Ethanol | 1,220 ± 305 | 1,590 ± 161 |
| Aromatic Compounds | µg COD $L^{-1}$ | |
| Coumaroyl amide | 13,000 ± 250 | 5,400 ± 200 |
| Feruloyl amide | 12,000 ± 130 | 3,200 ± 83 |
| p-Coumaric acid | 3,500 ± 43 | 1,100 ± 34 |
| Benzoic acid | 1,700 ± 102 | 2,000 ± 22 |
| Vanillamide | 290 ± 0.95 | 230 ± 0.50 |
| 4-hydroxybenzoic acid | 380 ± 15 | 320 ± 0.46 |
| Vanillic acid | 320 ± 0.09 | 370 ± 4.6 |
| Ferulic acid | 250 ± 13 | 90 ± 3.2 |
| 4-hydroxybenzyl alcohol | 240 ± 3.7 | 110 ± 1.9 |
| Syringamide | 230 ± 0.06 | 138 ± 2.3 |

While major COD components between the two batches of stillage were similar, the aromatic compounds, including known lignotoxins,[19,44] varied between the stillage batches Table 3. Feruloyl amide, p-coumaroyl amide, and coumaric acid were higher in Batch 1 than in Batch 2. Only benzoic acid and vanillic acid were higher in Batch 2. From a reducing-equivalents standpoint, these aromatic compounds account for less than 0.05% of the COD in stillage, but these concentrations are within the range of lignotoxins shown to inhibit fermentation activity by pure cultures of ethanologenic organisms.[20]

Stillage Fermentation Under Different pH Conditions.

Due to the relatively low concentration of six carbon sugars, the complexity of remaining organic materials, and the potential toxicity of aromatic compounds, bacterial growth on stillage derived from ALFEX-treated hydrolysate was expected to be challenging. We therefore conducted short-term experiments to determine if a microbial community could metabolize organic materials remaining in stillage. Using inoculum from an acid phase anaerobic digester, we fermented stillage at different pH conditions (uncontrolled, 5.0, 5.5, 6.0, and 6.5) for 6 days using an SRT of 2 days and analyzed both the extracellular end products and the microbial community. Acid phase digester sludge was used as inoculum because the microbial consortia was expected to contain a variety of fermenting organisms and not expected to contain high levels of methanogens.[45, 46]

Conditions in which the pH was uncontrolled led to the pH stabilizing at 3.6 and accumulation of lactic and acetic acids (FIG. 1). SCFA and MCFA accumulated in the reactor when the pH was maintained between 5.0 and 6.5. Maintaining a pH of 5.5 resulted in the highest accumulation of MCFA (Scarborough and Lynch et al. 2018, which is incorporated herein by reference, Additional File 4). Analysis of the microbial community by 16S rRNA gene sequencing showed variations in composition with pH (see Scarborough and Lynch et al. 2018, which is incorporated herein by reference, at FIG. 2.S2), with OTUs associated with the genera *Lactobacillus* (89.9%) and *Acetobacter* (9.9%) becoming the most abundant when the pH was uncontrolled. *Lactobacillus* was present in the reactors at all pH conditions. At pH 5.0, *Megasphaera* was enriched (46.3%), while at pH 5.5, OTUs related to *Pseudoramibacter* (14.3%) and *Olsenella* (14.1%) were abundant. At pH 6.0, *Mitsuokella* (20.8%), *Acetitomaculum* (17.0%), and *Megasphaera* (14.2%) were all abundant. When the reactor was maintained at pH 6.5, more OTUs related to the *Bacteriodetes* phylum were abundant, including OTUs related to the genera *Prevotella* (12.3%) and *Bacteroides* (40.8%).

These results demonstrated that a community derived from an acid digester sludge inoculum could ferment stillage to carboxylic acids, including MCFAs, under a variety of pH conditions. Further, organisms identified in the stillage-fed reactors included members of the *Clostridia* (*Megasphaera*, *Pseudoramibacter*) that have previously been associated with MCFA production.[5,10,13,15,18,47] Members of *Clostridia* have been enriched in other MCFA-producing bioreactors under similar pH conditions.[12,18,48] In agreement with our observation of *Lactobacillus* at all pH conditions, *Lactobacillus* is a common genera in MCFA producing microbiomes.[10,15,17,18,47] In total, the fermentation product (FIG. 1) and community (see Scarborough and Lynch et al. 2018, which is incorporated herein by reference, at FIG. 2.S2) data confirmed that materials in stillage could be converted to MCFA by a microbial community originating from a full-scale wastewater treatment plant acid-digester.

Sustained MCFA Production from Switchgrass Stillage.

Figure 2A:
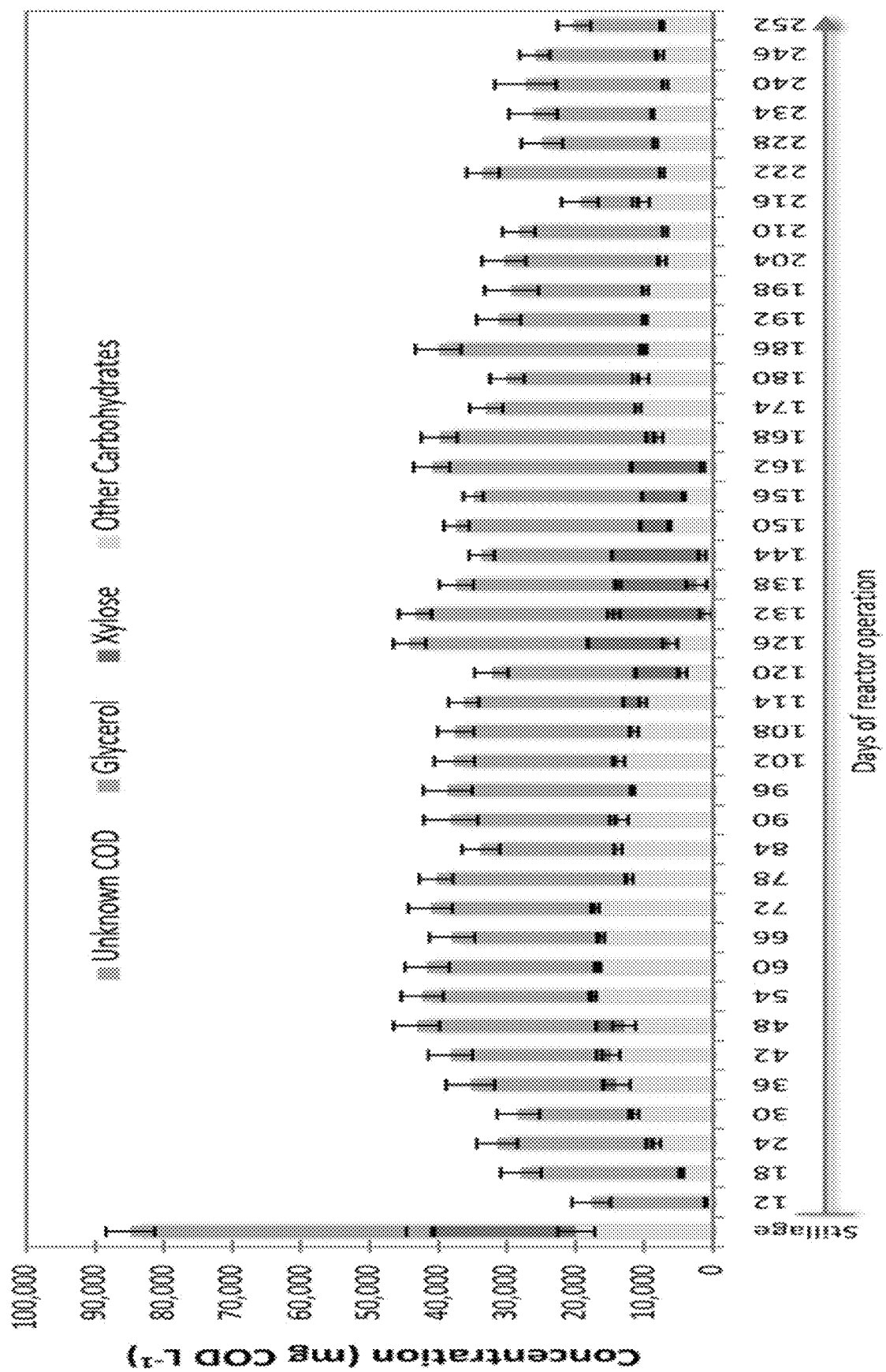
FIGS. 2A-2D. Mixed culture fermentation reactor performance for 252 days.
Figure 2B:
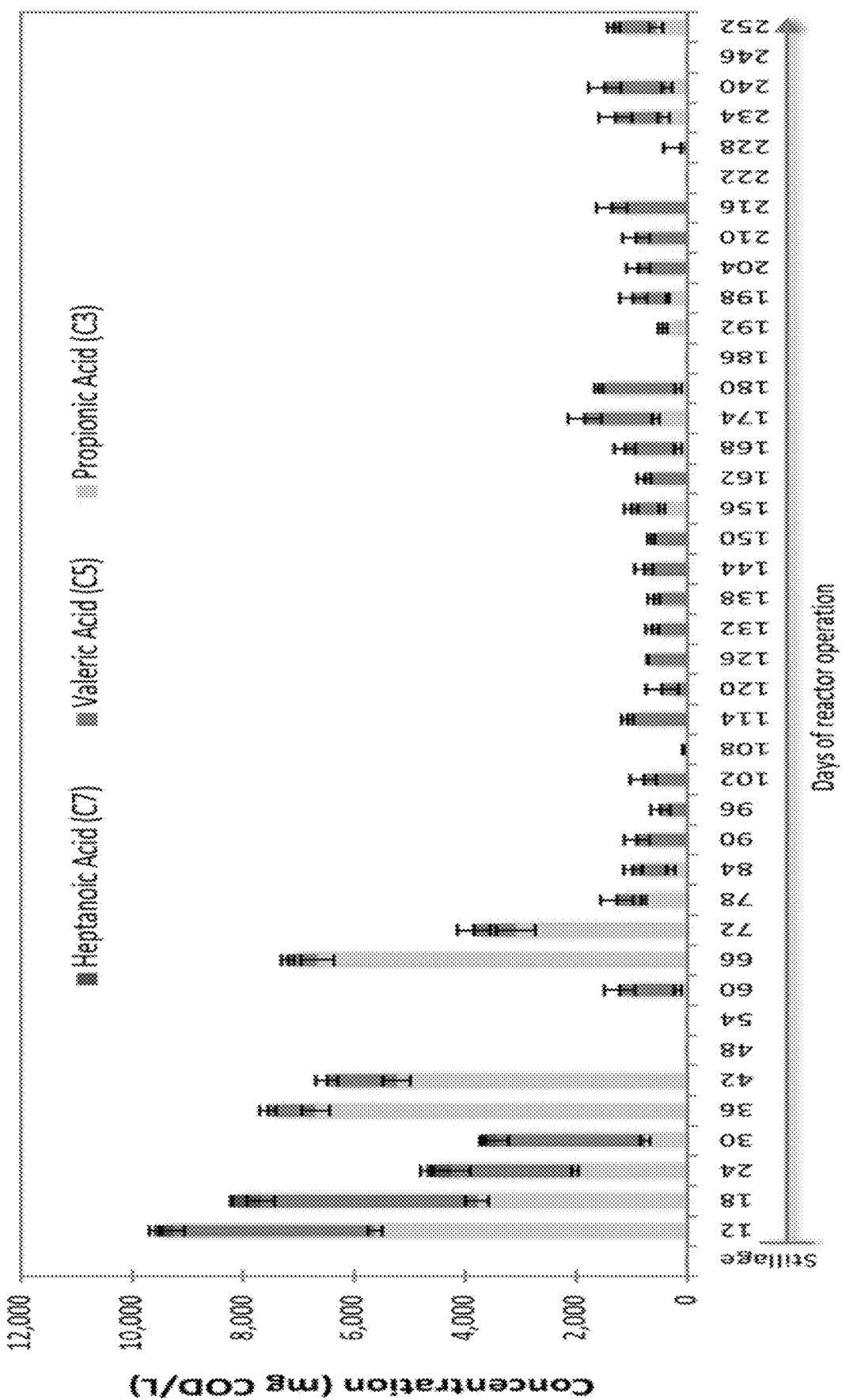
Figure 2C:
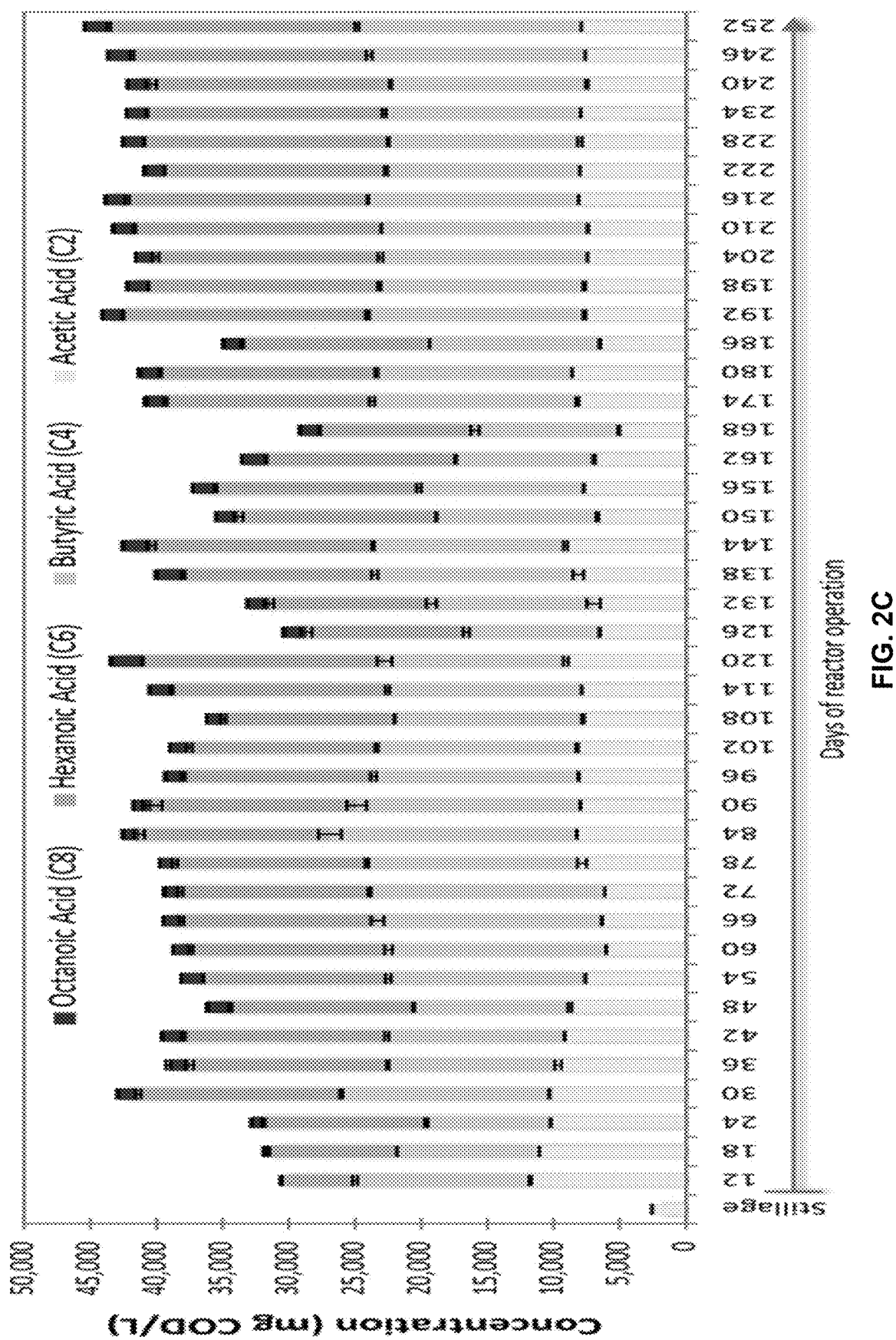
Figure 2D:
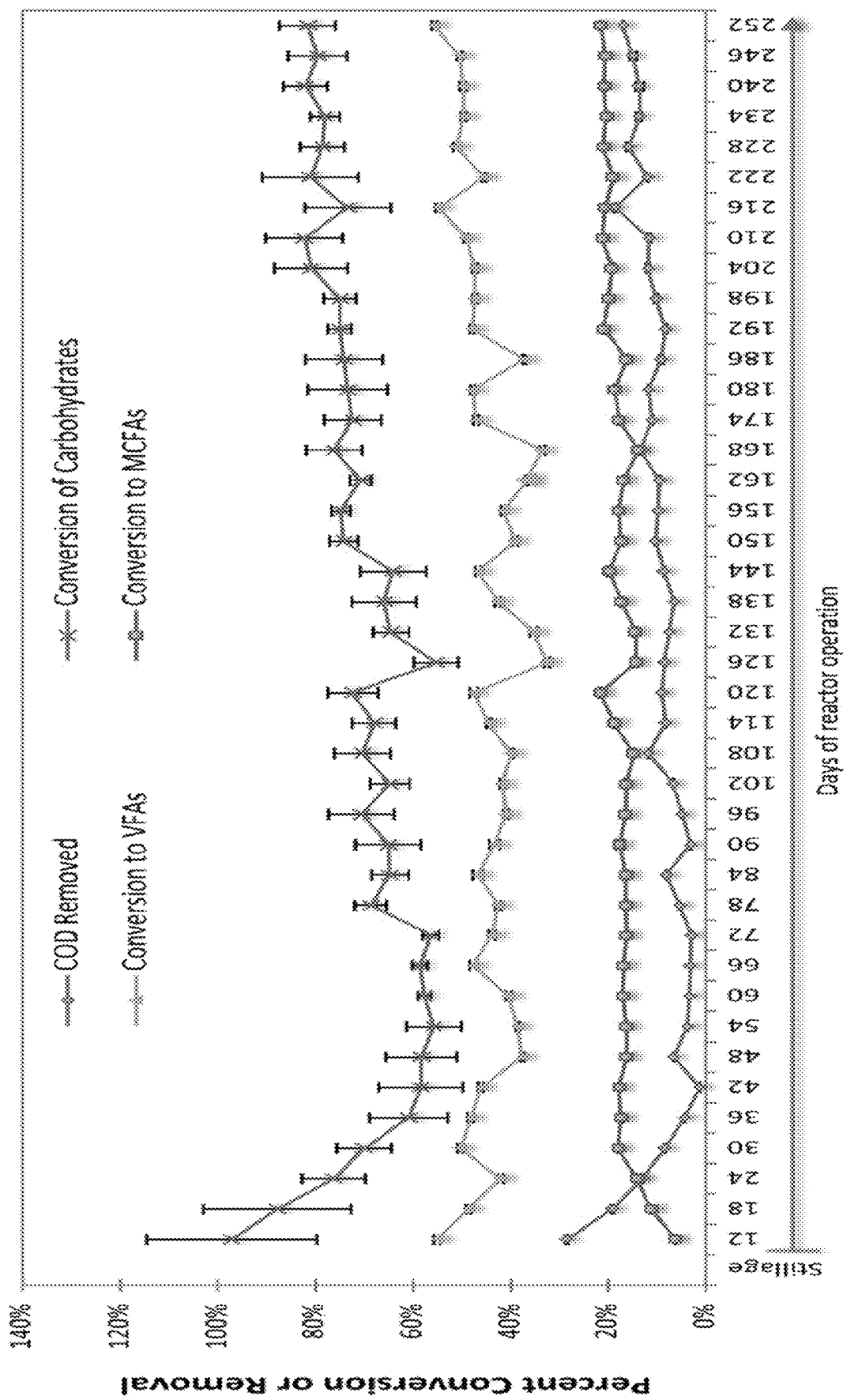

Based on these results, we chose to control the reactor pH at 5.5 for a long-term experiment to demonstrate sustained production of MCFA. Initially, xylose and other carbohydrates were consumed, and a mixture of odd- and even-chain linear fatty acids were produced (FIGS. 2A-2D). The maximum utilization of carbohydrates was achieved at Day 12, with 97±17% of the measured initial carbohydrates consumed (FIG. 2D). During the first 30 days of operation, accumulation of monocarboxylic acids steadily increased, reaching nearly 50% conversion of COD in stillage to monocarboxylic acids (FIG. 2D). As reactor operation continued, the concentration of odd-chain monocarboxylic acids (C3, C5, C7) decreased (FIG. 2B) while that of even-chain acids increased (FIG. 2C). From Day 30 through Day 252, the average conversion of COD in stillage to MCFA was 18±2.1%, and MCFA accounted for 41±7.0% of the total monocarboxylic acids produced.

Microbial Community Analysis.

Figure 3:
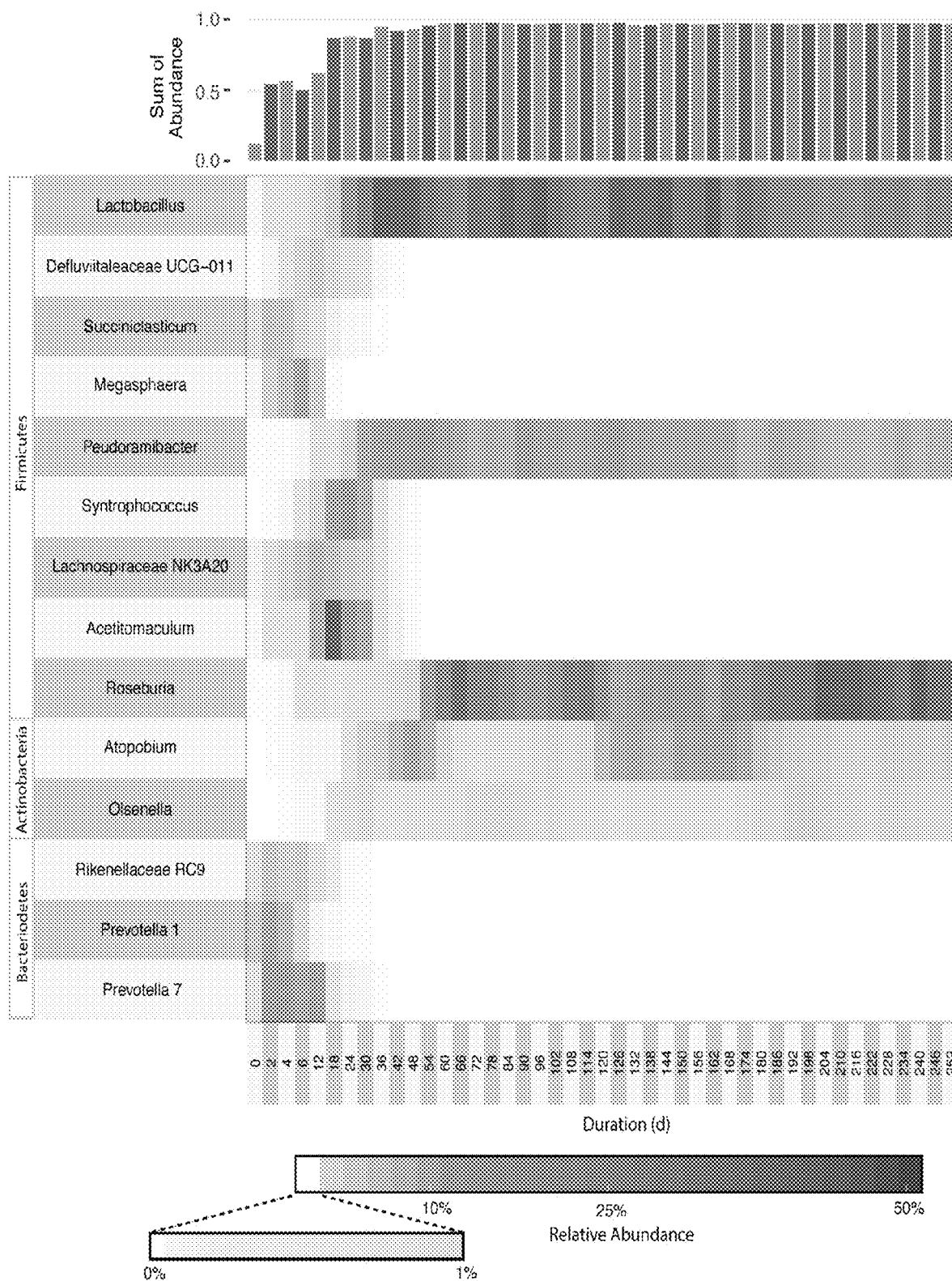
FIG. 3. Relative abundance of bacteria in the mixed culture fermentation reactor for 252 days. Day 0 corresponds to the acid digester sludge inoculum. Bacterial abundance is summarized based on the genera assigned by annotating representative sequences with the SILVA database. The sum of abundance represents the percentage of operational taxonomic units (OTUs) contained within the indicated genera. A heatmap of the top 100 OTUs is provided in Scarborough and Lynch et al. 2018, which is incorporated herein by reference, at FIG. S3, and a table of all OTUs is provided in Scarborough and Lynch et al. 2018 at Additional File 4.

We used 16S rRNA gene amplicon sequencing to assess the members of the microbial community in this bioreactor and any changes that occurred in its composition as a function of time (FIG. 3; see also Scarborough and Lynch et al. 2018, which is incorporated herein by reference, at FIG. 2.S3). The initial microbial community contained many *Proteobacteria, Firmicutes*, and *Bacteriodetes* (see Scarborough and Lynch et al. 2018, which is incorporated herein by reference, at FIG. 2.S3). Early on in reactor operations, *Bacteroidetes* and *Firmicutes* became the most abundant organisms, with *Prevotella* species accounting for most of the *Bacteroidetes*. The increase in abundance of *Prevotella* 7 (FIG. 3) corresponds with the time of increased carbohydrate conversion ($p<0.001$), in agreement with *Prevotella*'s described ability to degrade polysaccharides and other complex substrates.[49] *Megasphaera*, an organism known to produce odd-chain fatty acids (OCFA)[50], was present in the inoculum and increased in abundance during the early phase of reactor operation. The high abundance of *Megasphaera* ($p=0.0023$) and *Prevotella* 7 ($p=0.0016$) at early stages of reactor operation corresponded with a period of higher OCFA production.

After extended operation, we found that the community composition stabilized and was dominated by organisms from five genera, including three Firmicutes (*Lactobacillus, Pseudoramibacter, Roseburia*) and two Actinobacteria (*Olsenella, Atopobium*). At later time points (Day 30-Day 252), the OTUs corresponding to these five genera accounted for greater than 95% of the total 16S rRNA gene sequences (FIG. 3). The relative abundance of *Pseudoramibacter* ($p=0.0045$), *Lactobacillus* ($p=0.0022$), and *Olsenella* ($p=0.014$) all correlated with the period of increased MCFA production. Neither *Roseburia* ($p=0.147$) nor *Atopobium* ($p=0.546$) are significantly correlated to increased MCFA production.

Figure 4:
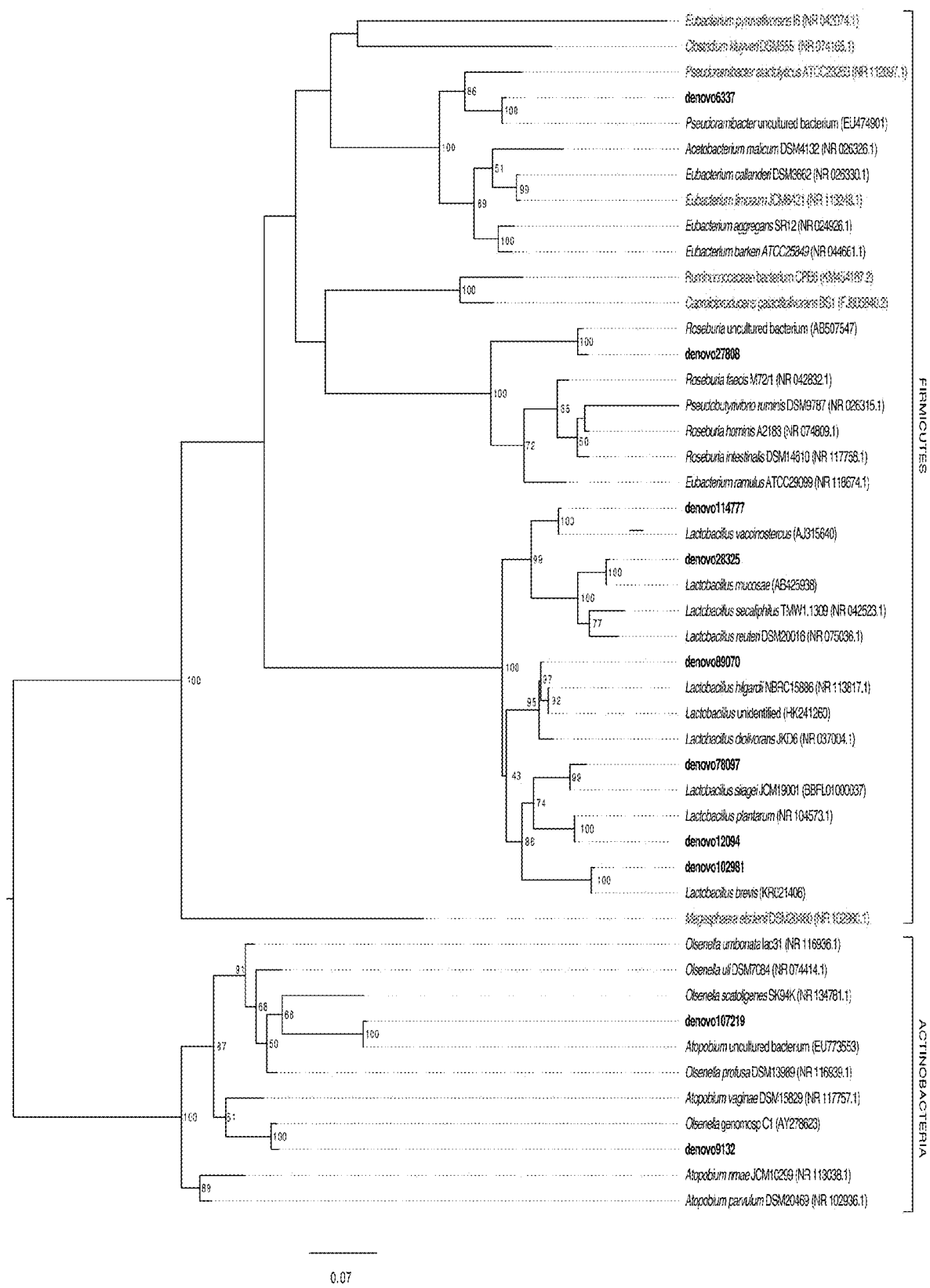
FIG. 4. Phylogenetic tree including the top 10 most abundant OTUs at Day 252. OTUs from this example are shown in bold text. Known chain-elongating bacteria are shown in red text. Bootstrap values greater than 50 are shown, and the phylogenetic tree is rooted to the Actinobacteria phylum. The horizontal branch distance corresponds to the mean nucleotide substitutions per sequence site. The accession numbers for 16S rRNA gene sequences for the indicated bacteria are provided in parentheses.
Figure 5:
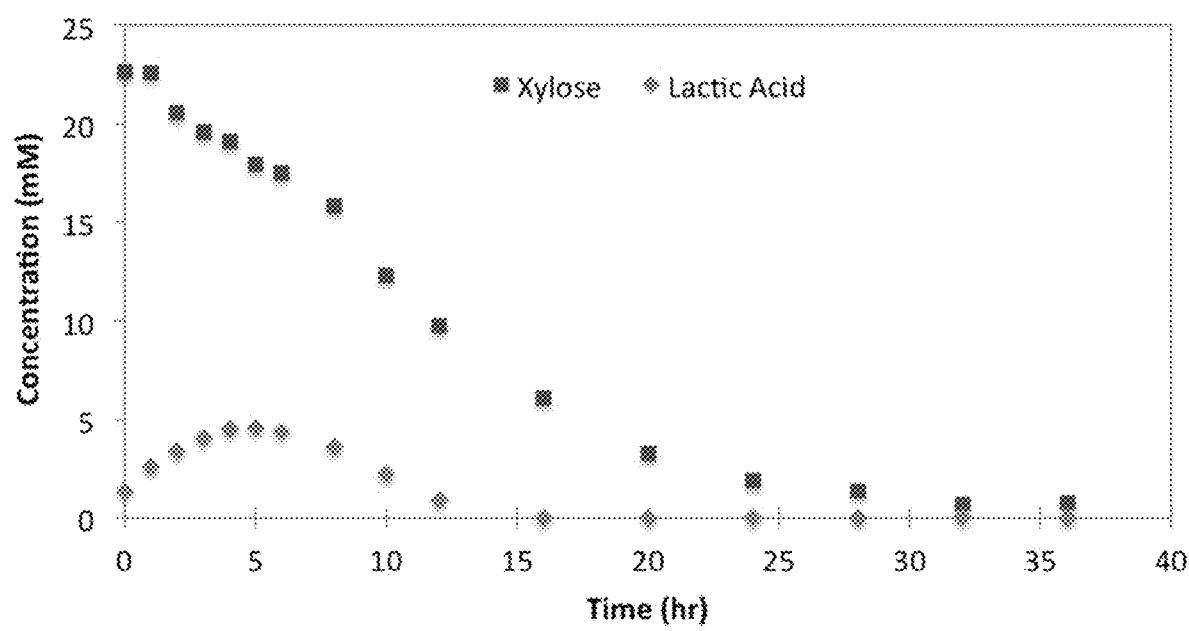
FIG. 5. Time-dependent changes of xylose and lactic acid concentrations. Lactic acid and xylose were measured after adding a spike feed of 25 ml stillage to the reactor at 252 days of operation. As xylose is removed from the media, lactic acid accumulates at approximately one mol of lactic acid per mol of xylose consumed. Extracellular lactic acid begins to decrease six hours after the addition of stillage.

Representative sequences for the most abundant OTUs were used to construct a maximum-likelihood phylogenetic tree (FIG. 4). The six high abundance *Lactobacillus* OTUs (denovo114777, denovo28325, denovo102981, denovo12094, denovo78097, and denovo89070) clustered with known xylose-consuming, heterofermentative *Lactobacilli* (*L. mucosae, L. plantarum, L. silagei, L. brevis, L. vaccinostercus* and *L. diolivorans*).[51-58] As lactic acid has previously been demonstrated as a substrate for MCFA production,[14,15] it may be a key intermediate for MCFA production in a microbial community.[18] While significant lactic acid accumulation was not observed during steady-state sampling, when we monitored time-dependent changes in the reactor after stillage was spike-fed, lactic acid transiently accumulated to detectable levels in the medium (FIG. 5) suggesting that lactic acid is produced but consumed by other community members.

The two OTUs within the Actinobacteria phylum, denovo9132 and denovo107219, clustered with members of the *Atopobium* and *Olsenella* genera respectively (FIG. 4), in the *Coriobacteriaceae* family. Several *Atopobium* and *Olsenella* species have been shown to consume carbohydrates and produce lactic acid.[59-62] The most abundant OTU at 252 days of reactor operation (denovo27808) clustered with *Roseburia*, which are known to utilize carbohydrates and acetic acid and produce butyric and lactic acids.[63-65] Another high abundance OTU identified in the microbial community (denovo6337) clustered with *Pseudoramibacter alactolyticus*, (previously *Eubacterium alactolyticum*) a bacterium that has been described as producing hexanoate and octanoate from lactic acid and glucose.[66]

Starting at Day 120, the feed changed from Stillage Batch 1 to Stillage Batch 2, which contained lower concentrations of aromatic compounds (Table 3). While initial changes in community compositions occurred (FIG. 3), with an increase in *Atopobium* and decrease in *Roseburia*, the major genera remained consistent and the community eventually re-stabilized. This initial change in stillage feed source coincided with a reduction in xylose utilization (FIG. 2A), however xylose utilization eventually increased and overall MCFA production was not impacted by this change in the stillage source ($p=0.415$).

We also performed redundancy analysis to relate the community composition with MCFA production, odd-chain fatty acid production (OCFA), and carbohydrate conversion and to investigate co-occurrence of abundant bacteria in the reactor (see Scarborough and Lynch et al. 2018, which is incorporated herein by reference, at FIG. 2.6). For early time points (Days 12-24), the abundance of *Prevotella* and *Megasphaera* correlate with OCFA production. The analysis also showed that higher relative abundance of *Lactobacillus* is associated with higher relative abundance of *Pseudoramibacter* and higher relative abundance of *Roseburia* correlates with higher relative abundance of *Olsenella* (see Scarborough and Lynch et al. 2018, which is incorporated herein by reference, at FIG. 2.6). These correlations suggest that these organisms may work in tandem during stillage metabolism. In the case of *Lactobacillus* and *Pseudoramibacter*, the *Lactobacillus* may be producing lactate that *Pseudoramibacter* converts to MCFA. This relationship is analogous to that suggested by Andersen et al. in which *Megaspahera* utilized lactate generated by *Lactobacillus*.[17] Similarly, *Olsenella* may be producing intermediates, such as acetate, that are known to be utilized by *Roseburia*.

Overall, the bacterial community results indicate that a stable fermenting community containing only five genera was enriched from the acid-digester sludge inoculum during growth on stillage. We suspect that *Clostridia*-related organisms (*Pseudoramibacter* and/or *Roseburia*) are responsible for MCFA production and the remaining community members ferment sugars to intermediate compounds (acetate, lactate, and/or ethanol) that provide substrates for MCFA production.

Economic Analysis of MCFA Production from Stillage.

Based on the sustained production of MCFA in this example, we evaluated the potential value of this process. We did this by modifying the NREL TEA for a lignocellulosic ethanol biorefinery to include a process in which stillage is used to produce MCFA. Using average percent conversions in the bioreactor between Day 30 and Day 252, we estimated that the COD remaining in stillage was converted to end products at the following percentages: 5.4% acetic acid, 15% butyric acid, 16% hexanoic acid, and 1.7% octanoic acid. Further, based on reactor operations during the same time period, 9.1% of the COD is removed from the system as off-gas.

Based on these conversions, a new mass and energy balance for the biorefinery was determined (see Scarborough and Lynch et al. 2018, which is incorporated herein by reference, at FIG. 2.7). The MCFA-producing fermentation reactor was sized for a SRT of 6 days, yielding an estimated total reactor volume of 16 million gallons. Software simulations predicted that a solvent flow rate of 9,000 kg hr$^{-1}$ was needed to recover 99.9% of the octanoic acid and 96.4% of the hexanoic acid, respectively. Software simulations further predicted that of the 9,000 kg hr$^{-1}$ 2-octanol feed, 745 kg hr$^{-1}$ separates into the aqueous phase and needs to be replenished. In our TEA, the organic phase undergoes a column distillation to remove 2-octanol that has a volume of 630 ft$^3$ and requires a total heating duty of 6.3 MW. After distilling the solvent, the model assumes that hexanoic and octanoic acids are separated in a second distillation column with a volume of 240 ft$^3$ that requires a total heating duty of 0.75 MW.

After the liquid-liquid extraction, the aqueous phase is fed to biogas-producing anaerobic digesters (see Scarborough and Lynch et al. 2018, which is incorporated herein by reference, at FIG. 2.7). Anaerobic digestion of lignocellulosic stillage[67] and acid digested stillage[68] for biogas production has been demonstrated by others. The mass flow rate of COD to the anaerobic digesters, including stillage, lignin, and biosolids, is 21,000 kg hr$^{-1}$, resulting in biogas production of 16,600 kg hr$^{-1}$ (compared to 21,900 kg hr$^{-1}$ if the stillage is used directly as in the NREL TEA).[2] The overall power generation from the remaining organics after MCFA removal is reduced from 41.0 MW to 38.0 MW. The reduction in overall power generation is small because lignin contributes the majority of COD to the anaerobic digesters.

As a result of the additional heating demands for the MCFA distillation columns, the net electricity that can be sold decreased from 13.7 MW to 3.8 MW (see Scarborough and Lynch et al. 2018, which is incorporated herein by reference, at Table 2.3). In addition, the capital costs associated with the stillage fermentation reactor, liquid-liquid-extraction, and distillation columns increased the total capital investment from $423 million to $441 million. The additional chemical costs for KOH and 2-octanol added annual operating costs of $14 million and $8.3 million, respectively. However, the MCFA products increased revenue by $57 million ($7.5 million from octanoic acid, and $47.5 million from hexanoic acid). Based on a 30-year cash flow with a 10% internal rate of return, the minimum ethanol selling price was determined to be $1.76 per gallon ($2.68 per gallon gasoline-equivalents; see Scarborough and Lynch et al. 2018, which is incorporated herein by reference, at FIG. 2.S4). This is 18% lower than the $2.15 per gallon for when electricity is generated as the only co-product to ethanol.[2]

Discussion

This example illustrates the use of microbial communities to convert stillage into valuable co-products. In the stillage-fed bioreactor, productivities of hexanoic (2.6±0.3 g L$^{-1}$ d$^{-1}$) and octanoic (0.27±0.04 g L$^{-1}$ d$^{-1}$) acids were sustained for 214 days with titers at 66±8.2% and 97±15% of their solubility in water, respectively. These productivities are consistent with other studies investigating conversion of organic substrates derived from lignocellulosic materials or ethanol production wastes to MCFA (see Scarborough and Lynch et al. 2018, which is incorporated herein by reference, at Table 2.S1). Our system is unique, however, at least in that the primary carbohydrate consumed is xylose and the stillage has already been depleted of a large portion of fermentable sugars and the ethanol that others have used to produce MFCA. While we are proposing the co-production of ethanol and MCFA in this example, recent work has also explored production of MCFA as the main product of a lignocellulosic biorefinery. In work performed by Nelson et al., *Megasphaera* consumed glucose in lignocellulosic hydrolysate to generate hexanoic acid, but xylose was not consumed.[16] The microbial community like the one presented in this example could be utilized to convert the remaining xylose to MCFA.

The simplicity of the microbial community enriched in this example positions it well as a model community for MCFA production. Others have shown enrichments containing OTUs related to primary sugar fermenters, such as *Lactobacillus*, and OTUs related to *Clostridia* that may be involved in converting intermediate fermentation products to MCFA.[13-15,17,18,47,69] In our microbial community, at Day 252, only 10 OTUs are present at greater than 1% relative abundance, and these OTUs make up 89.3% of the total OTUs (see Scarborough and Lynch et al. 2018, which is incorporated herein by reference, at FIG. 2.S3). The statistical analyses indicate that *Pseudoramibacter* and *Lactobacillus* are co-enriched, and their abundance correlates with higher MCFA production. We therefore propose that *Lactobacillus* converts xylose to lactate and acetate by heterofermentation, and the lactate is elongated to MCFA by *Pseudoramibacter*. While 16S rRNA gene sequencing allows for the phylogeny of abundant organisms to be estimated, the function of community members should be investigated further utilizing metagenomic approaches. Due to the simplicity of the microbial community obtained in this example, this microbiome is well positioned for further investigation with metagenomic tools. Furthermore, its simplicity makes this a candidate microbiome for simulation with synthetic communities in the future. Of the OTUs that became enriched in the reactor, only *Roseburia* (denovo27808) and *Pseudoramibacter* (denovo6337) emerged as likely MCFA producing bacteria. While *Pseudoramibacter* have been shown to produce MCFA,[66] to our knowledge, the ability of *Roseburia* to produce MCFA has not been studied.

The TEA shows that even at the modest productivities of hexanoic and octanoic acids obtained in this example, MCFA produced from ethanol stillage could improve the economic feasibility of lignocellulosic biorefining. Improvements in the overall conversion of stillage COD to MCFA and production of a higher proportion of octanoic acid would further increase the revenue that can be generated by this strategy. Increasing MCFA product specificity towards octanoic acid is an ongoing area of research. One strategy to increase octanoic acid production is to utilize pertractive extraction of MCFAs to reduce product inhibition, as has been performed in past studies.[13,14] Recent work has also shown that increasing the ratio of ethanol to acetate increases selectivity of octanoic acid production.[13] The model of increasing the ratio of reduced electron donors to acetate suggests that, in the absence of ethanol, increasing the production of lactate as a fermentation intermediate (rather than acetate) could further drive octanoic acid production.

The economy of co-producing MCFA may also be affected by upstream biomass processing (i.e., the conversion of plant polymers to their constituent monomer units) and ethanol fermentation. For example, utilization of xylose by industrial yeast strains, such as *S. cerevisiae*, is limited[20], although attempts to improve pentose utilization by ethanol producers is an area of intense research activity.[70] Even though the *S. cerevisiae* Y128 strain used in this example was engineered for improved xylose utilization, it only consumed 47% of the xylose available in the switchgrass hydrolysate. Future ethanologenic organisms used in a lignocellulosic biorefinery may leave less xylose available for MCFA production. However, given the higher price of MCFA compared to ethanol, decreasing xylose consumption by the ethanologenic organism may actually result in an improved economy of the lignocellulosic biorefinery.

Another simple opportunity for improving the economic potential of co-producing MCFA is utilizing sodium hydroxide for pH control, instead of KOH, as sodium hydroxide is roughly one-sixth the cost of KOH. In our current model, the cost of KOH is a major expense. Alternatives to controlling pH with chemicals, such as electrolytic extraction which both controls the pH and extracts the acid products,[17] should also be explored further.

Conclusion

In this example, we showed that microbial communities could be used to produce valuable compounds from lignocellulosic stillage. We developed conditions for sustained MCFA production by an anaerobic microbiome that uses stillage produced during lignocellulosic biorefining. By fermenting switchgrass stillage, we maintained productivities of hexanoic and octanoic acids of 2.6±0.3 g $L^{-1}$ $d^{-1}$ and 0.27±0.04 g $L^{-1}$ $d^{-1}$, respectively. To our knowledge, this is the first demonstration of MCFA production with xylose and other organics in lignocellulosic ethanol stillage as the primary substrates. The MCFA-producing microbial community was derived from a diverse wastewater treatment ecosystem, but over time it became enriched in OTUs representing only five genera, including members of the Firmicutes phylum (*Lactobacillus*, *Roseburia*, and *Pseudoramibacter*) and of the Actinobacteria phylum (*Olsenella* and *Atopobium*). *Pseudoramibacter* are *Clostridia* related to known MCFA producing organisms, some of which have been shown to produce hexanoic and octanoic acids.[66]

A TEA, based on an update to an industry-accepted model, shows that, at the productivity of MCFA achieved in this example, valorizing lignocellulosic ethanol stillage to MCFA could improve the economic sustainability of a biorefinery. For example, using the MCFA production experimentally observed, if 16% of the COD remaining in stillage is converted to hexanoic acid and 1.7% is converted to octanoic acid, the minimum ethanol selling price could be reduced by 18%, from $2.15 $gal^{-1}$ to $1.76 $gal^{-1}$. Optimizations to microbiome MCFA productivities, MCFA extraction, solvent recovery and selection of the ethanologenic organism may contribute further to improving the economy of the lignocellulosic biorefinery.

REFERENCES

1. K. Gerbrandt, P. L. Chu, A. Simmonds, K. A. Mullins, H. L. MacLean, W. M. Griffins and B. A. Saville, *Curr. Opin. Biotechnol.*, 2016, 38, 63-70.
2. D. Humbird, R. Davis, L. Tao, C. Kinchin, D. Hsu, A. Aden, P. Schoen, J. Lukas, B. Olthof, M. Worley, D. Sexton and D. Dudgeon, Process Design and Economics for Biochemical Conversion of Lignocellolosic Biomass to Ethanol, NREL, 2011.
3. Senate and House of Representatives of the United States of America, Energy Policy Act of 2005, US Government Publishing Office, Washington, D.C., 2005.
4. Senate and House of Representatives of the United States of America, Energy Independence and Security Act of 2007, US Government Publishing Office, Washington, D.C., 2007.
5. L. T. Angenent, H. Richter, W. Buckel, C. M. Spirito, K. J. J. Steinbusch, C. M. Plugge, D. Strik, T. I. M. Grootscholten, C. J. N. Buisman and H. V. M. Hamelers, *Environ. Sci. Technol.*, 2016, 50, 2796-2810.
6. S. Sarria, N. S. Kruyer and P. Peralta-Yahya, Nat. Biotechnol., 2017, 35, 1158-1166.
7. I. Gelfand, R. Sahajpal, X. Zhang, R. C. Izaurralde, K. L. Gross and G. P. Robertson, *Nature*, 2013, 493, 514-517.
8. M. T. Agler, B. A. Wrenn, S. H. Zinder and L. T. Angenent, *Trends Biotechnol.*, 2011, 29, 70-78.
9. M. T. Holtzapple and C. B. Granda, Appl. Biochem. Biotechnol., 2009, 156, 95-106.
10. M. T. Agler, C. M. Spirito, J. G. Usack, J. J. Werner and L. T. Angenent, *Energy Environ. Sci.*, 2012, 5, 8189.
11. C. Urban, J. Xu, H. Sträuber, T. R. dos Santos Dantas, J. Mühlenberg, C. Härtig, L. T. Angenent and F. Harnisch, *Energy Environ. Sci.*, 2017, DOI: 10.1039/c7ee01303e.
12. D. Vasudevan, H. Richter and L. T. Angenent, *Bioresour. Technol.*, 2014, 151, 378-382.
13. L. A. Kucek, C. M. Spirito and L. T. Angenent, *Energy Environ. Sci.*, 2016, 9, 3482-3494.
14. L. A. Kucek, M. Nguyen and L. T. Angenent, *Water Res.*, 2016, 93, 163-171.
15. X. Zhu, Y. Tao, C. Liang, X. Li, N. Wei, W. Zhang, Y. Zhou, Y. Yang and T. Bo, Sci. Rep., 2015, 5, 14360.
16. R. Nelson, D. Peterson, E. Karp, G. Beckham and D. Salvachúa, *Fermentation*, 2017, 3, 10.

17. S. J. Andersen, P. Candry, T. Basadre, W. C. Khor, H. Roume, E. Hernandez-Sanabria, M. Coma and K. Rabaey, *Biotechnol Biofuels*, 2015, 8.
18. S. J. Andersen, V. De Groof, W. C. Khor, H. Roume, R. Props, M. Coma and K. Rabaey, *Front Bioeng Biotechnol*, 2017, 5, 8.
19. R. G. Ong, A. Higbee, S. Bottoms, Q. Dickinson, D. Xie, S. A. Smith, J. Serate, E. Pohlmann, A. D. Jones, J. J. Coon, T. K. Sato, G. R. Sanford, D. Eilert, L. G. Oates, J. S. Piotrowski, D. M. Bates, D. Cavalier and Y. Zhang, *Biotechnol Biofuels*, 2016, 9, 237.
20. L. S. Parreiras, R. J. Breuer, R. Avanasi Narasimhan, A. J. Higbee, A. La Reau, M. Tremaine, L. Qin, L. B. Willis, B. D. Bice, B. L. Bonfert, R. C. Pinhancos, A. J. Balloon, N. Uppugundla, T. Liu, C. Li, D. Tanjore, I. M. Ong, H. Li, E. L. Pohlmann, J. Serate, S. T. Withers, B. A. Simmons, D. B. Hodge, M. S. Westphall, J. J. Coon, B. E. Dale, V. Balan, D. H. Keating, Y. Zhang, R. Landick, A. P. Gasch and T. K. Sato, *PLoS One*, 2014, 9, e107499.
21. W. E. F. American Public Health Association, and American Water Works Association Standard Methods for the Examination of Water and Wastewater: 21st Edition, American Public Health Association, 2005.
22. E. W. Yemm and A. J. Willis, *Biochem. J.*, 1954, 57, 508-514.
23. P. K. Smith, R. I. Krohn, G. T. Hermanson, A. K. Mallia, F. H. Gartner, M. D. Provenzano, E. K. Fujimoto, N. M. Goeke, B. J. Olson and D. C. Klenk, *Anal. Biochem.*, 1985, 150, 76-85.
24. A. Klindworth, E. Pruesse, T. Schweer, J. Peplies, C. Quast, M. Horn and F. O. Glockner, *Nucleic Acids Res.*, 2013, 41.
25. T. Magoc and S. L. Salzberg, *Bioinformatics*, 2011, 27, 2957-2963.
26. J. G. Caporaso, J. Kuczynski, J. Stombaugh, K. Bittinger, F. D. Bushman, E. K. Costello, N. Fierer, A. G. Pena, J. K. Goodrich, J. I. Gordon, G. A. Huttley, S. T. Kelley, D. Knights, J. E. Koenig, R. E. Ley, C. A. Lozupone, D. McDonald, B. D. Muegge, M. Pirrung, J. Reeder, J. R. Sevinsky, P. J. Tumbaugh, W. A. Walters, J. Widmann, T. Yatsunenko, J. Zaneveld and R. Knight, *Nat. Methods*, 2010, 7, 335-336.
27. R. C. Edgar, *Bioinformatics*, 2010, 26, 2460-2461.
28. J. G. Caporaso, K. Bittinger, F. D. Bushman, T. Z. DeSantis, G. L. Andersen and R. Knight, *Bioinformatics*, 2010, 26, 266-267.
29. B. J. Haas, D. Gevers, A. M. Earl, M. Feldgarden, D. V. Ward, G. Giannoukos, D. Ciulla, D. Tabbaa, S. K. Highlander, E. Sodergren, B. Methe, T. Z. DeSantis, J. F. Petrosino, R. Knight, B. W. Birren and H. M. Consortium, *Genome Res.*, 2011, 21, 494-504.
30. C. Quast, E. Pruesse, P. Yilmaz, J. Gerken, T. Schweer, P. Yarza, J. Peplies and F. O. Glockner, *Nucleic Acids Res.*, 2013, 41, D590-D596.
31. P. J. McMurdie and S. Holmes, *PLoS One*, 2013, 8.
32. Barter R L, Yu B. Superheat: An R package for creating beautiful and extendable heatmaps for visualizing complex data. *J Comput Graph Stat.* 2018; 27(4):910-922.
33. R. C. Edgar, *Nucleic Acids Res.*, 2004, 32, 1792-1797.
34. A. Stamatakis, *Bioinformatics*, 2014, 30, 1312-1313.
35. Pinheiro, J. (2017). Package 'nlme'. Retrieved from cran.r-project.org/web/packages/nlme/nlme.pdf.
36. R. B. O. H. R. Minchin, Gavin L. Simpson, Peter Solymos, M. Henry H. Stevens, Eduard Szoecs and Helene and Wagner, vegan: Community Ecology Package. R package version 2.4-1., CRAN.R-project.org/package=vegan).
37. A. Kumar and S. Sokhansanj, *Bioresour. Technol.*, 2007, 98, 1033-1044.
38. S. Sokhansanj, S. Mani, A. Turhollow, A. Kumar, D. Bransby, L. Lynd and M. Laser, Biofuels, *Bioproducts and Biorefining*, 2009, 3, 124-141.
39. W. D. Seider, J. D. Seader, D. R. Lewin and S. Widagdo, Product and process design principles: synthesis, analysis, and evaluation., John Wiley and Sons, Inc., Hoboken, New Jersey, 3rd edn., 2009.
40. Zauba Technologies and Data, Search Import Export Data, www.zauba.com/shipment_search, (accessed Apr. 20, 2017).
41. United States Federal Reserve, Producer Price Index by Commodity for Chemicals and Allied Products: Industrial Chemicals (WPU061), (accessed May 1, 2017).
42. Process Design for Biochemical Conversion of Biomass to Ethanol (2002 and 2011 Design Reports), www.nrel.gov/extranet/biorefinery/aspen_models, (accessed Mar. 3, 2017, 2017).
43. Z. X. Wang, J. Zhuge, H. Y. Fang and B. A. Prior, *Biotechnol. Adv.*, 2001, 19, 201-223.
44. S. Austin, W. S. Kontur, A. Ulbrich, J. Z. Oshlag, W. Zhang, A. Higbee, Y. Zhang, J. J. Coon, D. B. Hodge, T. J. Donohue and D. R. Noguera, *Environ. Sci. Technol.*, 2015, 49, 8914-8922.
45. S. Ghosh, J. R. Conrad and D. L. Klass, *J. Water Pollut. Control Fed.*, 1975, 47, 30-45.
46. H. Strauber, R. Lucas and S. Kleinsteuber, *Appl. Microbiol. Biotechnol.*, 2016, 100, 479-491.
47. L. A. Kucek, J. J. Xu, M. Nguyen and L. T. Angenent, *Front. Microbiol.*, 2016, 7.
48. S. Ge, J. G. Usack, C. M. Spirito and L. T. Angenent, *Environ. Sci. Technol.*, 2015, 49, 8012-8021.
49. D. Dodd, S. A. Kocherginskaya, M. A. Spies, K. E. Beery, C. A. Abbas, R. I. Mackie and I. K. O. Cann, *J. Bacteriol.*, 2009, 191, 3328-3338.
50. B. S. Jeon, O. Choi, Y. Um and B. I. Sang, Biotechnology for Biofuels, 2016, 9.
51. J. Bleckwedel, L. C. Teran, J. Bonacina, L. Saavedra, F. Mozzi and R. R. Raya, *Genome Announc*, 2014, 2.
52. S. Roos, F. Karner, L. Axelsson and H. Jonsson, *Int. J. Syst. Evol. Microbiol.*, 2000, 50 Pt 1, 251-258.
53. M. Kleerebezem, J. Boekhorst, R. van Kranenburg, D. Molenaar, O. P. Kuipers, M. R. Leer, R. Tarchini, S. A. Peters, H. M. Sandbrink, M. W. Fiers, W. Stiekema, R. M. Lankhorst, P. A. Bron, S. M. Hoffer, M. N. Groot, R. Kerkhoven, M. de Vries, B. Ursing, W. M. de Vos and R. J. Siezen, *Proc. Natd. Acad. Sci. U.S.A.*, 2003, 100, 1990-1995.
54. S. H. Chao, M. Sasamoto, Y. Kudo, J. Fujimoto, Y. C. Tsai and K. Watanabe, *Int. J. Syst. Evol. Microbiol.*, 2010, 60, 2903-2907.
55. Y. Zhang and P. V. Vadlani, *J. Biosci. Bioeng.*, 2015, 119, 694-699.
56. A. Garde, G. Jonsson, A. S. Schmidt and B. K. Ahring, *Bioresour. Technol.*, 2002, 81, 217-223.
57. F. Dellaglio, M. Vancanneyt, A. Endo, P. Vandamme, G. E. Felis, A. Castioni, J. Fujimoto, K. Watanabe and S. Okada, *Int. J. Syst. Evol. Microbiol.*, 2006, 56, 1721-1724.
58. J. Krooneman, F. Faber, A. C. Alderkamp, S. J. H. W. O. Elferink, F. Driehuis, I. Cleenwerck, J. Swings, J. C. Gottschal and M. Vancanneyt, *Int. J. Syst. Evol. Microbiol.*, 2002, 52, 639-646.
59. M. D. Collins and S. Wallbanks, *FEMS Microbiol. Lett.*, 1992, 95, 235-240.
60. M. R. Jovita, M. D. Collins, B. Sjoden and E. Falsen, *Int. J. Syst. Bacteriol.*, 1999, 49, 1573-1576.

61. F. E. Dewhirst, B. J. Paster, N. Tzellas, B. Coleman, J. Downes, D. A. Spratt and W. G. Wade, *Int. J. Syst. Evol. Microbiol.*, 2001, 51, 1797-1804.
62. X. Li, R. L. Jensen, O. Hojberg, N. Canibe and B. B. Jensen, *Int. J. Syst. Evol. Microbiol.*, 2015, 65, 1227-1233.
63. T. B. Stanton and D. C. Savage, *Int. J. Syst. Bacteriol.*, 1983, 33, 618-627.
64. S. H. Duncan, G. L. Hold, A. Barcenilla, C. S. Stewart and H. J. Flint, *Int. J. Syst. Evol. Microbiol.*, 2002, 52, 1615-1620.
65. S. H. Duncan, R. I. Aminov, K. P. Scott, P. Louis, T. B. Stanton and H. J. Flint, *Int. J. Syst. Evol. Microbiol.*, 2006, 56, 2437-2441.
66. L. V. Holdeman, C. P. Elizabeth and W. E. C. Moore, *Int. J. Syst. Bacteriol.*, 1967, 17, 323-341.
67. Z. L. Tian, G. R. Mohan, L. Ingram and P. Pullammanappallil, *Bioresour. Technol.*, 2013, 144, 387-395.
68. N. Nasr, E. Elbeshbishy, H. Hafez, G. Nakhla and M. H. El Naggar, *Bioresour. Technol.*, 2012, 111, 122-126.
69. R. Hegner, C. Koch, V. Riechert and F. Harnisch, *Rsc Adv*, 2017, 7, 15362-15371.
70. P. Devarapalli, N. Deshpande and R. R. Hirwani, *Biofuel Bioprod Bior*, 2016, 10, 534-541.
71. B. Xiong, T. L. Richard and M. Kumar, *J. Membr. Sci.*, 2015, 489, 275-283.
72. P. J. Weimer, M. Nerdahl and D. J. Brandl, *Bioresour. Technol.*, 2015, 175, 97-101.
73. S. Liang and C. Wan, *Bioresour. Technol.*, 2015, 182, 179-183.

Example 2. Metatranscriptomic and Thermodynamic Insights into Medium-Chain Fatty Acid Production Using an Anaerobic Microbiome Summary Biomanufacturing from renewable feedstocks can offset fossil fuel-based chemical production. One potential biomanufacturing strategy is production of medium-chain fatty acids (MCFA) from organic feedstocks using either pure cultures or microbiomes. While the set of microbes in a microbiome can often metabolize more diverse organic materials than a single species, and the role of specific species may be known, knowledge of the carbon and energy flow within and between organisms in MCFA producing microbiomes is only starting to emerge. Here, we integrate metagenomic, metatranscriptomic, and thermodynamic analyses to predict and characterize the metabolic network of an anaerobic microbiome producing MCFA from organic matter derived from lignocellulosic ethanol fermentation conversion residue. A total of 37 high quality (>80% complete, <10% contamination) metagenome-assembled genomes (MAGs) were recovered from the microbiome and metabolic reconstruction of the 10 most abundant MAGs was performed. Metabolic reconstruction combined with metatranscriptomic analysis predicted that organisms affiliated with *Lactobacillus* and *Coriobacteriaceae* degraded carbohydrates and fermented sugars to lactate and acetate. *Lachnospiraceae* and *Eubacteriaceae* affiliated organisms were predicted to transform these fermentation products to MCFA. Thermodynamic analyses identified conditions in which $H_2$ is expected to be either produced or consumed, suggesting a potential role of $H_2$ partial pressure on MCFA production. From an integrated systems analysis perspective, we propose that MCFA production could be improved if microbiomes are engineered to use homofermentative instead of heterofermentative *Lactobacillus*, and if MCFA-producing organisms are engineered to preferentially use a thioesterase instead of a CoA transferase as the terminal enzyme in reverse β-oxidation.

Introduction

Biological production of chemicals from renewable resources is an important step to reduce societal dependence on fossil fuels. One approach that shows potential for the biological production of chemicals from renewable resources, the carboxylate platform,[1,2] uses anaerobic microbial communities to bio-transform complex substrates into carboxylic acids, including medium-chain fatty acids (MCFAs). MCFAs such as hexanoate (a six carbon monocarboxylate, C6) and octanoate (an eight carbon monocarboxylate, C8) are used in large quantities for the production of pharmaceuticals, antimicrobials, and industrial materials, and can be processed to chemicals currently derived from fossil fuels.[3,4]

Previous applications of the carboxylate platform have focused on converting organics from undistilled corn beer,[5,6] food,[7,8] winery residue,[9] thin stillage from corn ethanol production,[10] and lignocellulose-derived materials[11-13] to MCFAs, and as we have shown for lignocellulosic biofuel production,[4] one can anticipate economic benefits from converting organic residues from these industries into MCFAs.

MCFA producing bioreactors contain diverse microbial communities.[4,5,12] While the roles of some community members in these microbiomes can be inferred from studies with pure cultures and from phylogenetic relationships,[10,12,14,15] detailed knowledge of specific metabolic activities in many members of these microbiomes is only starting to emerge.[16] In general, some community members participate in hydrolysis and fermentation of available organic substrates, while others are involved in the conversion of intermediates to MCFAs via reverse β-oxidation, a process also known as chain elongation.[1] In reverse β-oxidation, an acyl-CoA unit is combined with acetyl-CoA, with each cycle elongating the resulting carboxylic acid by two carbons.[1] Energy conservation in organisms using reverse β-oxidation as the main metabolic process for growth relies on ATP generation with reduced ferredoxin, which is generated through both pyruvate ferredoxin oxidoreductase and an electron bifurcating acyl-CoA dehydrogenase.[17] A proton translocating ferredoxin, NAD reductase, is used to reduce NAD with ferredoxin and create an ion motive force which is used to generate ATP.[17] The even-chain butyric (C4), hexanoic (C6), and octanoic (C8) acids are all potential products of reverse β-oxidation when the process is initiated with acetyl-CoA. The odd-chain valeric (C5) and heptanoic (C7) acids are products of reverse β-oxidation when the chain elongation process starts with propionyl-CoA. While there are demonstrations of this wide range of possible products from chain elongation,[5,18] and MCFA-producing bioreactors typically produce more than one product,[4,12,14,15,19,20] a strategy to control the final product length has not yet emerged. We are interested in obtaining the knowledge needed for the rational development and implementation of strategies to improve MCFA yields and control product formation in MCFA-producing microbiomes.

In the previous example we showed a bioreactor that produced a mixture of C2, C4, C6 and C8 from lignocellulosic stillage.[4] Based on 16S rRNA tag sequencing, we found that five major genera, three Firmicutes (*Lactobacillus, Roseburia, Pseudoramibacter*) and two Actinobacteria (*Atopobium, Olsenella*), represented more than 95% of the community.[4] Based on the phylogenetic association of these organisms, the *Lactobacillus* and the Actinobacteria were hypothesized to produce lactic acid, while *Roseburia* and *Pseudoramibacter* were hypothesized to produce the even-chain C4, C6, and C8 acids.[4] Furthermore, lactic acid was proposed as the key fermentation product that initiated chain elongation in the microbiome.[4] However, since phylogenetic association is not enough to understand in detail the metabolism of these organisms, the earlier example did not generate sufficient knowledge to help understand how to control a MCFA-producing microbiome.

Here we show further aspects of the MCFA-producing microbiome discussed in Example 1.[4] Se utilized a combination of metagenomic, metatranscriptomic, and thermodynamic analyses to reconstruct the combined metabolic activity of the microbial community. We analyzed the gene expression patterns of the ten most abundant community members during steady-state reactor operation. Our results identify several community members that expressed genes predicted to be involved in complex carbohydrate degradation and in the subsequent fermentation of degradation products to lactate and acetate. Genes encoding enzymes for reverse β-oxidation were expressed by two abundant organisms affiliated with the class *Clostridia*. Based on a thermodynamic analysis of the proposed MCFA-producing pathways, we predict that individual Clostridial organisms use different substrates for MCFA production (lactate, versus a combination of xylose, $H_2$, and acetate). We also show that, under certain conditions, production of MCFA provides energetic benefits compared to production of butyrate, thus generating hypotheses for how to control the final products of chain elongation. This knowledge lays a foundation to begin addressing how to engineer and control MCFA producing microbiomes.

Results

Microbiome Characterization

Figure 6A:
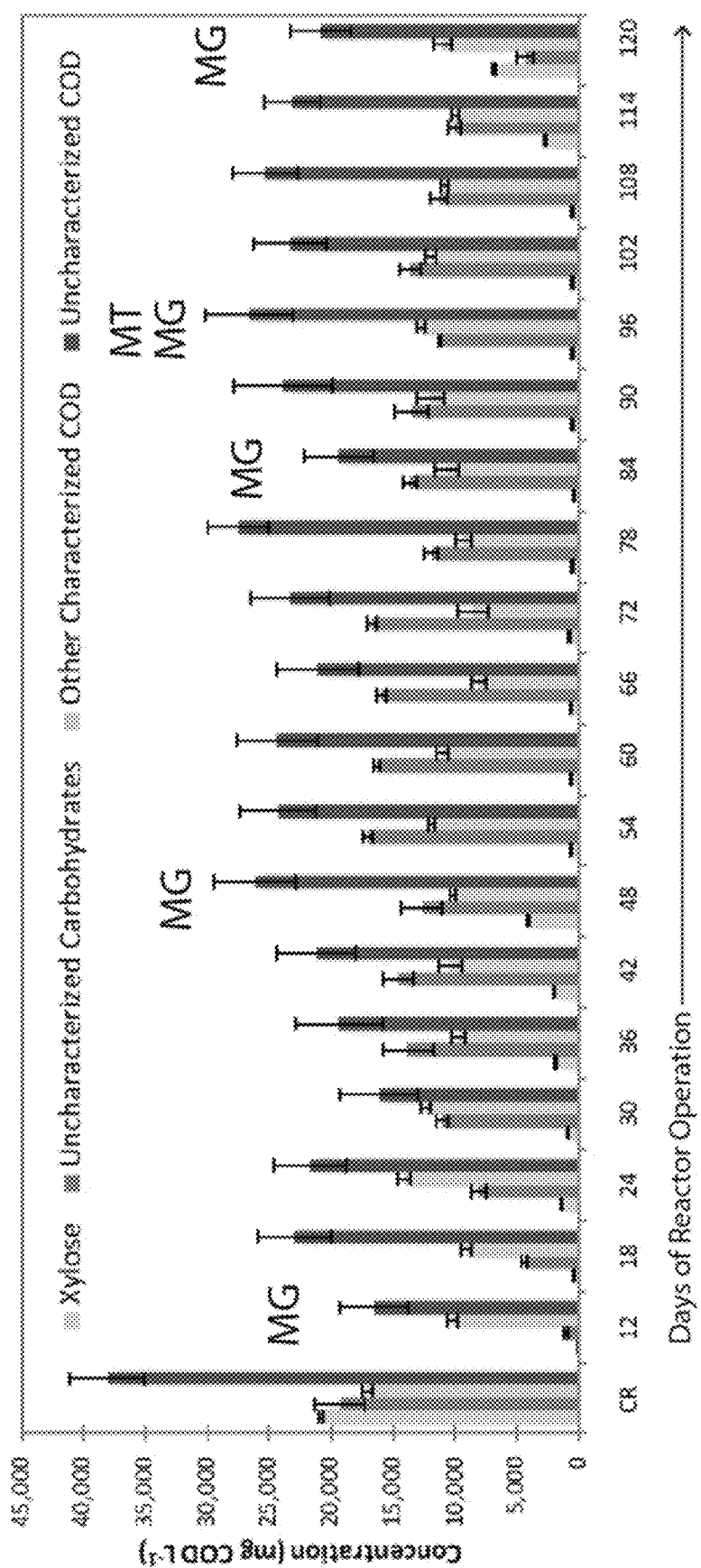
FIGS. 6A-6C Transformation of materials in lignocellulosic ethanol conversion residue by an anaerobic microbiome (FIGS. 6A and 6B) and abundance of metagenome-assembled genomes (MAGs) (FIG. 6C). During 120 days of reactor operation, compounds in conversion residue (CR) (i.e., stillage) were converted to medium-chain fatty acids. For FIGS. 6A and 6B, the first set of bars in the figure describe concentrations in the feed (CR), whereas the rest of the bars describe concentrations in the reactor. A more detailed description of the operation of this reactor is presented elsewhere[4]. Samples were taken for metagenomic (MG) analysis from five timepoints (Day 12, Day 48, Day 84, Day 96, and Day 120 and for metatranscriptomic analysis (MT) from one time point (Day 96). Overall, the bioreactor transformed xylose, uncharacterized carbohydrates and uncharacterized COD to acetic (C2), butyric (C4), hexanoic (C6) and octanoic (C8) acids. The microbial community was enriched in 10 MAGs.
Figure 6B:
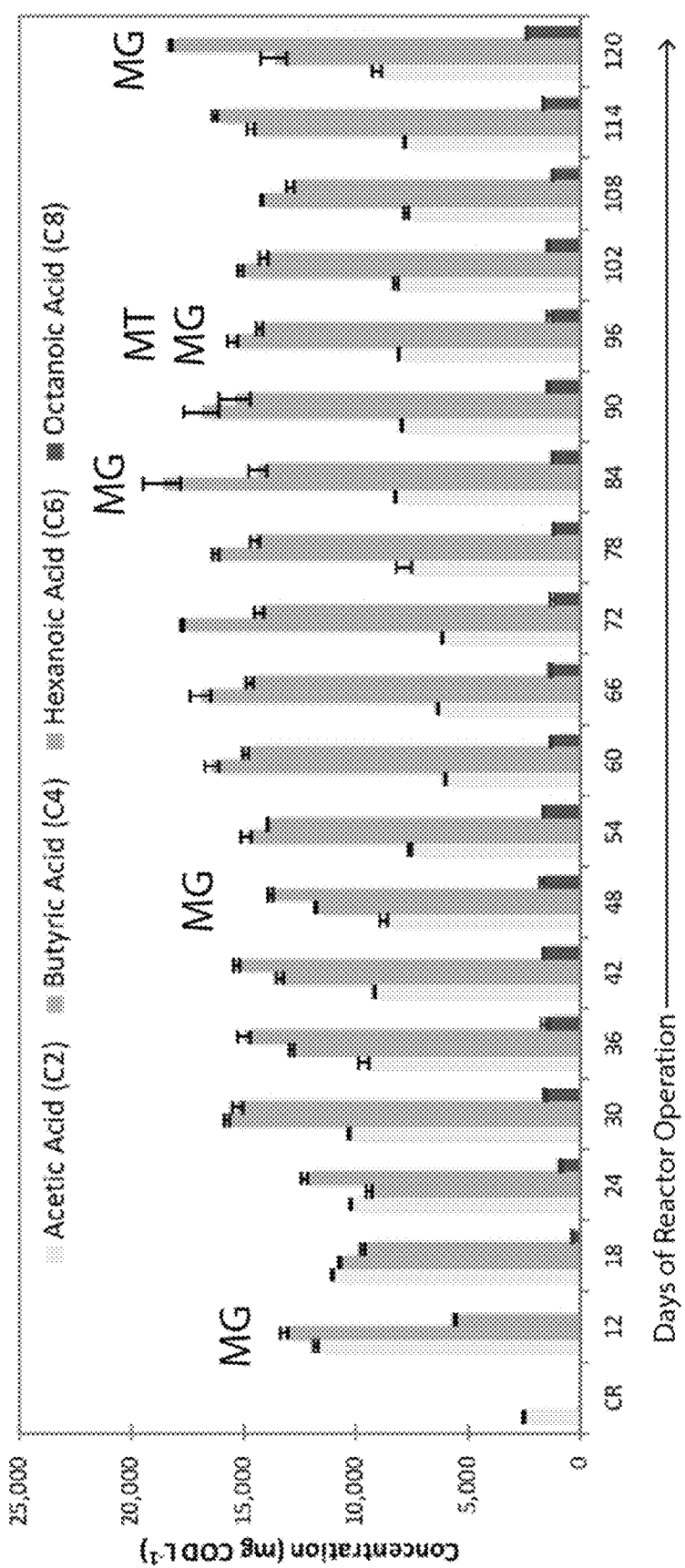
Figure 6C:
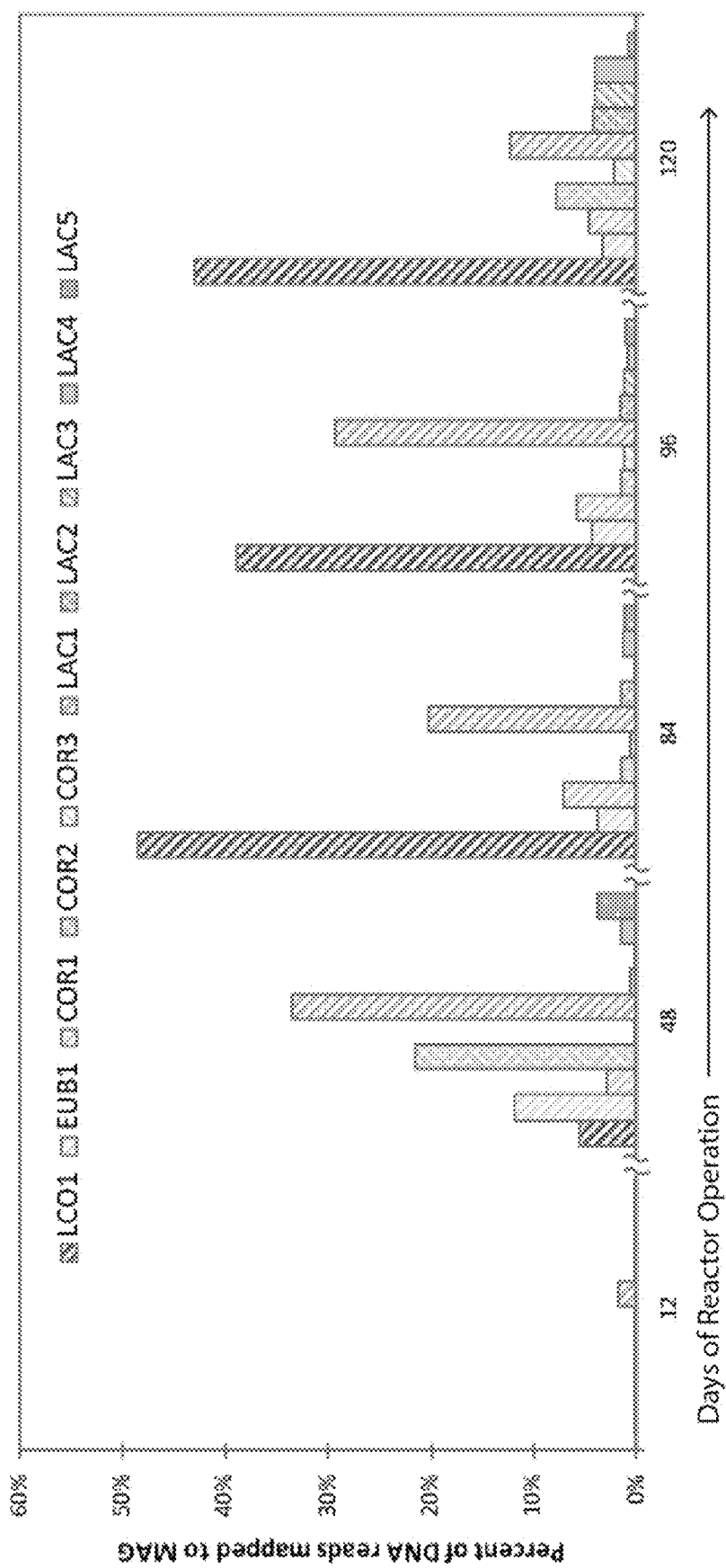

We previously described the establishment of a microbiome that produces MCFA in a bioreactor that is continuously fed with the residues from lignocellulosic ethanol production.[4] The reactor feed, identified as conversion residue (CR) in FIGS. 6A-6C, contained high amounts of xylose, carbohydrate oligomers, and uncharacterized organic matter. To gain insight into the microbial activities that were associated with this MCFA-producing microbiome, samples were collected for metagenomic analysis at five different times (Days 12, 48, 84, 96, and 120), and RNA was prepared for metatranscriptomic analysis at Day 96. At the time of metatranscriptomic sampling, the bioreactor converted 16.5% of the organic matter (measured as chemical oxygen demand (COD)) in conversion residue to C6 and C8. During the period of reactor operation described in FIGS. 6A-6C, the bioreactor converted 16.1±3.1% of COD to C6 and C8, and, therefore, Day 96 is representative of the overall reactor performance.

Figure 7:
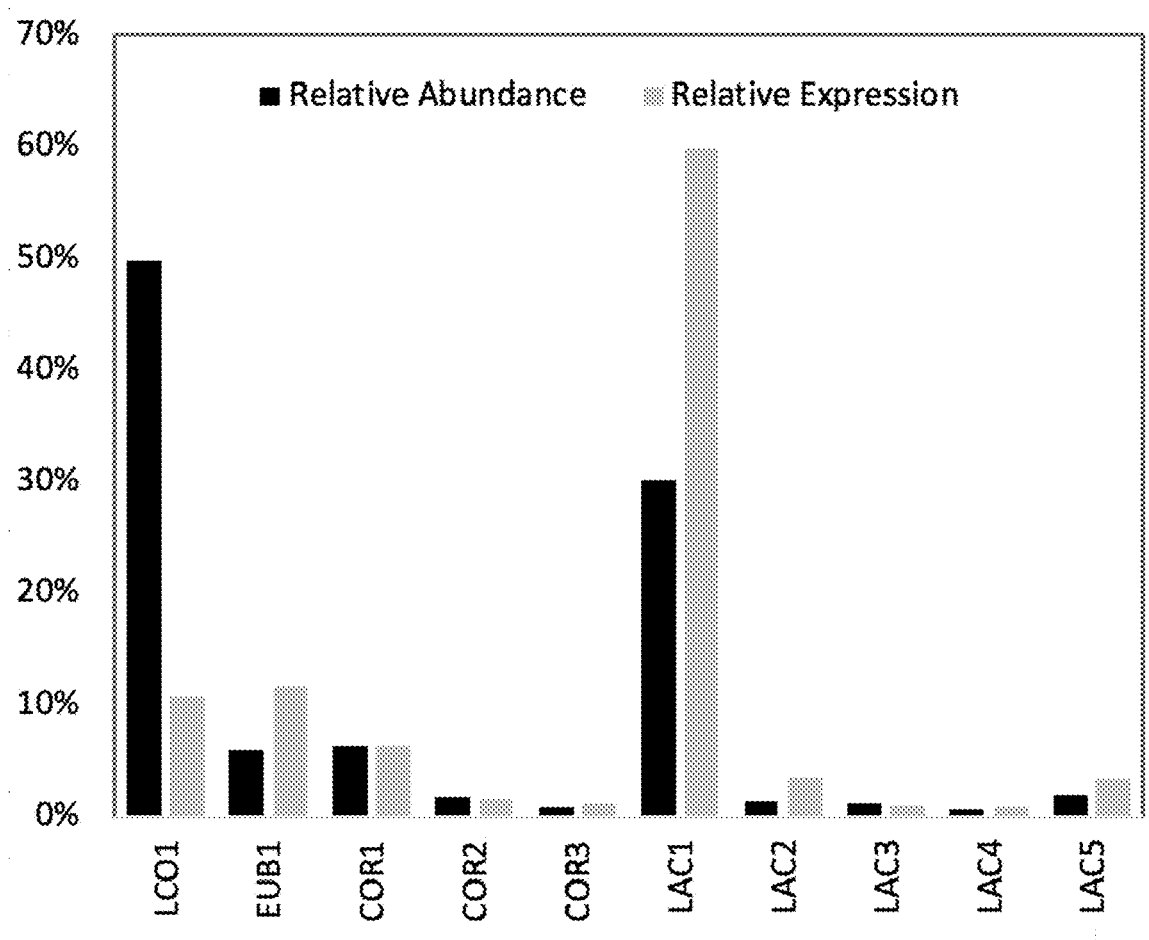
FIG. 7. Relative abundance and expression of the 10 most abundant MAGs in the bioreactor at Day 96. Relative abundance was determined by mapping DNA sequencing reads to the MAG and normalizing to the length of the MAG genome. Relative transcript abundance (expression) was determined by mapping c-DNA sequencing reads to the MAG and normalizing to the length of the MAG genome.

From the metagenomic samples, a total of 219 million DNA reads were assembled and binned, resulting in 37 high quality (>80% complete, <10% contamination) MAGs (see Scarborough and Lawson et al. 2018, which is incorporated herein by reference, at Supplementary Data File 1). MAGs are the collection of genes that were assembled into contigs and represent the population of organisms associated with this collection. For the Day 96 sample, 86% of the DNA reads mapped to the ten most abundant MAGs (Table 4), and each individual MAG mapped more than 0.9% of the DNA reads or more than 0.9% of the cDNA reads (see Scarborough and Lawson et al. 2018, which is incorporated herein by reference, at Supplementary Data File 2). Abundance of the top 10 MAGs was calculated from the percent of the total DNA reads from each time point mapped to the MAGs (FIG. 6C). For the Day 96 sample, relative abundance and expression were compared (FIG. 7; see also Scarborough and Lawson et al. 2018, which is incorporated herein by reference, at Supplementary Data File 2). The most abundant MAGs include a *Lachnospiraceae* (LCO1, 50%), a *Lactobacillus* (LAC1, 30%), a *Coriobacteriacea* (COR1, 6.3%), and a *Eubacteriaceae* (EUB1, 6.0%). Four additional *Lactobacilli* and two additional *Coriobacteriacea* are also predicted to be within the 10 most abundant MAGs (FIG. 7). The other MAGs corresponded to Firmicutes (17 MAGs), Actinobacteria (4 MAGs), Tenericutes (3 MAGs), Bacteroidetes (2 MAGs), and Spirochaetes (1 MAG).

TABLE 4

Summary of MAGs obtained from DNA sequence analysis of the reactor microbiome. Taxonomy, completeness, and contamination were estimated with CheckM. Draft genomes were assembled from five independent reactor samples. These MAGs represent the ten most abundant MAGs at Day 96 (FIGS. 6A-6C).

| Bin ID | Taxonomy | Completeness (%) | Contamination (%) | Genome size (bp) | # Scaffolds | N50 | GC (%) | Predicted Genes |
|---|---|---|---|---|---|---|---|---|
| LCO1 | Firmicutes; Clostridia; Clostridiales; Lachnospiraceae; *Shuttleworthia* | 95.4 | 0.0 | 2,106,912 | 44 | 103,964 | 45.7 | 1,900 |
| EUB1 | Firmicutes; Clostridia; Clostridiales; Eubacteriaceae; *Pseudoramibacter* | 97.8 | 0.2 | 2,002,609 | 35 | 142,846 | 51.2 | 1,857 |
| COR1 | Actinobacteria; Actinobacteria; Coriobacteriales; Coriobacteriaceae; *Olsenella* | 99.2 | 0.8 | 2,512,349 | 225 | 22,880 | 59.0 | 2,358 |
| COR2 | Actinobacteria; Actinobacteria; Coriobacteriales; Coriobacteriaceae; *Olsenella* | 100 | 1.6 | 2,422,853 | 155 | 34,678 | 64.8 | 2,185 |

TABLE 4-continued

Summary of MAGs obtained from DNA sequence analysis of the reactor microbiome. Taxonomy, completeness, and contamination were estimated with CheckM. Draft genomes were assembled from five independent reactor samples. These MAGs represent the ten most abundant MAGs at Day 96 (FIGS. 6A-6C).

| Bin ID | Taxonomy | Completeness (%) | Contamination (%) | Genome size (bp) | # Scaffolds | N50 | GC (%) | Predicted Genes |
|---|---|---|---|---|---|---|---|---|
| COR3 | Actinobacteria; Actinobacteria; Coriobacteriales; Coriobacteriaceae; Olsenella | 98.4 | 7.4 | 3,647,413 | 533 | 13,368 | 55.5 | 4,068 |
| LAC1 | Firmicutes; Bacilli; Lactobacillales; Lactobacillaceae; Lactobacillus | 99.5 | 1.1 | 2,633,889 | 18 | 640,122 | 43.6 | 2,567 |
| LAC2 | Firmicutes; Bacilli; Lactobacillales; Lactobacillaceae; Lactobacillus | 99.4 | 1.6 | 3,179,174 | 79 | 122,889 | 40.5 | 2,989 |
| LAC3 | Firmicutes; Bacilli; Lactobacillales; Lactobacillaceae; Lactobacillus | 99.2 | 1.4 | 2,704,063 | 174 | 29,509 | 43.0 | 2,731 |
| LAC4 | Firmicutes; Bacilli; Lactobacillales; Lactobacillaceae; Lactobacillus | 98.9 | 1.3 | 3,335,227 | 95 | 86,779 | 40.2 | 3,150 |
| LAC5 | Firmicutes; Bacilli; Lactobacillales; Lactobacillaceae; Lactobacillus | 80.1 | 0.8 | 1,487,044 | 181 | 12,363 | 46.1 | 1,524 |

Figure 8:
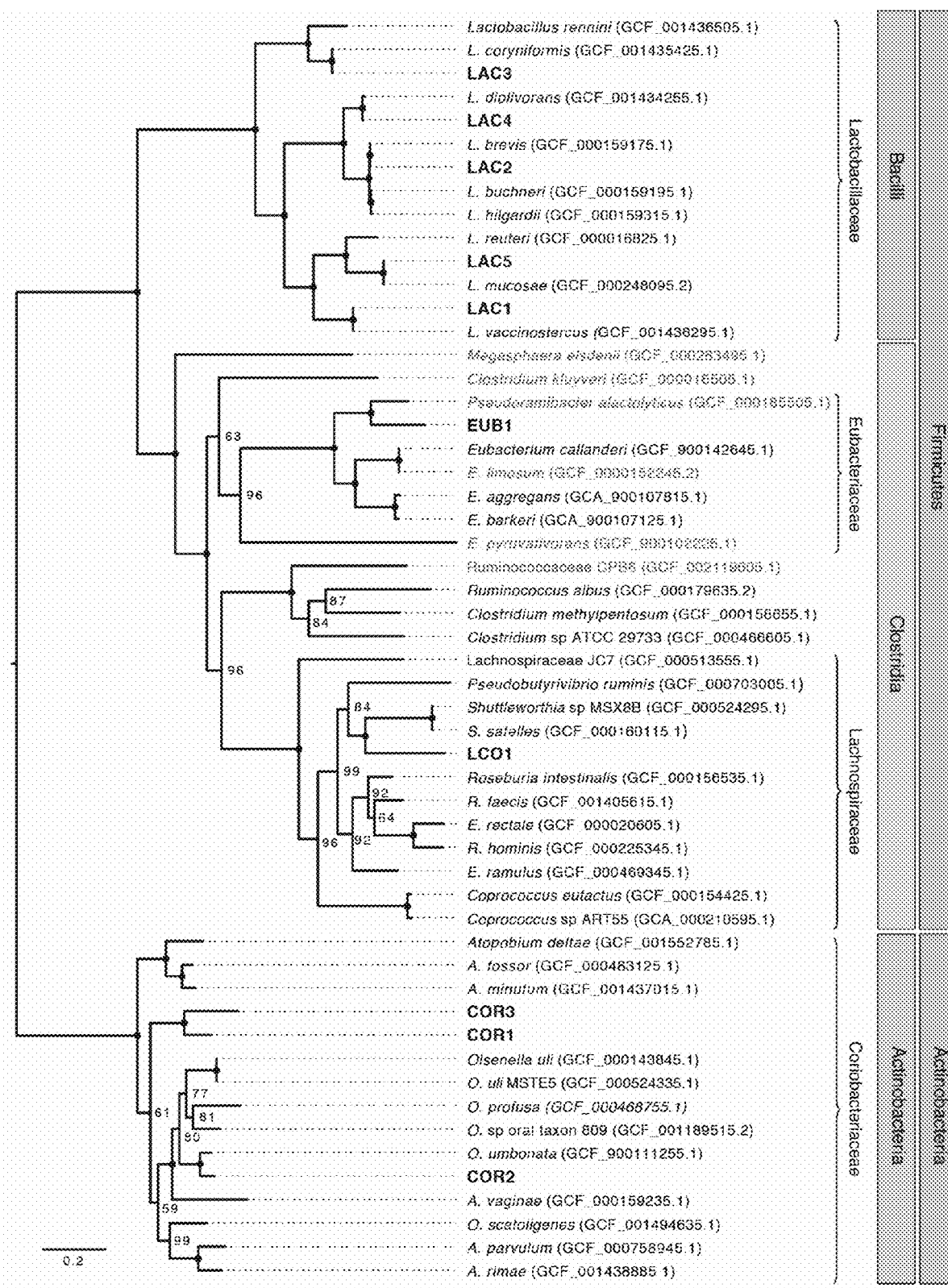
FIG. 8. Phylogenetic analysis for ten MAGs obtained from reactor biomass. Draft genomes from this example are shown in bold text. Red text indicates an organism that has been shown to produce MCFA. National Center for Biotechnology Information assembly accession numbers are shown in parentheses. Node labels represent bootstrap support values with solid circles representing a bootstrap support value of 100. The phyla and class of genomes are shown in shaded boxes and families are indicated by brackets. For Actinobacteria genomes, Actinobacteria is both the phylum and class.

The metatranscriptome data, obtained from the Day 96 sample, contained 87 million cDNA reads. After quality checking and removal of rRNA sequences, 82.6 million predicted transcript reads were used for mapping to MAGs. Of these, 85% of the predicted transcripts (hereafter referred to as transcripts or mRNA) mapped back to the 10 most abundant MAGs. Relative expression was calculated from the total filtered mRNA mapped to the MAGs and normalized to the predicted genome length of these bacteria (FIG. 7). MAGs with the highest levels of transcripts included LAC1 (60%), EUB1 (12%), LCO1 (11%), and COR1 (6.3%), which also displayed high abundance in the metagenome (FIG. 8). Whereas LCO1 was most abundant based on DNA reads, LAC1 appeared to have the highest activity based on transcript levels.

A phylogenetic tree of the ten most abundant MAGs was constructed based on concatenated amino acid sequences of 37 single-copy marker genes (FIG. 8).

Genomic Predictions of Chemical Transformations in the Microbiome

A prediction of metabolic networks in the microbiome was performed by analysis of gene annotations or each of the abundant MAGs, whereas expression of the metabolic network was analyzed by mapping mRNA reads to the open reading frames (ORFs) within each of the ten most abundant bacteria. Metabolic reconstruction was performed with automated prediction algorithms[23] and manual curation, particularly of proposed sugar utilization, fermentation and chain elongation pathways.[1] This analysis identified a set of genes that could be used to model the metabolic potential of the microbiome and also a set of genes with high expression levels in the metatranscriptome. These gene sets were used to analyze the metabolic potential of the microbiome to [1] degrade complex carbohydrates remaining in ethanol conversion residue; [2] transform simple sugars into the fermentation products acetate, lactate, and ethanol; and [3] produce butyrate (C4), C6, and C8 from sugars and fermentation products. The predictions for each of these processes are summarized below.

Degradation of complex carbohydrates. Carbohydrates were a large portion of the organic substrates present in the ethanol conversion residue fed to the bioreactor, and uncharacterized carbohydrates. Quantitative analyses indicated that xylose was the most abundant monosaccharide in the residue, accounting for 22% of the organic matter. Glucose was undetected in most samples or a minor component, and other carbohydrates corresponded to 20% of the organic matter in the residue (see CR bar in FIGS. 6A-6C). Approximately 40% of the uncharacterized carbohydrates were being degraded at the time the metatranscriptomic samples were obtained (Day 96; FIGS. 6A-6C).

To investigate the expression of genes related to degradation of complex carbohydrates, we analyzed the predicted MAG ORFs using the carbohydrate-active enzyme (CAZyme) database[24]. Of particular interest was production of predicted extracellular enzymes that hydrolyze glycosidic bonds in complex carbohydrates, as these may release sugars that can be subsequently metabolized by community members that do not express complex carbohydrate degrading enzymes. The subcellular localization software, CELLO, was used to predict whether individual CAZyme proteins were located within the cytoplasm or targeted to the extracellular space [25].

This analysis showed that transcripts encoding genes for several types of glycoside hydrolases (GHs) were abundant in several MAGs in the microbiome (see Scarborough and Lawson et al. 2018, which is incorporated herein by reference, at FIG. 3.S1). All LAC MAGs expressed genes encoding extracellular CAZymes that cleave glycosidic bonds between hexose and pentose moieties in xylans. In particular, LAC1 LAC2, and LAC4 expressed genes that encode several extracellular exo-β-xylosidases that could remove terminal xylose molecules from xylans present in the conversion residue (GH43 and GH120; FIG. S1; Supplement 5). LAC2 also had high levels of transcripts for an exo-α-L-1,5-arabinanase (GH93), predicted to release other pentose sugars from arabinan, which accounts for 3% of the sugar polymers in switchgrass[26,27]. In addition, the COR1, COR3 and LAC4 members of the community had high transcript levels for three extracellular CAZymes (GH13) that are predicted to degrade a variety of glucans that may be remaining in switchgrass conversion residue[28]. In sum, this analysis predicts that at the time of sampling glucans were degraded by populations represented by *Lactobacillus* and *Coriobacteriaceae* MAGs, where the populations represented by the LAC MAGs may also have degraded xylans and arabinans. It further suggests that this microbiome is capable of releasing oligosaccharides and sugar monomers from glucans, xylans, and arabinans, the primary components of switchgrass and other plant biomass. The analysis also predicts that LCO1 and EUB1 are not participating in complex carbohydrate degradation.

Bacterial oligosaccharide hydrolysis can also occur in the cytoplasm. All MAGs in this microbiome contained predicted cytoplasmic GH13 enzymes, which are known to degrade hexose oligosaccharides. The microbiome also contained abundant transcripts for genes encoding predicted cytoplasmic CAZymes that degrade maltose (GH4, GH65), a glucose dimer that may result from extracellular breakdown of glucans (see Scarborough and Lawson et al. 2018, which is incorporated herein by reference, at FIG. 3.S1). Transcripts encoding known or predicted cytoplasmic β-glucosidases (GH1, GH3) and β-galactosidases (GH2) are found across the MAGs (FIG. S1). In addition, transcripts that encode β-xylosidases (GH1, GH3) and α-L-arabinofuranosidases (GH2), are found in all the LAC MAGs except LAC3 (see Scarborough and Lawson et al. 2018, which is incorporated herein by reference, at FIG. 3.S1). Based on the metatranscriptomic analysis, other cytoplasmic CAZymes predicted to hydrolyze pentose-containing oligosaccharides are predicted to be expressed by the LAC1, LAC2, LAC4, and LAC5 members of this microbiome (Scarborough and Lawson et al. 2018, which is incorporated herein by reference, at FIG. 3.S1).

Transport and production of simple fermentation products from sugars. Simple sugars are abundant in ethanol conversion residue and produced during complex carbohydrate hydrolysis. Sugars are therefore expected to be a major substrate for the microbiome. Despite the use of a yeast strain that was engineered for improved xylose utilization in the ethanol fermentation, xylose was the major abundant monosaccharide present in the remaining conversion residue (CR; FIGS. 6A-6C). As discussed above, the relative transcript levels of genes encoding extracellular GHs (see Scarborough and Lawson et al. 2018, which is incorporated herein by reference, at FIG. 3.S1) by several MAGs in the microbiome predict that additional pentoses and hexoses may be released through degradation of complex carbohydrates.

We therefore analyzed the genomic potential of the community to transport sugars, and metabolize them to fermentation products, particularly the known MCFA precursors lactate, acetate, and ethanol. To investigate the ability of the community to transport sugars, MAG ORFs were annotated with the Transporter Classification Database (Supplement 6). Expression of genes associated with the pentose phosphate pathway, phosphoketolase pathways, and glycolysis (see Scarborough and Lawson et al. 2018, which is incorporated herein by reference, at FIG. 3.4A) was analyzed to predict the potential for sugar metabolism within individual MAGs.

This analysis found that transcripts from genes encoding predicted carbohydrate transporters were among the most highly abundant mRNAs across the microbiome, accounting for 5.8% of the total transcripts. These putative transporters belonged to a variety of families, including many associated with the ATP-binding cassette (ABC) superfamily, and the phosphotransferase system (PTS) family (TD 4.A.-) (Scarborough and Lawson et al. 2018, which is incorporated herein by reference, at FIG. 3.S2). LCO1, LAC1, LAC2, and LAC3 are predicted to contain xylose transporters (XylT) (see Scarborough and Lawson et al. 2018, which is incorporated herein by reference, at FIG. 3.4A), while glucose (GluT), fructose (FruT), and other hexose transporters were expressed across the LAC, COR, and LCO MAGs (see Scarborough and Lawson et al. 2018, which is incorporated herein by reference, at FIG. 3.4A and FIG. S2). EUB1 only encoded transcripts encoding carbohydrate transporters for uptake of fructose and sucrose (see Scarborough and Lawson et al. 2018, which is incorporated herein by reference, at FIG. 3.S2). Overall, this analysis predicts that all MAGs have the potential to transport hexose sugars into the cell, while gene expression patterns observed for the LCO1 and the *Lactobacillus* MAGs (excluding LAC3) predicted that at the time of sampling they played a major role in pentose utilization in this microbiome.

We also analyzed the metatranscriptomic data to investigate potential routes for sugar metabolism. Once transported to the cytoplasm, glucose can be phosphorylated with hexokinase (HK) and converted to fructose-6-phosphate (F-6-P) by glucose-6-phosphate isomerase (GI). Transcripts encoding predicted HK and GI enzymes are abundant for all MAGs within the microbiome (see Scarborough and Lawson et al. 2018, which is incorporated herein by reference, at FIG. 3.4A), except LAC5 for which the assembly does not show homologues of these proteins. Fructose utilization starts with phosphorylation during transport (see Scarborough and Lawson et al. 2018, which is incorporated herein by reference, at FIG. 3.4A). Fructose-6-phosphate (F-6-P) is either phosphorylated to fructose-1,6-bisphosphate (F-1,6-BP) by phosphofructokinase (PFK) in glycolysis or is cleaved to acetyl-P (Ac-P) and erythrose-4-P (E-4-P) by phosphoketolase (PK). While LAC1, LAC2, LAC4, LAC5 and COR3 all lack homologues of genes encoding PFK (a highly-conserved glycolysis enzyme known to be a major target for regulatory control in hexose utilization),[29] they all contain transcripts for homologues of PK (FIG. 4a). In sum, these analyses predict that all of the abundant MAGs in this microbiome can utilize hexoses that may be produced during hydrolysis of complex oligosaccharides.

Transcripts predicted to encode enzymes to convert xylose to xylulose-5-phosphate, xylose isomerase (XI) and xylulose kinase (XK),[30] were abundant in most of the *Lactobacillus* MAGs and LCO1, and either absent or showed very low abundance in LAC3, EUB1 and the COR MAGs (see Scarborough and Lawson et al. 2018, which is incorporated herein by reference, at FIG. 3.4A). Once produced, xylulose-5-P can be degraded through either the phosphoketolase pathway or the pentose phosphate pathway. Transcripts from a gene predicted to encode the diagnostic enzyme of the phosphoketolase pathway, phosphoketolase (PK), which splits xylulose-5-P (X-5-P) into acetyl-P (Ac-P) and glyceraldehyde-3-P (G-3-P), were among the most abundant mRNAs in the *Lactobacillus* MAGs and is also present at high levels in LCO1, accounting for 1.5% of the total transcripts (FIG. 4a; Supplement 4). LCO1 and LAC1 also contained transcripts from homologues of all of the genes needed for the pentose phosphate pathway (R5PE, R5PI, TA, TK in FIG. 3.4A of Scarborough and Lawson et al. 2018, which is incorporated herein by reference). Overall, this analysis predicted that multiple routes of pentose utilization could be utilized by the MAGs in this microbiome.

The predicted routes for both hexose and xylose metabolism in this microbiome lead to pyruvate production (see Scarborough and Lawson et al. 2018, which is incorporated herein by reference, at FIG. 3.4A), so we also analyzed how this and other fermentation products might lead to MCFA production in this community. All MAGs contained transcripts encoding lactate dehydrogenase homologues (LDH) (see Scarborough and Lawson et al. 2018, which is incorporated herein by reference, at FIG. 3.4A), an enzyme which reduces pyruvate to lactate. Transcript analysis also predicts that all of the MAGs (except LAC3) can oxidize pyruvate to acetyl-CoA, utilizing either pyruvate dehydrogenase (PDH) or pyruvate flavodoxin oxidoreductase (PFOR) (see Scarborough and Lawson et al. 2018, which is incorporated herein by reference, at FIG. 3.4A). All MAGs (except EUB1) contain transcripts encoding homologues of acetate kinase (ACK), which converts acetyl-phosphate (Ac-P) to acetate while producing ATP (see Scarborough and Lawson et al. 2018, which is incorporated herein by reference, at FIG. 3.4A). Based on predictions of the gene expression data, the COR and LAC MAGs are also able to convert acetyl-CoA (Ac-CoA) to ethanol with aldehyde dehydrogenase (ADA) and alcohol dehydrogenase (ADH). In summary, analysis of the gene expression patterns in the conversion residue microbiome predicts that the MAGs in the LCO, LAC and COR ferment sugars to acetate and lactate, while the LAC and COR members produce ethanol as an additional fermentation product.

Elongation of fermentation products to MCFAs. Based on the above findings, we analyzed the microbiome gene expression data to predict which members of the microbiome had the potential for conversion of predicted fermentation products to MCFA. The *Clostridia* (LCO1 and EUB1) are the only MAGs that contained genes encoding homologues of genes known to catalyze chain elongation reactions in the reverse β-oxidation pathway (see Scarborough and Lawson et al. 2018, which is incorporated herein by reference, at FIG. 3.4B). Thus, the subsequent analysis is based on the prediction that only LCO1 and EUB1 are the major producers of MCFA in this microbiome. Furthermore, based on the analysis of sugar utilization above, we predict that LCO1 is the only microorganism in the community that can directly utilize sugars for MCFA production.

Acetate, lactate and ethanol, are all fermentation products that would require transformation to acetyl-CoA before being used as a substrate for elongation by the reverse β-oxidation pathway. Acetate could be converted to acetyl-CoA utilizing ATP via acetyl-CoA synthase (ACS) or the ACK and phosphate acetyltransferase (PTA) route (see Scarborough and Lawson et al. 2018, which is incorporated herein by reference, at FIG. 3.4B). Alternatively, acetate can be converted to acetyl-CoA with a CoA transferase (CoAT) which transfers a CoA from one carboxylic acid to another (e.g., from butyryl-CoA to acetate, producing butyrate and acetyl-CoA) (FIG. 4b). Genes encoding homologues of ACS and ACK were not found in EUB1, but LCO1 contained abundant transcripts that encoded homologues of both ACK and PTA (see Scarborough and Lawson et al. 2018, which is incorporated herein by reference, at FIG. 3.4A). Both MAGs also contained transcripts predicted to encode CoAT enzymes (see Scarborough and Lawson et al. 2018, which is incorporated herein by reference, at FIG. 3.4B). Taken together, this analysis predicts that acetate may be used as a substrate for MCFA production by LCO1 and EUB1.

Lactate has been proposed as a key intermediate in other microbiomes producing MCFA.[12] While transcripts encoding genes for lactate production were abundant in the microbiome (see Scarborough and Lawson et al. 2018, which is incorporated herein by reference, at FIG. 3.4A), lactate did not accumulate to detectable levels during steady operation, but transiently accumulated when the bioreactor received a higher load of conversion residue.[4] Transcripts for a gene encoding a predicted lactate transporter (LacT) were abundant in EUB1. In addition, the assembly of LCO1 did not reveal the presence of lactate transporter genes in this MAG, suggesting that only EUB1 may utilize the lactate produced by other MAGs. Neither EUB1 nor LCO1 accumulated transcripts encoding a predicted ADA homologue, which would be required for conversion of acetaldehyde to acetyl-CoA during utilization of ethanol (see Scarborough and Lawson et al. 2018, which is incorporated herein by reference, at FIG. 3.4B). This indicates that if ethanol is produced in this microbiome, it is not used as a significant substrate for MCFA production. Moreover, since ethanol did not accumulate in the reactor during either steady state operation (FIGS. 6A-6C) or after a high load of conversion residue,[4] we predict that ethanol is not a substrate for MCFA production in this microbiome. Rather, based on the predicted activity of LAC and COR MAGs producing lactate and that of EUB1 consuming lactate, we predict that lactate is a key fermentation intermediate for MCFA production.

Within the reverse β-oxidation pathway (FIG. 4b), a key enzyme is an electron-bifurcating acyl-CoA dehydrogenase (ACD) containing two electron transfer flavoproteins (EtfA, EtfB) that pass electrons from NADH to ferredoxin (see Scarborough and Lawson et al. 2018, which is incorporated herein by reference, at FIG. 3.4B).[31] This electron bifurcating complex has been recognized as a key energy conserving mechanism in strictly anaerobic bacteria and archaea[17, 31] and studied in detail in butyrate producing anaerobes.[32, 33] Transcripts for genes encoding a homologue of the acyl-CoA dehydrogenase complex (ACD, EtfA, EtfB) were abundant in both LCO1 and EUB1, as are those from other genes predicted to be involved in this pathway (see Scarborough and Lawson et al. 2018, which is incorporated herein by reference, at FIG. 3.4B). Chain elongation by the reverse β-oxidation pathway conserves energy by increasing the ratio of reduced ferredoxin (a highly electropositive electron carrier) to the less electropositive NADH.[1] In organisms that use this pathway, oxidation of ferredoxin by the RNF complex generates an ion motive force, and ATP synthase utilizes the ion motive force to produce ATP.[17] We found that transcripts for genes encoding homologues of all six subunits of the RNF complex were abundant in both EUB1 and LCO1 (RnfABCDEG, FIG. 3.4B in Scarborough and Lawson et al. 2018, which is incorporated herein by reference). To maintain cytoplasmic redox balance, reduced ferredoxin could transfer electrons to $H^{30}$ via hydrogenase, generating $H_2$. LCO1 and EUB1, along with the COR MAGs, contained abundant transcripts for genes predicted to produce ferredoxin hydrogenase (H2ase, FIG. 3.4B in Scarborough and Lawson et al. 2018, which is incorporated herein by reference), supporting the hypothesis that $H_2$ production plays a role within this MCFA-producing microbiome. We also looked for two additional hydrogenases known to conserve energy either through the translocation of protons (Ech-ABCDEF, FIG. 3.4B in Scarborough and Lawson et al. 2018, which is incorporated herein by reference) or by electron confurcation, utilizing electrons from both NADH and reduced ferredoxin (HydABC, FIG. 3.4B in Scarborough and Lawson et al. 2018, which is incorporated herein by reference).[17] It does not appear that these systems play a major role in $H_2$ production in this microbiome since none of the MAGs contained genes encoding homologues of the known components for either of these enzyme complexes (see Scarborough and Lawson et al. 2018, which is incorporated herein by reference, at FIG. 3.4B).

Thermodynamic Analysis of MCFA Production in the Microbiome

The above analysis predicted several potential routes for MCFA production by LCO1 and EUB1 in this microbiome. To evaluate the implications of these potential chain elongation routes, we used thermodynamic analysis to investigate the energetics of the predicted transformations. For this, we reconstructed metabolic pathways for xylose and lactate conversion, as well as ATP yields based on the data obtained from gene expression analyses (see Scarborough and Lawson et al. 2018, which is incorporated herein by reference, at Tables 3.1-2 and Supplementary Data File 7). Metabolic reconstructions considered xylose (see Scarborough and Lawson et al. 2018, which is incorporated herein by reference, at Table 3.1) and lactate (see Scarborough and Lawson et al. 2018, which is incorporated herein by reference, at Table 3.2) as major substrates for synthesis of C4, C6, and C8 products. In addition, both LCO1 and EUB1 have the potential to use a CoAT or a thioesterase (TE) as the terminal enzyme of the reverse β-oxidation pathway (see Scarborough and Lawson et al. 2018, which is incorporated herein by reference, at FIG. 3.4B), so we considered both possibilities in the thermodynamic analysis. We used these reconstructions to calculate the free energy changes of the overall biochemical reactions assuming an intracellular pH of 7.0, a temperature of 35° C., and $H_2$ partial pressures of $1.0 \times 10^{-6}$, 1.0, and 6.8 atm for low, standard, and high $H_2$ partial pressure, respectively. The low value is the approximate concentration of $H_2$ in water that is in equilibrium with the atmosphere and the high value is an expected maximum in a pressurized mixed culture fermentation system.[34] We also compared the efficiency of ATP production to an expected maximum yield of 1 ATP per −60 kJ energy generated by the overall chemical transformation.[35]

The use of xylose as the substrate (see Scarborough and Lawson et al. 2018, which is incorporated herein by reference, at Table 3.1, Eqs. 3-8) is possible for LCO1 but not EUB1, since the later MAG lacks genes to transport and activate xylose to xylulose-5-P (XylT, XI, XK, FIG. 3.4A in Scarborough and Lawson et al. 2018, which is incorporated herein by reference). Our analysis predicts that, with a pathway containing a terminal CoAT enzyme, the ATP yield (mol ATP $mol^{-1}$ xylose) does not increase if longer chain MCFAs are produced. However, if TE is used for the terminal step of reverse β-oxidation (see Scarborough and Lawson et al. 2018, which is incorporated herein by reference, at Table 3.1, Eqs. 6-8), the overall ATP yield is lower, but it increases with increasing product length, and C8 production provides a 17% increase in ATP yield versus production of C4. This suggests that LCO1 has no energetic benefit for producing C6 or C8 solely from xylose unless TE is used as the terminal enzyme of reverse β-oxidation. Additionally, the higher ATP yield of xylose conversion to C4 (see Scarborough and Lawson et al. 2018, which is incorporated herein by reference, at Table 3.1, Eqs. 3 and 6), in comparison to xylose conversion to lactate and acetate by other members of the microbiome (see Scarborough and Lawson et al. 2018, which is incorporated herein by reference, at Table 3.1, Eq. 2), may explain why LCO1 reached higher abundance in the microbiome compared to the other less abundant MAGs (LAC) that are predicted to ferment xylose to lactate and acetate (FIG. 7). In production of C4 and C8, no $H_2$ is predicted to be formed if a CoAT is utilized (see Scarborough and Lawson et al. 2018, which is incorporated herein by reference, at Table 3.1, Eqs. 3 and 5), whereas $H_2$ production is predicted when C6 is produced (see Scarborough and Lawson et al. 2018, which is incorporated herein by reference, at Table 3.1, Eq. 4). On the other hand, if a TE terminal enzyme is utilized for the reverse β-oxidation, $H_2$ is predicted to be produced for all carboxylic acid products.

Additional metabolic reconstructions analyzed the co-utilization of xylose with a monocarboxylic acid (see Scarborough and Lawson et al. 2018, which is incorporated herein by reference, at Table 3.1, Eq 9-18). This analysis predicted that co-metabolism of these substrates could provide an energetic advantage (i.e., higher mol ATP per mol of xylose) if $H_2$ is utilized as an electron donor. This suggests that $H_2$, produced by either EUB1 or COR MAGs (H2ase, FIG. 5a in Scarborough and Lawson et al. 2018, which is incorporated herein by reference), may be utilized by LCO1 to support MCFA production. If TE is used as the terminal enzyme of reverse β-oxidation (see Scarborough and Lawson et al. 2018, which is incorporated herein by reference, at Table 3.1, Eqs. 14-18), there is no increase in ATP yield versus utilization of xylose as the sole carbon source (see Scarborough and Lawson et al. 2018, which is incorporated herein by reference, at Table 3.1, Eqs. 6-8).

We also modeled MCFA production from lactate by EUB1, since the gene expression data suggested that EUB1 could transform lactate to MCFA. In models utilizing CoAT (see Scarborough and Lawson et al. 2018, which is incorporated herein by reference, at Table 3.2, Eq. 19-21) as a final step in MCFA production, the ATP yield increases as longer chain MCFA are produced, but the free energy released is near the expected limit for ATP production[35] under conditions of low $H_2$ partial pressure and below this limit at high $H_2$ partial pressures (see Scarborough and Lawson et al. 2018, which is incorporated herein by reference, at Table 3.2). If TE is utilized as a final step in MCFA production by EUB1 (see Scarborough and Lawson et al. 2018, which is incorporated herein by reference, at Table 3.2, Eq. 22-24), lower ATP yields are predicted, and in that case the production of longer chain MCFAs has a more pronounced effect on the ATP generated per mol of lactate consumed. For instance, production of C6 results in a 100% increase in the ATP yield compared to producing C4. However, each elongation step reduces the amount of energy released per mol ATP produced, such that production of C8 from lactate results in the release of −58 U per ATP produced under high $H_2$ conditions, which is near the expected limits for a cell to conserve chemical energy as ATP. Overall, the thermodynamic analysis does not unequivocally predict which terminal enzyme may be energetically more advantageous for MCFA production from lactate. While using TE would result in more favorable free energy release than when using CoAT, the predicted ATP yields are lower with TE than with CoAT. We also note that although CoAT transcript abundance was higher than TE transcript abundance (see Scarborough and Lawson et al. 2018, which is incorporated herein by reference, at FIG. 3.4B), expression alone cannot be used as a predictor of which terminal enzyme was primarily used since a kinetic characterization of these enzymes is not available. Regardless, the thermodynamic modeling predicts that, in all conditions, $H_2$ will be produced during lactate elongation (see Scarborough and Lawson et al. 2018, which is incorporated herein by reference, at Table 3.2), and that TE could be a better terminal enzyme to force production of longer chain acids in order to maximize ATP yield (see Scarborough and Lawson et al. 2018, which is incorporated herein by reference, at Table 3.2).

When modeling scenarios utilizing lactate plus carboxylic acids as growth substrates (see Scarborough and Lawson et al. 2018, which is incorporated herein by reference, at Table 3.2, Eqs. 25-36), their elongation by EUB1 would increase the amount of ATP it could produce compared to using lactate only if using a terminal CoAT (see Scarborough and Lawson et al. 2018, which is incorporated herein by reference, at Table 3.2, Eqs. 19-21). $H_2$ production or consumption is not predicted in these scenarios, and the calculated free energy released per mol of ATP produced (−50 to −53 U mol$^{-1}$ ATP) is low, near the physiological limit of −60 U mol$^{-1}$ ATP for energy conservation by the cell. Models with TE as the terminal enzyme in reverse β-oxidation were also analyzed (see Scarborough and Lawson et al. 2018, which is incorporated herein by reference, at Table 3.2, Eqs. 31-36) even though EUB1 is not predicted to have this ability as it lacks ACS and ACK needed to utilize acetate (see Scarborough and Lawson et al. 2018, which is incorporated herein by reference, at FIG. 3.4B). In such models, producing C6 and C8 from lactate plus acetate (see Scarborough and Lawson et al. 2018, which is incorporated herein by reference, at Table 3.2, Eqs. 32-33) is energetically favorable, whereas C4 production is not (see Scarborough and Lawson et al. 2018, which is incorporated herein by reference, at Table 3.2, Eq. 31).

Discussion

Figure 9:
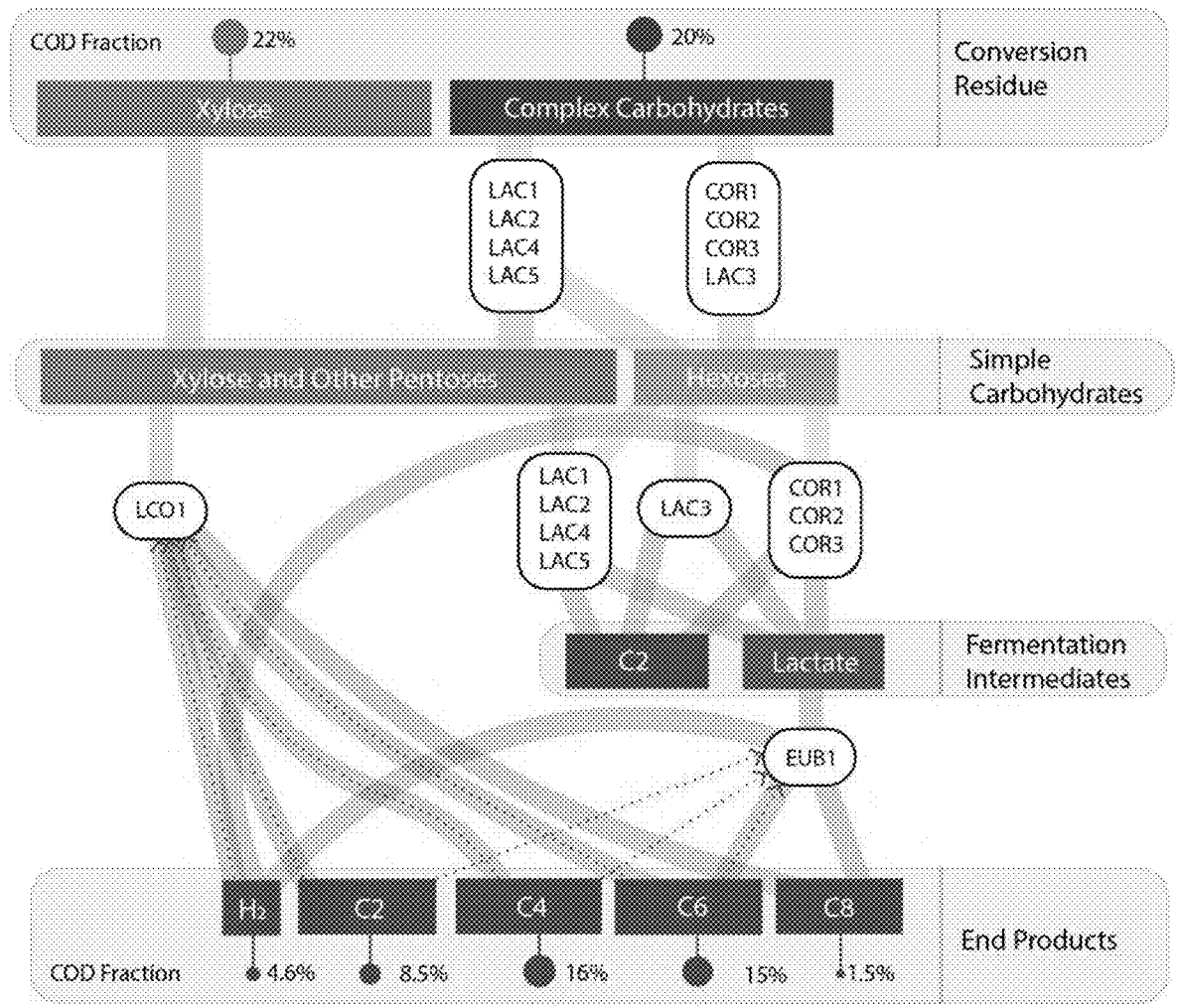
FIG. 9. Predicted transformations of major substrates in conversion residue to medium-chain fatty acids (MCFAs) by this anaerobic microbiome. The microbes in the LAC and COR bins are predicted to produce sugars from complex carbohydrates. Simple carbohydrates, including xylose remaining in conversion residue, are converted to lactate and acetate by *Lactobacillus* (LAC) and *Coriobacteriaceae* (COR) MAGs. The *Lachnospiraceae* (LCO1) MAG converts pentoses directly to butyric acid (C4). The *Eubacteriaceae* (EUB1) produces hexanoic acid (C6) and octanoic acid (C8) from lactate. Further, LCO1 may utilize hydrogen to elongate C2 and C4 to MCFAs, as represented by dashed lines. Additionally, EUB1 may elongate C2, C4 and C6 to C8.

In this example, we illustrate how combining genomic, computational and thermodynamic predictions can illustrate how a microbial community can convert organic substrates in lignocellulosic conversion residues into MCFAs (FIG. 9). Specifically, this approach predicts that the coordinated and step-wise metabolic activity of different members of this microbiome allow cleavage of complex five- and six-carbon containing polysaccharides; conversion of sugars into simple fermentation products; and utilization of sugars and intermediate fermentation products for MFCA production. This approach further predicts the role of intracellular and extracellular reductants in these processes. Below, we illustrate the new insight that has been gained on the activity of a MCFA producing microbiome and how this might relate to other systems.

Our data suggest that the contribution of *Lactobacillus* in this microbiome is in extracellular carbohydrate degradation and subsequent metabolism of pentose- and hexose-containing carbohydrates, while *Coriobacteriaceae* are predicted to metabolize hexose-containing carbohydrates. The combined metabolic activities of these two MAGs would produce oligosaccharides and monomeric sugars that would become available to these and other members of the microbiome. Metabolic reconstruction combined with microbiome transcript levels also suggest that the *Lactobacillus* and *Coriobacteriaceae* MAGs produce fermentation end products, primarily lactate and acetate, from these carbohydrates. *Coriobacteriaceae*, however, are also predicted to produce $H_2$. In addition, microbiome gene expression patterns indicate that two MAGs, EUB1 and LCO1, produce MCFA via reverse β-oxidation. LCO1 is predicted to consume xylose based on gene expression analysis, whereas RNA abundance measurements indicate that EUB1 consumes lactate.

We used thermodynamics to analyze hypothetical scenarios of MCFA production by EUB1 and LCO1. Although the comparison of these hypothetical scenarios did not provide an unequivocal answer to how chain elongation occurs in LCO1 and EUB1, it is helpful to generate hypotheses that could eventually be tested in future research. Our thermodynamic analysis predicts that the most energetically advantageous metabolism for LCO1 (based on ATP production per mol xylose consumed) is the consumption of xylose, $H_2$ and carboxylates to produce C4, C6, and C8 while utilizing CoAT as a terminal enzyme. While xylose is a major component of conversion residue (CR, FIGS. 6A-6C), $H_2$ is expected to be produced by *Coriobacteriaceae* MAGs and EUB1. For EUB1, which is expected to utilize lactate, our analysis predicts that production of MCFA produces higher amounts of ATP, with C6 resulting in a 2-fold increase in ATP production versus producing C4 when consuming lactate as a sole substrate.

Predictions from our thermodynamic modeling indicate that C8 production from lactate is energetically advantageous. However, this is at odds with C6 being produced from conversion residue at higher concentrations than C8 (FIGS. 6A-6C). It is known that C8 is a biocide, so it may be that C8 accumulation is limited by the level of tolerance community members have for this product.[12] It is also possible that higher C6 production indicates a more important role of C6 production by LCO1 without lactate being an intermediate metabolite. It has also been shown that removal of C8 allows for higher productivities of carboxylate platform systems.[1]

$H_2$ production and interspecies $H_2$ transfer are known to have significant impacts on the metabolism of microbial communities.[36] Our analysis predicts a role of $H_2$ in supporting chain elongation in a carboxylate platform microbiome. While high $H_2$ partial pressures are proposed to inhibit production of acetate and other carboxylic acids,[37,38] organisms that use the phosphoketolase pathway (the *Lactobacillus* and LCO1 MAGs identified in this example) can produce C2, C4 and C8 without producing $H_2$ (see Scarborough and Lawson et al. 2018, which is incorporated herein by reference, at Table 3.1, Eqs. 2, 3 and 5). While conversion of lactate to MCFA (see Scarborough and Lawson et al. 2018, which is incorporated herein by reference, at Table 3.2, Eqs. 19-24) is predicted to produce $H_2$, other processes such as co-utilization of xylose and a monocarboxylic acid for MCFA production (see Scarborough and Lawson et al. 2018, which is incorporated herein by reference, at Table 3.1, Eq. 9-18) would consume $H_2$. Therefore, $H_2$ accumulation is not expected to limit production of MCFA, although $H_2$ partial pressures may influence the metabolic routes utilized by the microbiome.

In considering how to further improve the production of MCFA with a microbiome, additional work is needed to characterize and engineer reverse β-oxidation proteins from the Firmicutes in order to improve production of organic acids longer than C4. Further, our data predict that the terminal enzyme of reverse β-oxidation can influence production of MCFA. While a CoAT enzyme results in higher ATP production, a TE makes production of MCFA more energetically advantageous by increasing the ATP yield for production of C6 and C8 compared to C4 (see Scarborough and Lawson et al. 2018, which is incorporated herein by reference, at Tables 3.1-2). Therefore, engineering chain-elongating organisms to only have a TE rather than CoAT may improve production of MCFAs.

Our metabolic reconstructions predict that lactate was a key fermentation product that supports MCFA production. Therefore, strategies to enhance lactate production and minimize other fermentation products (fermentation of carbohydrates to lactate, rather than acetate in this example), could improve production of desired end products. Moreover, designing strategies to enrich a community that produces a critical intermediate like lactate by one pathway (e.g., homofermentative lactate-producing *Lactobacilli*, rather than hetero-fermenters producing both lactate and C2) could improve performance of the microbiome. However, the principles controlling the presence or dominance of heterofermentative versus homofermentative organisms in microbial communities remain largely unexplored. Alternatively, higher production of a desired product, C8, could be achieved by adjusting the abundance or establishing a defined co-culture containing a lactic acid bacterium capable of complex carbohydrate degradation, such as LAC1, and a lactate-elongating organism, such as EUB1. The ability to establish defined synthetic communities, to adjust the abundance of microbiome members or to regulate the metabolic routes within the microbiome may allow more control over the function of a microbiome for production of MCFA or to optimize other traits.

In summary, this example demonstrates that one can dissect and model the composition of microbiomes as a way to understand the contribution of different community members to its function. In the case of an anaerobic carboxylate platform microbiome fed lignocellulosic ethanol conversion residue, two *Clostridia*-related organisms (EUB1 and LCO1) are predicted to be responsible for production of MCFA via reverse β-oxidation. This provides a genome-centric rationale for the previously established correlation between *Clostridia*-related abundance and MCFA production noted in carboxylate platform systems.[4, 12] This example further predicts that the terminal enzyme in product synthesis and the fermentation end products produced by other community members can play a role in determining predominant products of this microbiome. These approaches, concepts and insights should be useful in predicting and controlling MCFA production by reactor microbiomes and in analyzing the metabolic, genomic and thermodynamic factors influencing the function of other microbiomes of health, environmental, agronomic or biotechnological importance.

Methods

Production of conversion residue. Switchgrass used to generate conversion residue was treated by ammonia fiber expansion and enzymatically treated with Cellic CTec3® and Cellic HTec3® (Novozymes) to digest cellulose and hemicellulose (to glucose and xylose, primarily).[39] Hydrolysate was fermented with *Saccharomyces cerevisiae* Y128, a strain with improved xylose utilization.[40] Fermentation media was distilled to remove ethanol.[4]

Bioreactor operation. The bioreactor was seeded with acid digester sludge from the Nine Springs Wastewater treatment plant in Madison, WI. The retention time of the semi-continuous reactor was maintained at six days by pumping conversion residue into the reactor, pumping reactor effluent from the reactor once per hour, and maintaining a liquid volume of 150 mL in the reactor. The reactor was mixed with a magnetic stir bar. The temperature of the reactor was controlled at 35° C. using a water bath, and the pH of the reactor was maintained at 5.5 by feeding 5M KOH through a pump connected to a pH controller. This reactor sustained MCFA production for 252 days.[4]

Metabolite analysis. Samples from the bioreactor and conversion residue were collected for metabolite analysis. All samples were filtered using 0.22 μm syringe filters (ThermoFisher Scientific SLGP033RS, Waltham, MA, USA). Chemical oxygen demand (COD) analysis was performed using High Range COD Digestion Vials (Hach 2125915, Loveland, CO, USA) per standard methods.[41] Soluble carbohydrates were measured with the anthrone method.[42] Glucose, xylose, acetic acid, formic acid, lactic acid, succinic acid, pyruvic acid, glycerol and xylitol were analyzed with high performance liquid chromatography and quantified with an Agilent 1260 Infinity refractive index detector (Agilent Technologies, Inc. Palo Alto, CA) using a 300×7.8 mm Bio-Rad Aminex HPX-87H column with Cation-H guard (BioRad, Inc., Hercules, CA). Acetamide, ethanol, n-propionic acid, n-butyric acid, iso-butyric acid, n-pentanoic acid, iso-pentanoic acid, n-hexanoic acid, iso-hexanoic acid, n-heptanoic acid, and n-octanoic acid were analyzed with tandem gas chromatography-mass spectrometry. An Agilent 7890A GC system (Agilent Technologies, Inc. Palo Alto, CA) with a 0.25 mm Restek Stabilwax DA 30 column (Restek 11008, Belefonte, PA) was used. The GC-MS system was equipped with a Gerstel MPS2 (Gerstel, Inc. Baltimore, MD) auto sampler and a solid-phase micro-extraction gray hub fiber assembly (Supelco, Bellefonte, PA). The MS detector was a Pegasus 4D TOF-MS (Leco Corp., Saint Joseph, MI). Stable isotope labeled internal standards were used for each of the analytes measured with GC-MS.

DNA and RNA sequencing. Biomass samples, consisting of centrifuged and decanted 2 mL aliquots, were collected at Day 12, Day 48, Day 84, Day 96, and Day 120 of reactor operations from initial start-up. Samples were also taken at 96 days and flash-frozen in liquid nitrogen for RNA extraction. For DNA extraction, cells were lysed by incubating in a lysis solution (1.5M sodium chloride, 100 mM trisaminomethane, 100 mM ethylenediamine (EDTA), 75 mM sodium phosphate, 1% cetyltrimethylammonium bromide, and 2% sodium dodecyl sulfate (SDS)), lysozyme (Thermo Fisher Scientific, MA, USA), and proteinase K (New England Biolabs, MA, USA). We then added 500 μL of a 24:24:1 solution of phenol:chloroform:isoamyl alcohol and bead-beat samples for 2 minutes. After bead-beating, biomass was centrifuged at 5,000 rcf for 3 minutes and the entire supernatant was transferred to a 1.5 mL centrifuge tube. Samples were centrifuged again at 12,000 rcf for 10 minutes and the aqueous layer was then removed to a new centrifuge tube. A second phase separation was then performed using chloroform. After centrifuging again and separating the aqueous phase, 500 μL of isopropanol was added to each samples and samples were then incubated at −20 deg C. for 24 hours. Following this incubation, samples were centrifuged at 12,000 rcf for 30 minutes at 4 deg C., decanted, and washed with 70% ethanol. After air-drying the samples, pellets were resuspended in 100 μL of TE buffer and 2 μL of 10 mg/mL RNAse was added to each sample. Samples were incubated for 15 minutes at 37 deg C. We then added 100 uL of a 24:24:1 solution of phenol:chloroform:isoamyl alcohol to each sample and centrifuged at 12,000 rcf for 10 minutes. We separated the aqueous phase to a new centrifuge tube and added 100 Ul of chloroform. Again, samples were centrifuged at 12,000 rcf for 10 minutes and the aqueous phase was separated to a new centrifuge tube. We then added 10 μL of 3M sodium acetate and 250 μL of 95% ethanol to each sample and incubated for 24 hours at −20 deg C. Samples were centrifuged at 12,000 rcf for 30 minutes at 4 deg C. and the pellets were washed with 70% ethanol. After air-drying, pellets were resuspended in 50 uL of TE buffer. After re-suspending the DNA, quantity, purity, and quality were assessed with a Qubit 4 Fluorometer (Thermo Fisher Scientific, MA, USA), a Nanodrop 2000 spectrophotometer (Thermo Fisher Scientific, MA, USA), and gel electrophoresis.

For RNA extraction, cells were lysed by incubating in a lysis solution (20 mM sodium acetate, 1 mM EDTA, and 0.5% SDS prepared in diethylpyrocarbonate-treated water (Invitrogen, CA, USA)) and TRIzol (Invitrogen, CA, USA). The treated cells were subjected to 2 minutes of bead beating using Lysing Matrix A (MP Biomedicals, CA, USA). After this step, successive phase separations with phenol:chloroform:isoamyl alcohol and chloroform were used to separate nucleic acids from additional cell material, as described above. RNA was further purified with an RNEasy Mini Kit (Qiagen, Hilden, Germany) and on-column DNAse 1 (Qiagen, Hilden, Germany) treatment. After re-suspending the RNA, quantity, purity, and quality were assessed with a Qubit 4 Fluorometer (Thermo Fisher Scientific, MA, USA), a Nanodrop 2000 spectrophotometer (Thermo Fisher Scientific, MA, USA), and gel electrophoresis. RNA samples were submitted to the University of Wisconsin Gene Expression Center for quality control with a Bioanalyzer (Agilent, CA, USA), ribosomal RNA reduction with a RiboZero-Bacteria rRNA Removal Kit (Illumina, CA, USA) with a 1 μg RNA input. Strand-specific cDNA libraries were prepared with a TruSeq RNA Library Prep Kit (Illumina, CA, USA).

DNA and RNA were sequenced with the Illumina HiSeq 2500 platform (Illumina, CA, USA). For DNA, an average insert size of 550 bp was used and 2×250 bp reads were generated. For RNA, 1×100 bp reads were generated. Raw DNA and cDNA reads can be found on the National Center for Biotechnology Information (NCBI) website under BioProject PRJNA418244.

Metagenomic assembly, binning, and quality control. DNA sequencing reads were filtered with Sickle using a minimum quality score of 20 and a minimum sequence length of 100.[43] Reads from all five samples were then co-assembled using metaspades and kmer values of 21, 33, 55, 77, 99, and 127.[44] Binning of assembled contigs was performed with MaxBin v2.2.1.[45] The quality, completeness, and contamination of each bin was analyzed with CheckM v1.0.3.[46] Read mapping was performed with BBMAP v35.92 (sourceforge.net/projects/bbmap) to estimate the relative abundance of each bin. Relative abundance was calculated by normalizing the number of mapped reads to the genome size.

Phylogenetic analysis. Phylogeny of the draft genomes was assessed using 37 universal single-copy marker genes with Phylosift v1.0.1.[47] In addition to the draft genomes, 62 publicly-available genomes of related organisms were used to construct a phylogenetic tree. Concatenated amino acid sequences of the marker genes were aligned with Phylosift, and a maximum likelihood phylogenetic tree was constructed with RAxML v8.2.4 with the PROTGAM-MAAUTO model and 100 bootstraps.[48] ANI calculations were performed using JSpecies.[49]

Genome annotations. Draft genomes were annotated with MetaPathways v2.5.[23] Open reading frames (ORFs) were predicted using Prodigal v2.0,[50] and the ORFs were annotated with the following databases: SEED (accessed March 2013), Clusters of Orthologous Groups (COG, accessed December 2013), RefSeq (accessed January 2017), Metacyc (accessed October 2011), and KEGG (accessed January 2017). The LAST algorithim was used for assigning functional annotations.[51] Functional annotations for each MAG are provided in Scarborough and Lawson et al. 2018, which is incorporated herein by reference, at Supplementary Data File 4. Draft genomes were further annotated with the CAZY database.[24] CELLO was used to determine the subcellular location of the CAZYs.[25] Transporters were identified using the Transporter Classification Database.

Transcript analysis. Analysis of transcript data was performed as described in Lawson, et al.[52] cDNA reads were quality filtered as described above for DNA. SortMeRNA was used to remove rRNA sequences using multiple databases for RNA sequences.[53] The remaining non-rRNA sequences were then mapped back to the draft genomes using BBMap v35.92 (sourceforge.net/projects/bbmap) with the minimum sequence identity set to 0.95. Ambiguous reads with multiple top-hit mapping locations were assigned to a random ORF. The number of RNA reads mapping to each ORF was calculated with htseq-count v0.6.1 with the "intersection-strict" parameter.[54] Relative gene expression (RPKM) was calculated for each ORF by normalizing the number of mapped RNA reads for each ORF to the ORF length and the total number of RNA reads mapping back to the genome. The relative RPKM (relPKM) was then calculated as the ratio of the RPKM for the ORF to the median RPKM across the draft genome. Finally, the $\log_2$(relRPKM) was calculated to determine the log-fold difference. As such, a positive number corresponds to greater than median expression levels and a negative number to expression below median levels.

REFERENCES

1. L. T. Angenent, H. Richter, W. Buckel, C. M. Spirito, K. J. J. Steinbusch, C. M. Plugge, D. Strik, T. I. M. Grootscholten, C. J. N. Buisman and H. V. M. Hamelers, *Environ. Sci. Technol.*, 2016, 50, 2796-2810.
2. M. T. Holtzapple and C. B. Granda, Appl. *Biochem. Biotechnol.*, 2009, 156, 95-106.
3. S. Sarria, N. S. Kruyer and P. Peralta-Yahya, *Nat. Biotechnol.*, 2017, 35, 1158-1166.
4. M. J. Scarborough, G. Lynch, M. Dickson, M. McGee, T. J. Donohue and D. R. Noguera, *Biotechnology for Biofuels*, 2018, 11, 200.
5. M. T. Agler, C. M. Spirito, J. G. Usack, J. J. Werner and L. T. Angenent, *Energy Environ. Sci.*, 2012, 5, 8189.
6. S. Ge, J. G. Usack, C. M. Spirito and L. T. Angenent, *Environ Sci Technol*, 2015, 49, 8012-8021.
7. T. I. M. Grootscholten, D. P. B. T. B. Strik, K. J. J. Steinbusch, C. J. N. Buisman and H. V. M. Hamelers, *Applied Energy*, 2014, 116, 223-229.
8. T. I. M. Grootscholten, F. K. dal Borgo, H. V. M. Hamelers and C. J. N. Buisman, *Biomass & Bioenergy*, 2013, 48, 10-16.
9. L. A. Kucek, J. J. Xu, M. Nguyen and L. T. Angenent, *Front. Microbiol.*, 2016, 7.
10. S. J. Andersen, P. Candry, T. Basadre, W. C. Khor, H. Roume, E. Hernandez-Sanabria, M. Coma and K. Rabaey, *Biotechnol Biofuels*, 2015, 8.
11. B. Y. Xiong, T. L. Richard and M. Kumar, *J. Membr. Sci.*, 2015, 489, 275-283.
12. S. J. Andersen, V. De Groof, W. C. Khor, H. Roume, R. Props, M. Coma and K. Rabaey, *Front Bioeng Biotechnol*, 2017, 5, 8.

13. W. R. Kenealy, Y. Cao and P. J. Weimer, *Appl. Microbiol. Biotechnol.*, 1995, 44, 507-513.
14. L. A. Kucek, M. Nguyen and L. T. Angenent, *Water Res.*, 2016, 93, 163-171.
15. X. Zhu, Y. Tao, C. Liang, X. Li, N. Wei, W. Zhang, Y. Zhou, Y. Yang and T. Bo, *Sci. Rep.*, 2015, 5, 14360.
16. W. Han, P. He, L. Shao and F. Lu, *Appl. Environ. Microbiol.*, 2018, DOI: 10.1128/AEM.01614-18.
17. W. Buckel and R. K. Thauer, *Biochim. Biophys. Acta*, 2013, 1827, 94-113.
18. C. M. Spirito, H. Richter, K. Rabaey, A. J. Stams and L. T. Angenent, *Curr. Opin. Biotechnol.*, 2014, 27, 115-122.
19. X. Zhu, Y. Zhou, Y. Wang, T. Wu, X. Li, D. Li and Y. Tao, *Biotechnol Biofuels*, 2017, 10, 102.
20. R. Nelson, D. Peterson, E. Karp, G. Beckham and D. Salvachúa, *Fermentation*, 2017, 3, 10.
21. M. Kim, H. S. Oh, S. C. Park and J. Chun, *Int. J. Syst. Evol. Microbiol.*, 2014, 64, 1825-1825.
22. M. Kraatz, R. J. Wallace and L. Svensson, *Int. J. Syst. Evol. Microbiol.*, 2011, 61, 795-803.
23. K. M. Konwar, N. W. Hanson, M. P. Bhatia, D. Kim, S. J. Wu, A. S. Hahn, C. Morgan-Lang, H. K. Cheung and S. J. Hallam, Bioinformatics, 2015, 31, 3345-3347.
24. V. Lombard, H. Golaconda Ramulu, E. Drula, P. M. Coutinho and B. Henrissat, *Nucleic Acids Res.*, 2014, 42, D490-495.
25. C. S. Yu, Y. C. Chen, C. H. Lu and J. K. Hwang, *Proteins*, 2006, 64, 643-651.
26. J. V. Zurawski, P. A. Khatibi, H. O. Akinosho, C. T. Straub, S. H. Compton, J. M. Conway, L. L. Lee, A. J. Ragauskas, B. H. Davison, M. W. W. Adams and R. M. Kelly, *Appl. Environ. Microbiol.*, 2017, 83.
27. T. Sakamoto and J. F. Thibault, *Appl. Environ. Microbiol.*, 2001, 67, 3319-3321.
28. M. Abdullah and D. French, Arch. *Biochem. Biophys.*, 1970, 137, 483-&.
29. R. S. Ronimus and H. W. Morgan, *Extremophiles*, 2001, 5, 357-373.
30. V. B. Lawlis, M. S. Dennis, E. Y. Chen, D. H. Smith and D. J. Henner, *Appl. Environ. Microbiol.*, 1984, 47, 15-21.
31. J. K. Demmer, N. Pal Chowdhury, T. Selmer, U. Ermler and W. Buckel, *Nat Commun*, 2017, 8, 1577.
32. F. Li, J. Hinderberger, H. Seedorf, J. Zhang, W. Buckel and R. K. Thauer, *J. Bacteriol.*, 2008, 190, 843-850.
33. E. H. Aboulnaga, O. Pinkenburg, J. Schiffels, A. El-Refai, W. Buckel and T. Selmer, *J. Bacteriol.*, 2013, 195, 3704-3713.
34. S. de Kok, J. Meijer, M. C. van Loosdrecht and R. Kleerebezem, *Appl. Microbiol. Biotechnol.*, 2013, 97, 2617-2625.
35. W. Buckel and R. K. Thauer, *Bba-Bioenergetics*, 2013, 1827, 94-113.
36. A. J. Stains and C. M. Plugge, *Nat. Rev. Microbiol.*, 2009, 7, 568-577.
37. F. Zhang, Y. Zhang, M. Chen, M. C. M. van Loosdrecht and R. J. Zeng, *Biotechnol. Bioeng.*, 2013, 110, 1884-1894.
38. J. Rodriguez, R. Kleerebezem, J. M. Lema and M. C. M. van Loosdrecht, *Biotechnol. Bioeng.*, 2006, 93, 592-606.
39. V. Balan, B. Bals, S. P. S. Chundawat, D. Marshall and B. E. Dale, *Biofuels: Methods and Protocols*, 2009, 581, 61-77.
40. L. S. Parreiras, R. J. Breuer, R. Avanasi Narasimhan, A. J. Higbee, A. La Reau, M. Tremaine, L. Qin, L. B. Willis, B. D. Bice, B. L. Bonfert, R. C. Pinhancos, A. J. Balloon, N. Uppugundla, T. Liu, C. Li, D. Tanjore, I. M. Ong, H. Li, E. L. Pohlmann, J. Serate, S. T. Withers, B. A. Simmons, D. B. Hodge, M. S. Westphall, J. J. Coon, B. E. Dale, V. Balan, D. H. Keating, Y. Zhang, R. Landick, A. P. Gasch and T. K. Sato, *PLoS One*, 2014, 9, e107499.
41. W. E. F. American Public Health Association, and American Water Works Association Standard Methods for the Examination of Water and Wastewater: 21st Edition, American Public Health Association, 2005.
42. E. W. Yemm and A. J. Willis, *Biochem. J.*, 1954, 57, 508-514.
43. Joshi, N. A., & Fass, J. N. (2011). Sickle: A sliding-window, adaptive, quality-based trimming tool for FastQ files (Version 1.33).
44. S. Nurk, D. Meleshko, A. Korobeynikov and P. A. Pevzner, *Genome Res.*, 2017, 27, 824-834.
45. Y. W. Wu, B. A. Simmons and S. W. Singer, *Bioinformatics*, 2016, 32, 605-607.
46. D. H. Parks, M. Imelfort, C. T. Skennerton, P. Hugenholtz and G. W. Tyson, *Genome Res.*, 2015, 25, 1043-1055.
47. A. E. Darling, G. Jospin, E. Lowe, F. A. t. Matsen, H. M. Bik and J. A. Eisen, *PeerJ*, 2014, 2, e243.
48. A. Stamatakis, *Bioinformatics*, 2014, 30, 1312-1313.
49. M. Richter, R. Rossello-Mora, F. Oliver Glockner and J. Peplies, *Bioinformatics*, 2016, 32, 929-931.
50. D. Hyatt, G. L. Chen, P. F. Locascio, M. L. Land, F. W. Larimer and L. J. Hauser, *BMC Bioinformatics*, 2010, 11, 119.
51. S. M. Kielbasa, R. Wan, K. Sato, P. Horton and M. C. Frith, *Genome Res.*, 2011, 21, 487-493.
52. C. E. Lawson, S. Wu, A. S. Bhattacharjee, J. J. Hamilton, K. D. McMahon, R. Goel and D. R. Noguera, *Nat Commun*, 2017, 8, 15416.
53. E. Kopylova, L. Noe and H. Touzet, *Bioinformatics*, 2012, 28, 3211-3217.
54. S. Anders, P. T. Pyl and W. Huber, *Bioinformatics*, 2015, 31, 166-169.

Example 3. Refinement of Metagenomes

Background and Results

Figure 10:
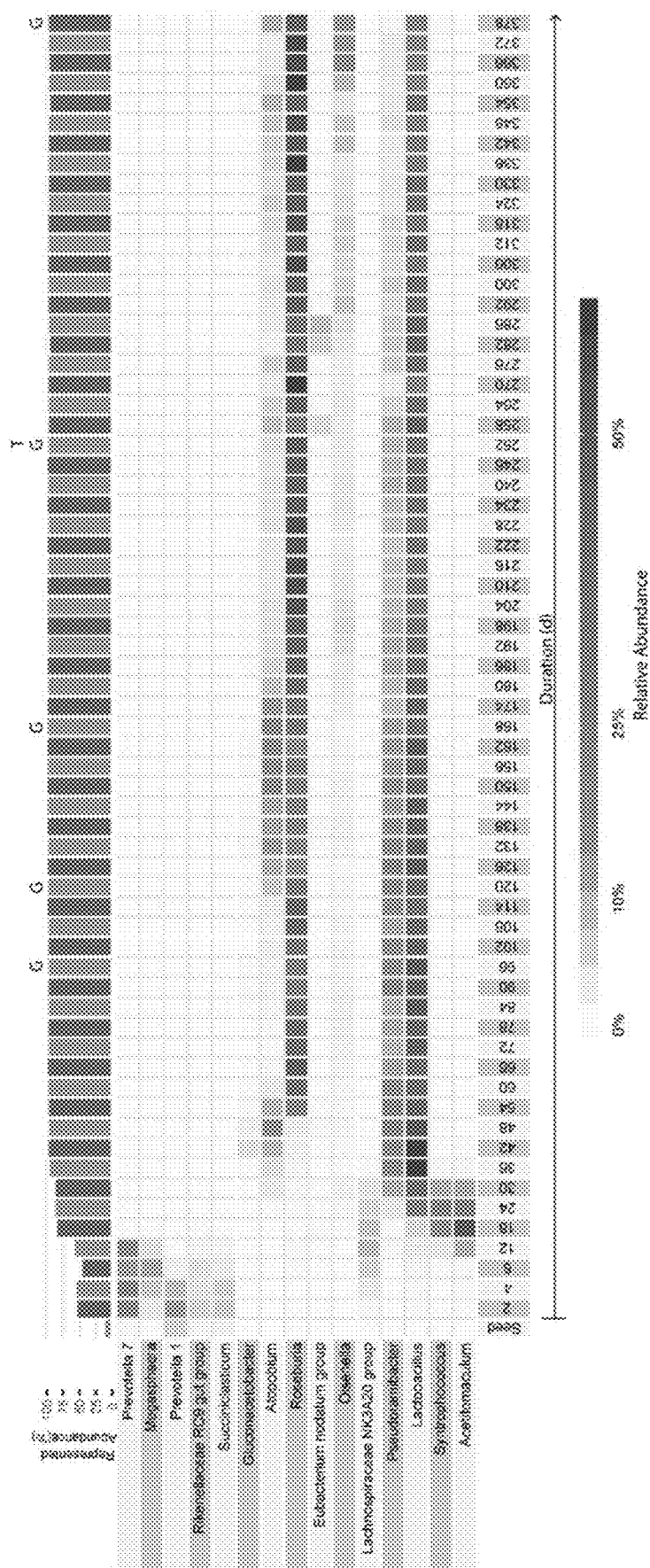
FIG. 10. Relative abundance of bacteria in the bioreactor based on 16S rRNA gene amplicon sequencing. The first column shows results from the acid digester sludge ("seed") used for reactor inoculum. The duration after starting the bioreactor is shown on the x-axis and genera names are provided on the y-axis. The bar plot above the heatmap shows the sum of abundance represented in the heatmap. Colors in the heatmap indicate relative abundance with higher abundance indicated by red color intensity. Samples corresponding to metagenomic and metatranscriptomic samples analyzed in this study are shown with "G" indicating a metagenomic sample and "T" indicating the time point used for the time-series metatranscriptomic analysis.
Figure 11:
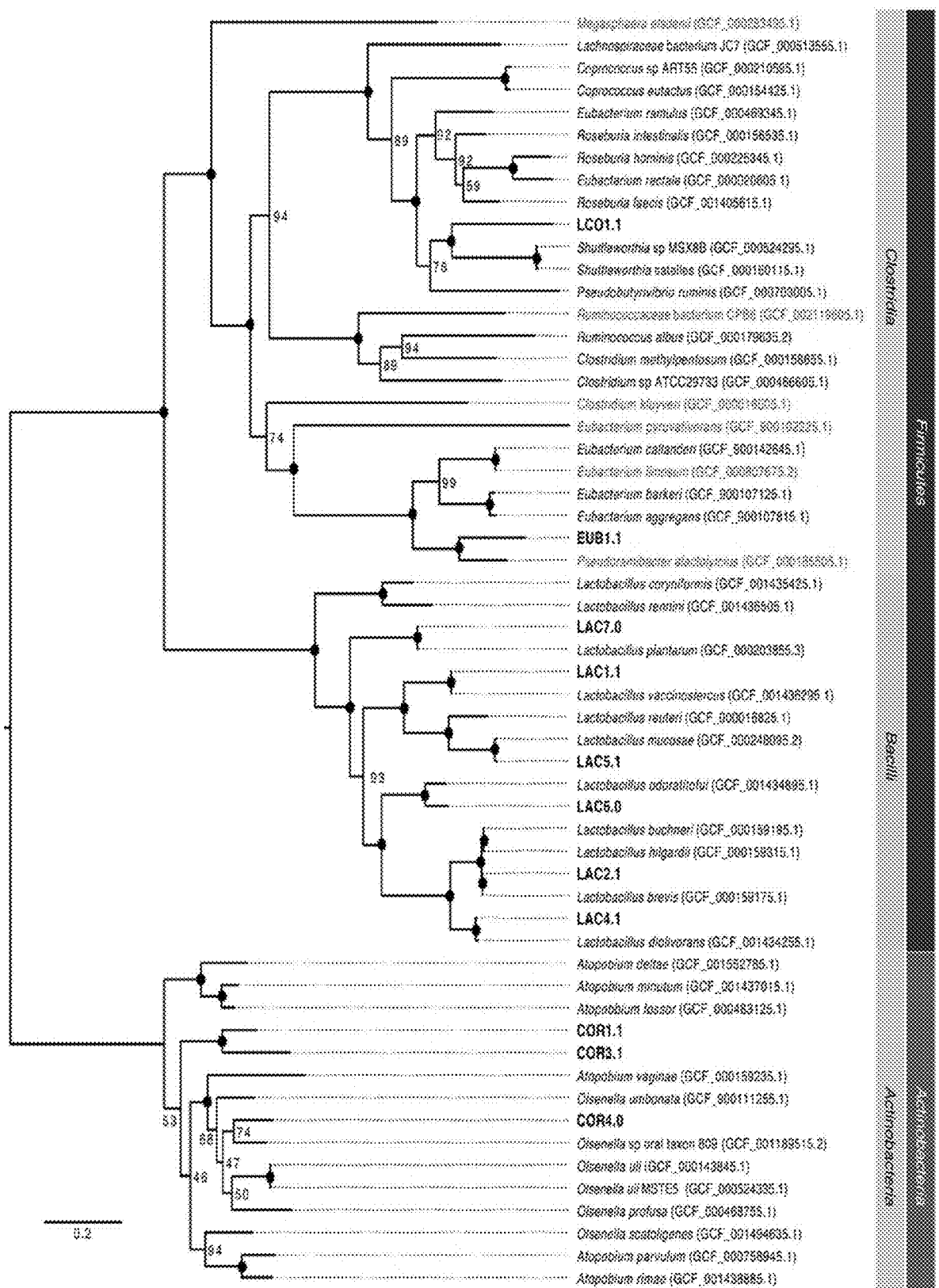
FIG. 11. Phylogenetic tree of the 11 MAGs in the bioreactor at 252 days. Reactor MAGs are shown in bold text. Known hexanoic and octanoic acid producers are shown in red. Bootstrap support values based on 100 bootstraps are shown at tree nodes with filled circle indicating support values of 100.

The examples above report the construction of metagenome-assembled genomes (MAGs) from a MCFA producing microbiome receiving lignocellulosic biorefinery residues, in which LCO1 and EUB1 were the abundant chain elongating MAGs.+ These MAGs were constructed using DNA samples from the first 120 days of reactor operation. To improve the quality of these MAGs, we used additional Illumina and PacBio sequencing reads obtained from the same reactor microbiome at different times during a 378-day operational period. Using metaSpades,[2] we co-assembled 244 million Illumina Hi-seq (2×250) reads from five time points (Days 96, 120, 168, 252, and 378; FIG. 10) into 24,000 contigs. Contigs were binned into 27 draft MAGs with Anvi'o.[3] Bins were gap-filled with the PacBio reads from the 378 d sample using PBJelly.[4] We estimated the quality and phylogeny of the bins with CheckM.[5] This analysis resulted in an improvement in MAG quality with respect to completeness, contamination, and number of contigs (Table 5). Based on DNA read mapping normalized to genome size for Day 252 (the day we conducted our gene expression analysis), eleven MAGs were more than 1% abundant. Similar to our prior study, the bins were named according to a phylogenetic analysis (FIG. 11) that showed that MAGs were related to *Lachnospiraceae* (LCO), *Eubacteriaceae* (EUB), *Coriobacteriaceae* (COR), and *Lactobacillus* (LAC).

TABLE 5

Summary of metagenome-assembled genomes and the relative abundance in the reactor at day 252. Number in brackets indicate values for previously developed MAGs.[1]

| Name | Relative Abundance (%) | Completeness (%) | Contamination (%) | Genome size (Mbp) | No. scaffolds |
|---|---|---|---|---|---|
| LCO1.1 | 75.3 | 96.9 [95.4] | 0.5 [0.0] | 2.39 [2.10] | 10 [44] |
| EUB1.1 | 4.7 | 99.2 [97.8] | 0.2 [0.2] | 2.29 [2.00] | 29 [35] |
| COR1.1 | 2.4 | 95.0 [99.2] | 6.7 [0.8] | 2.41 [2.51] | 82 [225] |
| COR3.1 | 2.8 | 98.4 [98.4] | 2.4 [7.4] | 3.02 [3.65] | 134 [533] |
| COR4.1 | 1.1 | 100 [NA][1] | 0.7 [NA][1] | 2.45 [NA][1] | 8 [NA][1] |
| LAC1.1 | 3.8 | 99.5 [99.5] | 1.1 [1.1] | 2.77 [2.63] | 9 [18] |
| LAC2.1 | 2.0 | 99.4 [99.4] | 1.6 [1.6] | 3.18 [3.18] | 37 [79] |
| LAC4.1 | 1.6 | 97.7 [98.9] | 0.6 [1.3] | 3.14 [3.35] | 53 [95] |
| LAC5.1 | 2.5 | 99.2 [80.1] | 0.0 [0.8] | 2.11 [1.48] | 6 [181] |
| LAC6.1 | 1.9 | 99.1 [NA][1] | 1.1 [NA][1] | 2.80 [NA][1] | 12 [NA][1] |
| LAC7.1 | 2.0 | 99.1 [NA][1] | 2.8 [NA][1] | 3.41 [NA][1] | 33 [NA][1] |

The LCO1.1, EUB1.1, COR1.1, COR3.1, LAC1.1, LAC2.1, LAC4.1, and LAC5.1 MAGs, represented the same organisms that were represented with the LCO1, EU1B1, COR1, COR3, LAC1, LAC2, LAC4, and LAC5 MAGS at the 96-day timepoint. The COR4.1, LAC6.1, and LAC7.1 MAGs represented new *Coriobacteriaceae* (COR4.1) and *Lactobacillus* (LAC6.1 and LAC7.1) organisms now abundant at >1% at the 252-day timepoint. The COR2 and LAC3 MAGs, which were abundant at >1% at the 96-day timepoint, were no longer abundant at greater than 1% at the 252-day timepoint.

REFERENCES

1. M. J. Scarborough, C. E. Lawson, J. J. Hamilton, T. J. Donohue and D. R. Noguera, *mSystems*, 2018, DOI: 0.1128/msystems.00221-18.
2. S. Nurk, D. Meleshko, A. Korobeynikov and P. A. Pevzner, *Genome Res.*, 2017, 27, 824-834.
3. A. M. Eren, O. C. Esen, C. Quince, J. H. Vineis, H. G. Morrison, M. L. Sogin and T. O. Delmont, *PeerJ*, 2015, 3, e1319.
4. A. C. English, S. Richards, Y. Han, M. Wang, V. Vee, J. Qu, X. Qin, D. M. Muzny, J. G. Reid, K. C. Worley and R. A. Gibbs, *PLoS One*, 2012, 7, e47768.
5. D. H. Parks, M. Imelfort, C. T. Skennerton, P. Hugenholtz and G. W. Tyson, *Genome Res.*, 2015, 25, 1043-1055.

SEQUENCE LISTING

The patent contains a lengthy sequence listing. A copy of the sequence listing is available in electronic form from the USPTO web site (https://seqdata.uspto.gov/?pageRequest=docDetail&DocID=US12305215B2). An electronic copy of the sequence listing will also be available from the USPTO upon request and payment of the fee set forth in 37 CFR 1.19(b)(3).

What is claimed is:

1. A microbiome composition comprising a set of microbes, wherein the microbes in the set consist of members of *Lachnospiraceae, Eubacteriaceae, Coriobacteriaceae*, and *Lactobacillusceae*, wherein the number of individual physical microbes in the set constitutes at least 60% of the total number of individual physical microbes in the microbiome composition, wherein the members of *Lachnospiraceae* constitute at least 40% of the total number of individual physical microbes in the microbiome composition, the members of *Eubacteriaceae* constitute at least 2% of the total number of individual physical microbes in the microbiome composition, the members of *Coriobacteriaceae* constitute at least 3% of the total number of individual physical microbes in the microbiome composition, and the members of *Lactobacilluseae* constitute at least 7% of the total number of individual physical microbes in the microbiome composition.

2. The microbiome composition of claim 1, wherein one or more of the members of *Lachnospiraceae* are members of a genus selected from the group consisting of *Roseburia* and *Shuttleworthia*.

3. The microbiome composition of claim 1, wherein one or more of the members of *Eubacteriaceae* are members of *Pseudoramibacter*.

4. The microbiome composition of claim 1, wherein one or more of the members of *Coriobacteriaceae* are members of a genus selected from the group consisting of *Olsenella* and *Atopobium*.

5. The microbiome composition of claim 1, wherein one or more of the members of *Lactobacilliae* are members of *Lactobacillus*.

6. The microbiome composition of claim 1, wherein the number of individual physical microbes in the set constitutes at least 85% of the total number of individual physical microbes in the microbiome composition.

7. The microbiome composition of claim 1, wherein less than 1% of the number of individual physical microbes in the microbiome composition are members of *Ethanoligenens*, *Desulfitobacterium*, *Clostridium*, *Propionibacterium*, *Bifidobacterium*, *Ruminococcaceae*, and *Bifidobacteriaceae*.

8. The microbiome composition of claim 1, wherein one or more of the members of *Lachnospiraceae* are members of a genus selected from the group consisting of *Roseburia* and *Shuttleworthia*, one or more of the members of *Eubacteriaceae* are members of *Pseudoramibacter*, one or more of the members of *Coriobacteriaceae* are members of a genus selected from the group consisting of *Olsenella* and *Atopobium*, and one or more of the members of *Lactobacillus* are members of *Lactobacillus*.

9. The microbiome composition of claim 8, wherein the number of individual physical microbes in the set constitutes at least 85% of the total number of individual physical microbes in the microbiome composition.

10. The microbiome composition of claim 9, wherein less than 1% of the number of individual physical microbes in the microbiome composition are members of *Ethanoligenens*, *Desulfitobacterium*, *Clostridium*, *Propionibacterium*, *Bifidobacterium*, *Ruminococcaceae*, and *Bifidobacteriaceae*.

11. The microbiome composition of claim 8, wherein less than 1% of the number of individual physical microbes in the microbiome composition are members of *Ethanoligenens*, *Desulfitobacterium*, *Clostridium*, *Propionibacterium*, *Bifidobacterium*, *Ruminococcaceae*, and *Bifidobacteriaceae*.

12. The microbiome composition of claim 1, wherein the number of individual physical microbes in the set constitutes at least 85% of the total number of individual physical microbes in the microbiome composition, and wherein less than 1% of the number of individual physical microbes in the microbiome composition are members of *Ethanoligenens*, *Desulfitobacterium*, *Clostridium*, *Propionibacterium*, *Bifidobacterium*, *Ruminococcaceae*, and *Bifidobacteriaceae*.

13. The microbiome composition of claim 1, wherein each of the members of *Lachnospiraceae* in the set are members of a genus selected from the group consisting of *Roseburia* and *Shuttleworthia*, each of the members of *Eubacteriaceae* in the set are members of *Pseudoramibacter*, each of the members of *Coriobacteriaceae* in the set are members of a genus selected from the group consisting of *Olsenella* and *Atopobium*, and each of the members of *Lactobacilloae* in the set are members of *Lactobacillus*.

14. The microbiome composition of claim 13, wherein the number of individual physical microbes in the set constitutes at least 85% of the total number of individual physical microbes in the microbiome composition.

15. The microbiome composition of claim 14, wherein less than 1% of the number of individual physical microbes in the microbiome composition are members of *Ethanoligenens*, *Desulfitobacterium*, *Clostridium*, *Propionibacterium*, *Bifidobacterium*, *Ruminococcaceae*, and *Bifidobacteriaceae*.

16. A method of producing medium-chain fatty acids from an organic substrate comprising anaerobically fermenting the organic substrate for a time sufficient to produce medium-chain fatty acids from the organic substrate with the microbiome composition of claim 1.

17. The method of claim 16, wherein the organic substrate comprises a component selected from the group consisting of xylose, complex carbohydrates, and glycerol.

18. The method of claim 16, wherein the organic substrate comprises a lignocellulosic stillage.

19. The method of claim 16, wherein the fermenting is performed at a pH of about 5 to about 6.5.

20. The method of claim 16, wherein the fermenting is performed without the addition of ethanol and wherein the fermenting does not produce methane.

* * * * *